(12) United States Patent
Braun et al.

(10) Patent No.: US 12,357,674 B2
(45) Date of Patent: *Jul. 15, 2025

(54) METHODS FOR PROMOTING WOUND HEALING AND HAIR GROWTH COMPRISING GDNF ADMINISTRATION

(71) Applicant: The Jackson Laboratory, Bar Harbor, ME (US)

(72) Inventors: Robert E. Braun, Bar Harbor, ME (US); Manju Sharma, Bar Harbor, ME (US)

(73) Assignee: The Jackson Laboratory, Bar Harbor, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/529,590

(22) Filed: Dec. 5, 2023

(65) Prior Publication Data

US 2024/0181008 A1    Jun. 6, 2024

Related U.S. Application Data

(60) Continuation of application No. 17/373,877, filed on Jul. 13, 2021, now Pat. No. 11,890,322, which is a continuation of application No. 16/452,459, filed on Jun. 25, 2019, now abandoned, which is a division of application No. 14/775,386, filed as application No. PCT/US2014/027419 on Mar. 14, 2014, now Pat. No. 10,376,562.

(60) Provisional application No. 61/787,870, filed on Mar. 15, 2013.

(51) Int. Cl.
| | | |
|---|---|---|
| *A61K 38/18* | (2006.01) | |
| *A61G 7/00* | (2006.01) | |
| *A61K 8/64* | (2006.01) | |
| *A61Q 7/00* | (2006.01) | |
| *C07K 14/475* | (2006.01) | |

(52) U.S. Cl.
CPC .............. *A61K 38/185* (2013.01); *A61G 7/00* (2013.01); *A61K 8/64* (2013.01); *C07K 14/4756* (2013.01)

(58) Field of Classification Search
None
See application file for complete search history.

(56) References Cited

U.S. PATENT DOCUMENTS

| | | |
|---|---|---|
| 4,407,957 A | 10/1983 | Lim |
| 4,870,017 A | 9/1989 | Ben-Bassat et al. |
| 4,911,928 A | 3/1990 | Wallach |
| 5,641,749 A | 6/1997 | Yan et al. |
| 5,705,485 A | 1/1998 | Cini et al. |
| 5,733,875 A | 3/1998 | Martin |
| 5,741,778 A | 4/1998 | Martin et al. |
| 5,798,113 A | 8/1998 | Dionne et al. |
| 5,800,828 A | 9/1998 | Dionne et al. |
| 5,834,014 A | 11/1998 | Weiner et al. |
| 5,837,681 A | 11/1998 | Magal |
| 5,929,041 A | 7/1999 | Magal |
| 6,093,802 A | 7/2000 | Lin et al. |
| 6,184,200 B1 | 2/2001 | Hu |
| 6,221,376 B1 | 4/2001 | Lin et al. |
| 6,245,330 B1 | 6/2001 | Horellou et al. |
| 6,362,319 B1 | 3/2002 | Lin et al. |
| 7,226,758 B1 | 6/2007 | Lin et al. |
| 7,390,781 B2 | 6/2008 | Hu |
| 7,479,279 B2 | 1/2009 | Paulista et al. |
| 7,611,865 B2 | 11/2009 | Hu |
| 8,138,148 B2 | 3/2012 | Bock et al. |
| 8,383,114 B2 | 2/2013 | Sloey et al. |
| 10,376,562 B2 | 8/2019 | Braun et al. |
| 11,890,322 B2 | 2/2024 | Braun et al. |
| 2003/0166537 A1 | 9/2003 | Hanke |
| 2004/0097456 A1 | 5/2004 | Paulista et al. |
| 2004/0127419 A1 | 7/2004 | Hu |
| 2006/0134155 A1 | 6/2006 | Dryer et al. |
| 2006/0258576 A1 | 11/2006 | Immonen |
| 2010/0056440 A1 | 3/2010 | Rossomando et al. |
| 2010/0172865 A1 | 7/2010 | Shantha et al. |
| 2010/0311653 A1 | 12/2010 | Nevalaita et al. |
| 2011/0281802 A1 | 11/2011 | Armbruster et al. |
| 2011/0306546 A1 | 12/2011 | Armani et al. |
| 2013/0017285 A1 | 1/2013 | Bhatia |
| 2016/0022773 A1 | 1/2016 | Braun et al. |
| 2019/0307846 A1 | 10/2019 | Braun et al. |
| 2020/0147174 A1 | 5/2020 | Braun et al. |

FOREIGN PATENT DOCUMENTS

| | | |
|---|---|---|
| EP | 0610254 A1 | 8/1994 |
| EP | 0920448 A1 | 6/1999 |
| EP | 1372698 A2 | 1/2004 |

(Continued)

OTHER PUBLICATIONS

[No Author Listed], The printout of the website from the Mayo Clinic, downloaded Nov. 28, 2017 from mayoclinic.org/diseases-conditions/hair-loss/basics/treatment/con-20-027666?p=1; 7 pages total. (Year: 2017).

Aarabi, S. et al., "Hypertrophic scar formation following burns and trauma: new approaches to treatment," PLoS Med.., vol. 4(9):e234:7 pages (2007).

Adly, M.A., et al., "Analysis of the expression pattern of glial cell line-derived neurotrophic factor, neurturin, their cognate receptors GFRalpha-1 and GFRalpha-2, and a common signal transduction element c-Ret in the human scalp skin," J CutanPathol., vol. 33:799-808(2006).

(Continued)

*Primary Examiner* — Christina M Borgeest

(57) ABSTRACT

The present invention generally relates to uses of glial cell line-derived growth factor (GDNF) in cutaneous wound healing and hair growth. Methods of effecting hair growth and/or wound healing which feature administration of GDNF, or a biologically active fragment thereof, to subjects, e.g., human subject, are disclosed herein. The invention relates also to formulations and kits for achieving the indicated pharmaceutical advantages.

18 Claims, 11 Drawing Sheets

Specification includes a Sequence Listing.

(56) References Cited

FOREIGN PATENT DOCUMENTS

| JP | 2012-246249 B2 | 12/2012 |
|---|---|---|
| WO | WO 93/06116 A1 | 4/1993 |
| WO | WO 97/19694 A1 | 6/1997 |
| WO | WO 99/07843 A1 | 2/1999 |
| WO | WO 00/01815 A2 | 1/2000 |
| WO | WO 01/30375 A2 | 5/2001 |
| WO | WO 02/076494 A2 | 10/2002 |
| WO | WO 2005/023861 A2 | 3/2005 |
| WO | WO 2007103182 A2 | 9/2007 |
| WO | WO 2014/152511 A1 | 9/2014 |

OTHER PUBLICATIONS

Adly, M.A., et al., "Expression patterns of the glial cell line-derived neurotrophic factor, neurturin, their cognate receptors GFRalpha-1, GFRalpha-2, and a common signal transduction element c-Ret in the human skin hair follicles," J Am AcadDermatol., vol. 58:238-250 (2008).
Albers, K.M., et al., "Glial cell-line-derived neurotrophic factor expression in skin alters the mechanical sensitivity of cutaneous nociceptors," J Neurosci., vol. 26: 2981-2990 (2006).
Albers, K.M., et al., "The skin as a neurotrophic organ," Neuroscientist, vol. 13: 371-382 (2007).
Altschul et al., "Basic Local Alignment Search Tool," J. Mol. Biol. 215:403-410, (1990).
Altschul et al., "Gapped BLAST and PSI-BLAST: a new generation of protein database search programs," Nucleic Acids Research, vol. 25(17):3389-3402 (1997).
Altschuler, R.A., "Stress pathways in the rat cochlea and potential for protection from acquired deafness," Audiol Neurootol., vol. 7: 152-156. (2002).
Altschuler, R.A., et al. (1999). Rescue and regrowth of sensory nerves following deafferentation by neurotrophic factors. Ann N Y Acad Sci 884, 305-311.
Anand, P., "Neurotrophic factors and their receptors in human sensory neuropathies," Prog Brain Res., vol. 146: 477-492 (2004).
Anand, U., et al., "TRPA1 receptor localisation in the human peripheral nervous system and functional studies in cultured human and rat sensory neurons," Neurosci Lett., vol. 438: 221-227 (2008).
Aoki, Y., et al., "Expression and co-expression of VR1, CGRP, and IB4-binding glycoprotein in dorsal root ganglion neurons in rats: differences between the disc afferents and the cutaneous afferents," Spine (Phila Pa 1976), vol. 30: 1496-1500(2005).
Ayllon, J., et al., "Long-term response and postsurgical complete remissions after treatment with sunitinib malate, an oral multitargeted receptor tyrosine kinase inhibitor, in patients with metastatic renal cell carcinoma," Cancer Invest., vol. 29:282-285 (2011).
Baba, T., et al. "Electrical stimulation of the cerebral cortex exerts antiapoptotic, angiogenic, and anti-inflammatory effects in ischemic stroke rats through phosphoinositide 3-kinase/Akt signaling pathway," Stroke, vol. 40: e598-605 (2009).
Barrientos S, et al., "Growth factors and cytokines in wound healing," Wound Repair Regen, vol. 16:585-601 (2008).
Batchelor, P.E., et al., "Activated macrophages and microglia induce dopaminergic sprouting in the injured striatum and express brain-derived neurotrophic factor and glial cell line-derived neurotrophic factor," J Neurosci., vol. 19: 1708-1716.(1999).
Batchelor, P.E., et al., "Inhibition of brain-derived neurotrophic factor and glial cell line-derived neurotrophic factor expression reduces dopaminergic sprouting in the injured striatum," Eur J Neurosci., vol. 12: 3462-3468 (2000).
Batchelor, P.E., et al., "Macrophages and Microglia Produce Local Trophic Gradients That Stimulate Axonal Sprouting Toward but Not beyond the Wound Edge," Mol Cell Neurosci., vol. 21: 436-453 (2002).
Batchelor, P.E., et al., "Stimulation of axonal sprouting by trophic factors immobilized within the wound core," Brain Res., vol. 1209: 49-56 (2008).

Baudet, C., et al. "Positive and negative interactions of GDNF, NTN and ART in developing sensory neuron subpopulations, and their collaboration with neurotrophins," Development, vol. 127: 4335-4344 (2000).
Becker, D.L., et al.,"Connexins in wound healing; perspectives in diabetic patients," Biochim. Biophys Acta, vol. 1818:2068-2075 (2011).
Bennett NT, et al., "Growth factors and wound healing: Part II. Role in normal and chronic wound healing," Am J Surg, . vol. 166:74-81 (1993).
Birch et al., Female pattern hair loss. Clin Exp Dermatol. Jul. 2002;27(5):383-88. doi: 10.1046/j.1365-2230.2002.01085.x.
Botchkareva et al., American Journal of Pathology, 2000; 156: 1041-1053.
Botchkareva et al., New roles for glial cell line-derived neurotrophic factor and neurturin: involvement in hair cycle control. Am J Pathol. Mar. 2000;156(3):1041-53. doi: 10.1016/S0002-9440(10)64972-3.
Bourane, S., et al., "Low-threshold mechanoreceptor subtypes selectively express MafA and are specified by Ret signaling." Neuron, vol. 64: 857-870 (2009).
Bowenkamp, K.E., et al., "Intracerebroventricular glial cell line-derived neurotrophic factor improves motor function and supports nigrostriatal dopamine neurons in bilaterally 6-hydroxydopamine lesioned rats," Exp Neurol., vol. 145: 104-117.(1997).
Bradbury, E.J., et al., "The expression of P2X3 purinoreceptors in sensory neurons: effects of axotomy and glial-derived neurotrophic factor," Mol Cell Neurosci., vol. 12: 256-268 (1998).
Braiman-Wilksman, L. et al., "Novel Insights into Wound Healing Sequence of Events," Toxicol. Pathol., vol. 25: 767-779(2007).
Brem, H. et al. "Healing of elderly patients with diabetic foot ulcers, venous stasis ulcers, and pressure ulcers," Surg Technol Int., vol. 11, 161-167 (2003).
Bukowiecki et al., Wound-Healing Studies in Cornea and Skin: Parallels, Differences and Opportunities. Int J Mol Sci. Jun. 12, 2017;18(6):1257. doi: 10.3390/ijms18061257.
Burt, Evolutionary grouping of the transforming growth factor-beta superfamily. Biochem Biophys Res Commun. Apr. 30, 1992;184(2):590-5.
Carlsten et al., Society for Neuroscience Abstract Viewer and Itinerary Planner. 32nd Annual Meeting of the Society for Neuroscience. Nov. 2002. Abstract No. 757.5.
Carlsten, J.A., et al., "Glial cell line-derived neurotrophic factor-responsive and neurotrophin-3-responsive neurons require the cytoskeletal linker protein dystonin for postnatal survival," J Comp Neurol., vol. 432: 155-168 (2001).
Cavanagh, P.R., et al. "The non-healing diabetic foot wound: fact or fiction?," Ostomy Wound Manage, vol. 44(3A supp), 6S-12S (1998).
Chang, H et al., "Genetic analysis of the mammalian transforming growth factor-beta superfamily," Endocri Rev, vol. 23(6):787-823 (2002).
Charron, M. et al., "A 3-kilobase region derived from the rat cathepsin L gene directs in vivo expression of a reporter gene in sertoli cells in a manner comparable to that of the endogenous gene," Biol Reprod, vol. 81(3):1641-1648 (2003).
Chen, S.H., et al., "Premarin stimulates estrogen receptor-alpha to protect against traumatic brain injury in male rats," Crit Care Med., vol. 37: 3097-3106 (2009).
Chi, J.H., "Scar-busting chondroitinase with peripheral nerve grafting promotes axonal regeneration in chronic spinal cord injury," Neurosurgery, vol. 66: N12 (2010).
Christianson, J.A., et al., "Restorative effects of neurotrophin treatment on diabetes-induced cutaneous axon loss in mice," Exp Neurol., vol. 179, 188-199 (2003).
Cobianchi, S., et al., "Differential effects of activity dependent treatments on axonal regeneration and neuropathic pain after peripheral nerve injury," Exp Neurol., vol. 240:157-167 (2013).
Conley et al., Recombinant protein production in a variety of Nicotiana hosts: a comparative analysis. Plant Biotechnol J. May 2011;9(4):434-44. doi: 10.1111/j.1467-7652.2010.00563.x. Epub Oct. 8, 2010.

(56) References Cited

OTHER PUBLICATIONS

Deng, L.X., et al., "GDNF modifies reactive astrogliosis allowing robust axonal regeneration through Schwann cell-seeded guidance channels after spinal cord injury," Exp Neurol., vol. 229: 238-250. (2011).
Deonarine, K., et al, "Gene expression profiling of cutaneous wound healing," J. Transl. Med., vol. 5 (2007).
Dhurat, R. et al., "Hair evaluation methods: merits and demerits," Int J Trichology 1(2): 108-119 (2009).
Diegelmann, R.F., et al, "Wound healing: an overview of acute, fibrotic and delayed healing," Front Biosci, vol. 9:283-289 (2004).
Donahue, T.R., et al., "CXCR2 and RET single nucleotide polymorphisms in pancreatic cancer," World J Surg., vol. 33, 710-715 (2009).
Ebadi, M., et al., "Neurotrophins and their receptors in nerve injury and repair," Neurochem Int., vol. 30: 347-374 (1997).
Eigenbrot et al., "X-ray structure of glial cell-derived neurotrophic factor at 1.9 A resolution and implications for receptor binding," Nat Struct Biol., vol. 4 (6):435-438 (1997).
Eketjall et al. "Distinct structural elements in GDNF mediate binding to GFRalpha1 and activation of the GFRalpha-c-Ret receptor complex," EMBO, vol. 18(21): 5901-5910 (1999).
Elcin YM et al., "Controlled release of endothelial cell growth factor from chitosan-albumin microspheres for localized angiogenesis: in vitro and in vivo studies," Artif. Cell Blood Substit. Immobil Biotechnol., vol. 24 (3): 257-271 (1996).
Elitt, C.M., et al. "Artemin overexpression in skin enhances expression of TRPV1 and TRPA1 in cutaneous sensory neurons and leads to behavioral sensitivity to heat and cold," J Neurosci., vol. 26: 8578-8587 (2006).
Elitt, C.M., et al., "Overexpression of artemin in the tongue increases expression of TRPV1 and TRPA1 in trigeminal afferents and causes oral sensitivity to capsaicin and mustard oil," Brain Res., vol. 1230: 80-90 (2008).
Falanga V, et al., "The "trap" hypothesis of venous ulceration," Lancet, vol. 341:1006-1008 (1993).
Fernandez-San Millan et al., "Expression of recombinant proteins lacking methionine as N-terminal amino acid in plastids: human serum albumin as a case study," J Biotechnol., vol. 127(4):593-604 (2007).
Freedberg M, et al., "Keratins and the keratinocyte activation cycle," J Invest Dermatol., vol. 116(5):633-640 (2001).
Freedman, G., et al. "Practical treatment of pain in patients with chronic wounds: pathogenesis-guided management," Am J Surg., vol. 188(1A Suppl):31-35 (2004).
Friedrich, R.E., et al., "Vascular wall cells contribute to tumourigenesis in cutaneous neurofibromas of patients with neurofibromatosis type 1. A comparative histological, ultrastructural and immunohistochemical study," Anticancer Res., vol. 32:2139-2158 (2012).
Fritzsch, B. et al. "Making and breaking the innervation of the ear: neurotrophic support during ear development and its clinical implications," Cell Tissue Res., vol. 295:369-382 (1999).
Fundin, B.T., et al., "A rapid and dynamic regulation of GDNF-family ligands and receptors correlate with the developmental dependency of cutaneous sensory innervation," Development, vol. 126: 2597-2610 (1999).
GENBANK Submission; NIH/NCBI, Accession No. L19063.1. Lin et al., Jun. 8, 1993. 1 page.
Ghassemi, F., et al., "Betal adducin gene expression in DRG is developmentally regulated and is upregulated by glial-derived neurotrophic factor and nerve growth factor," Brain Res Mol Brain Res., vol. 90 :118-124 (2011).
Gilliver, S.C., et al., "MIF: a key player in cutaneous biology and wound healing," Exp. Dermatol.,vol. 20(1): 1-6 (2011).
Golden, J.P., et al., "Expression of neurturin, GDNF, and GDNF family-receptor mRNA in the developing and mature mouse," Exp Neurol., vol. 158: 504-528 (1999).
Grose R, et al., "Wound-healing studies in transgenic and knockout mice," Mol Biotechnol., vol. 28(2):147-166 (2004).
Gudi, V., et al., "Spatial and temporal profiles of growth factor expression during CNS demyelination reveal the dynamics of repair priming," PLoS One, vol. 6: e22623 (2011).
Gurtner GC, et al., "Wound repair and regeneration," Nature, vol. 453(7193):314-321 (2008).
Hackam, D.J., et al., "Cellular, biochemical, and clinical aspects of wound healing," Surg Infect., vol. 3 (Suppl 1), S23-S35 (2002).
Hakuba, N., et al., Adenovirus-mediated overexpression of a gene prevents hearing loss and progressive inner hair cell loss after transient cochlear ischemia in gerbils. Gene Ther 10, 426-433 (2003).
Hantash BM, et al.,"Adult and fetal wound healing," Front Biosci., vol. 13:51-61 (2008).
Harding, K.G., et al., "Wound chronicity and fibroblast senescence—implications for treatment," Int Wound J., vol. 2 (4):364-368 (2005).
Hellmich et al., "Embryonic expression of glial cell-line derived neurotrophic factor (GDNF) suggests multiple developmental roles in neural differentiation and epithelial-mesenchymal interactions.," Mech Dev., vol. 54(1): 95-105 (1996).
Hess, D.C., et al., "Stem cells and neurological diseases," Cell Prolif., vol. 41 (Suppl 1): 94-114 (2008).
Hiltunen, P.H., et al., "Sympathetic cholinergic target innervation requires GDNF family receptor GFR alpha 2," Mol Cell Neurosci., vol. 26: 450-457 (2004).
Hsieh, J.H., et al., "Patterns of target tissue reinnervation and trophic factor expression after nerve grafting," Plast Reconstr Surg. (2013).
Hsieh, Y.L., et al., "Effects of 4-methylcatechol on skin reinnervation: promotion of cutaneous nerve regeneration after crush injury," J Neuropathol Exp Neurol., vol. 68:1269-1281 (2009).
Huang et al., Abstracts presented at the 12th International Congress on Amino Acids, Peptides and Proteins. Amino Acids. Jul. 2011;41(1):S20.
Imamura, T., et al., "The microenvironment of freeze-injured mouse urinary bladders enables successful tissue engineering," Tissue Eng., Part A 15: 3367-3375 (2009).
Ishida, A., et al., "Approach to ex vivo gene therapy in the treatment of Parkinson's disease," Brain Dev., vol. 22 (Suppl 1):S143-147 (2000).
Jankowski, M.P., et al., "Enhanced artemin/GFRalpha3 levels regulate mechanically insensitive, heat-sensitive C-fiber recruitment after axotomy and regeneration," J Neurosci., vol. 30: 16272-16283 (2010).
Jeon, S.M., et al., "Monocyte chemoattractant protein-1 immunoreactivity in sensory ganglia and hindpaw after adjuvant injection," Neuroreport, vol. 19: 183-186. (2008).
Johanson, C., et al., "Traumatic brain injury and recovery mechanisms: peptide modulation of periventricular neurogenic regions by the choroid plexus-CSF nexus," J Neural Transm., vol. 118: 115-133 (2011).
Jones, K.R., et al., "Evidence-based management of chronic wounds," Adv. Skin Wound Care vol. 20(11):591-600 (2007).
Kanzaki, S., et al., "From gene identification to gene therapy," Audiol Neurootol., vol. 7: 161-164 (2002).
Kanzaki, S., et al., "Glial cell line-derived neurotrophic factor and chronic electrical stimulation prevent VIII cranial nerve degeneration following denervation," J Comp Neurol., vol. 454: 350-360 (2002).
Kao, C.H., et al., "Body cooling ameliorating spinal cord injury may be neurogenesis-, anti-inflammation- and angiogenesis-associated in rats," J Trauma, vol. 70: 885-893 (2011).
Karlin, S. et al., "Methods for assessing the statistical significance of molecular sequence features by using general scoring schemes," Proc. Natl. Acad. Sci. USA, vol. 87:2264-2268, (1990).
Karlin, S., "Applications and statistics for multiple high-scoring segments in molecular sequences," Proc. Natl. Acad. Sci., USA, vol. 90:5873-5877 (1993).
Kato, M et al., "RET tyrosine kinase enhances hair growth in association with promotion of melanogenesis," Oncogene, vol. 20: 7536-7541 (2001).
Kawamoto, K., et al., "Gene-based therapy for inner ear disease," Noise Health, vol. 3: 37-47 (2001).

(56) References Cited

OTHER PUBLICATIONS

Kawamoto, K., et al., "Hearing and hair cells are protected by adenoviral gene therapy with TGF-betal and GDNF," Mol Ther., vol. 7: 484-492 (2003).
Keithley, E.M., et al., "GDNF protects the cochlea against noise damage," Neuroreport, vol. 9, 2183-2187 (1998).
Kesser, B.W., et al. "Gene transfer in human vestibular epithelia and the prospects for inner ear gene therapy," Laryngoscope, vol. 118:821-831 (2008).
Kiasalari, Z., et al., "Identification of perineal sensory neurons activated by innocuous heat," J Comp Neurol., vol. 518:137-162 (2010).
Kiwanuka, E. et al., "Harnessing Growth Factors to Influence Wound Healing," Growth Factors and Wound Healing, Clin. Plastic Surgery, vol. 39:239-248 (2012).
Koltzenburg, M., et al., "The changing sensitivity in the life of the nociceptor," Pain Suppl., vol. 6: S93-S102 (1999).
Komeda, M., et al., "The influence of interleukin-1 receptor antagonist transgene on spiral ganglion neurons," Hear Res., vol. 131:1-10 (1999).
Kuang, R., et al., "Glial cell line-derived neurotrophic factor. Potential for otoprotection," Ann N Y Acad Sci., vol. 884:270-291 (1999).
Kumar, S. "Classification and management of acute wounds," Surgery, vol. 26:43-47 (2008).
Lawson, J., et al., "Changes in skin levels of two neutotrophins (glial cell line derived neurotrohic factor and neurotrophin-3) cause alterations in cutaneous neuron responses to mechanical stimuli;" Acta Physiologica Sinica, vol. 60: 584-596(2008).
Lee, Y.J., et al., "Upregulation of bradykinin B2 receptor expression by neurotrophic factors and nerve injury in mouse sensory neurons," Mol Cell Neurosci., vol. 19: 186-200. (2002).
Leibovich, S.J., et al., "The role of the macrophage in wound repair. A study with hydrocortisone and antimacrophage serum," Am. J. Pathol., vol. 78(1):71-100 (1975).
Levin, M. E., "Preventing amputation in the patient with diabetes," Diabetes Care., vol. 18(10): 1383-1394 (1995).
Lin et al. "GDNF: a glial cell line-derived neurotrophic factor for midbrain dopaminergic neurons, "Science, vol. 260 (5111): 1130-1132 (1993).
Lin et al., "Purification and initial characterization of rat B49 glial cell line-derived neurotrophic factor," Neurochem, vol. 63 (2): 758-768 (1994).
Lin, Y.C., et al., "Keratin gel filler for peripheral nerve repair in a rodent sciatic nerve injury model;" Plast Reconstr Surg., vol. 129: 67-78 (2012).
Lindfors, P.H., et al., "Deficient nonpeptidergic epidermis innervation and reduced inflammatory pain in glial cell line-derived neurotrophic factor family receptor alpha2 knock-out mice," J Neurosci., vol. 26:1953-1960 (2006).
Lisse et al., GDNF promotes hair formation and cutaneous wound healing by targeting bulge stem cells. NPJ Regen Med. Jun. 12, 2020;5:13.
Liu, Y., et al. "Protection against aminoglycoside-induced ototoxicity by regulated AAV vector-mediated GDNF gene transfer into the cochlea," Mol Ther., vol. 16: 474-480 (2008).
Lovvom, HN 3rd, et al., "Relative distribution and crosslinking of collagen distinguish fetal from adult sheep wound repair," Pediatr Surg., vol. 34(1):218-223 (1999).
Lu. B., et al., "A novel immunoprecipitation strategy identifies a unique functional mimic of the glial cell line-derived neurotrophic factor family ligands in the pathogen Trypanosoma cruzi," Infect Immun., vol. 76: 3530-3538 (2008).
Lupo M., "Cosmeceutical Peptides," Dermatol Surg., vol. 31:832-836 (2005).
Lupo M., et al., "Cosmeceutical peptides," Dermatol Ther., vol. 20(7 Pt 2)::343-349 (2007).
Machine translation of the specification of published Korean application KR889460; 13 pages total.

Malgrange, B., et al., "Expression of growth factors and their receptors in the postnatal rat cochlea," Neurochem Res., vol. 23:1133-1138 (1998).
Malgrange, B., et al., "Identification of factors that maintain mammalian outer hair cells in adult organ of Corti explants," Hear Res., vol. 170: 48-58 (2002).
Malin, S., et al., "TRPV1 and TRPA1 function and modulation are target tissue dependent" J Neurosci., vol. 31: 10516-10528 (2011).
Malin, S.A., et al., "Glial cell line-derived neurotrophic factor family members sensitize nociceptors in vitro and produce thermal hyperalgesia in vivo," J Neurosci., vol. 26: 8588-8599 (2006).
Marchler-Baeur, M. et al., "CDD: conserved domains and protein three-dimensional structure," Nucleic Acids Res., vol. 41:D348-352, 2013.
Martin P, et al., "Inflammatory cells during wound repair: the good, the bad and the ugly," Trends Cell Biol., vol. 15 (11):599-607 (2005).
Martin, D.M., et al., "Gene-based diagnostic and treatment methods for tinnitus," Int Tinnitus, vol. 9:3-10 (2003).
Mast BA, et al., "Interactions of cytokines, growth factors, and proteases in acute and chronic wounds," Wound Repair Regen., vol. 4(4):411-420 (1996).
McLeod, M., et al., "Erythropoietin and GDNF enhance ventral mesencephalic fiber outgrowth and capillary proliferation following neural transplantation in a rodent model of Parkinson's disease," Eur J Neurosci., vol. 24:361-370 (2006).
Molliver, D.C., et al., "Overexpression of NGF or GDNF alters transcriptional plasticity evoked by inflammation," Pain, vol. 113: 277-284 (2005).
Morimoto, T., et al, "Striatal stimulation nurtures endogenous neurogenesis and angiogenesis in chronic-phase schemic stroke rats," Cell Transplant, vol. 20: 1049-1064 (2011).
Mosser, D.M., et al.,"Exploring the full spectrum of macrophage activation," Nature Rev. Immunol., vol. 8:958-969 (2008).
Mousley, M., "Diabetes and its effect on wound healing and patient care," Nurs Times, vol. 99(42): 70-74 (2003).
Murota, H., et al., "Artemin causes hypersensitivity to warm sensation, mimicking warmth-provoked pruritus in atopic dermatitis," J Allergy Clin Immunol., vol. 130: 671-682/e674 (2012).
Mustoe T., "Understanding chronic wounds: a unifying hypothesis on their pathogenesis and implications for therapy," Am J Surg., vol. 187(5A):65S-70S (2004).
Muzzarelli, "Chitins and chitosans for the repair of wounded skin, nerve, cartilage and bone," RAA, Carbohydrate Polymers: vol. 76: 167-182 (2009).
Myers, E. et al., "Optimal alignments in linear space," Cabios, vol. 4(1): 11-17(1988).
Nakagawa et al., "Enzymatic Cleavage of Amino Terminal Methionine from Recombinant Human Interleukin 2 and Growth Hormone by Aminopeptidase M," Nature Biotech, vol. 5:824-827 (1987).
Nakajima, T., et al., "Differences in innervation and innervated neurons between hip and inguinal skin," Clin Orthop Relat Res., vol. 466: 2527-2532 (2008).
Nakamura, A., et al., "Recent advances in neuropharmacology of cutaneous nociceptors," Jpn J Pharmacol., vol. 79: 427-431 (1999).
Narita, N., et al., "Functional RET G691S polymorphism in cutaneous malignant melanoma," Oncogene, vol. 28: 3058-3068 (2009).
Nwomeh BC, et al., "Physiology of the chronic wound," Clin Plast Surg., vol. 25(3):341-356 (1998).
Obata, K., et al., "TRPA1 induced in sensory neurons contributes to cold hyperalgesia after inflammation and nerve injury," J Clin Invest., vol. 115: 2393-2401 (2005).
Ogiso T, et al., "Effect of positively and negatively charged liposomes on skin permeation of drugs," (2001). J Drug Targeting, vol. 9(1):49-59 (2001).
Okun, E., et al., "Upregulation of carp GDNF mRNA by the immunomodulator AS101," Dev Comp Immunol., vol. 30:441-446 (2006).
Papaetis, G.S., et al., "Sunitinib: a multitargeted receptor tyrosine kinase inhibitor in the era of molecular cancer therapies," BioDrugs, vol. 23:377-389 (2009).

(56) References Cited

OTHER PUBLICATIONS

Patel M, et al., "GDNF-chitosan blended nerve guides: a functional study," J tissue Eng. & Regenerative Med., vol. 1 (5):360-367 (2007).
Paus, R. et al., "The biology of hair follicles," NEJM, vol. 341(7):491-497 (1999).
Perala, N., et al., "Sema4C-Plexin B2 signalling modulates ureteric branching in developing kidney," Differentiation, vol. 81: 81-91 (2011).
Piltonen, M. et al., "Vascular endothelial growth factor C acts as a neurotrophic factor for dopamine neurons in vitro and in vivo," Neuroscience, vol. 192: 550-563 (2011).
Pitera, J.E., et al., "Fras1, a basement membrane-associated protein mutated in Fraser syndrome, mediates both the initiation of the mammalian kidney and the integrity of renal glomeruli," Hum Mol Genet., vol. 17: 3953-3964 (2008).
Qi H., et al., "Expression of glial cell-derived neurotrophic factor and its receptor in the stem-cell-containing human limbal epithelium," Br J Ophthalmol., vol. 92: 1269-1274 (2008).
Qun, L.X., et al., "Neurotrophic factors in the auditory periphery," Ann N Y Acad Sci., vol. 884: 292-304 (1999).
Ramot Y. et al. "Spermidine promotes human hair growth and is a novel modulator of human epithelial stem cell functions," PLoS One, vol. 6(7): e22564 (2011).
Rice, J., et al., "Transgenic rescue of aganglionosis and piebaldism in lethal spotted mice," Dev Dyn., vol. 217:120-132. (2000).
Robson MC, et al., "Wound healing trajectories as predictors of effectiveness of therapeutic agents," Arch Surg., vol. 135(7):773-777 (2000).
Rodero, M.P., et al., "Skin wound healing modulation by macrophages," Int. J. Clin. Exp. Pathol., vol. 3(7):643-653 (2010).
Roggenkamp, D., et al., "Atopic keratinocytes induce increased neurite outgrowth in a coculture model of porcine dorsal root ganglia neurons and human skin cells," J Invest Dermatol., vol. 132: 1892-1900 (2012).
Sadick et al., "Analysis of heregulin-induced ErbB2 phosphorylation with a high-throughput Kinase receptor activation enzyme-linked immunosorbant assay," Anal. Biochem., vol. 235(2): 207-214 (1996).
Sakai, A., et al., "Profiling the cytokines in gingival crevicular fluid using a cytokine antibody array," J Periodontol., vol. 77: 856-864 (2006).
Sanjay et al., "Identification of Newborn Cells by BrdU Labeling and Immunocytochemistry in Vivo," Methods in Mol Biol., vol. 438: 335-343 (2008).
Sariola, H., et al., "Cell lineages in the embryonic kidney: their inductive interactions and signalling molecules," Biochem Cell Biol., vol. 76: 1009-1016 (1998).
Sariola, H., et al., "The neurotrophic factors in non-neuronal tissues," Cell Mol Life Sci., vol. 58:1061-1066 (2001).
Sasaki, K., et al., "Analysis of serum angiogenic factors in a young multiple myeloma patient with high-output cardiac failure," Int J Hematol., vol. 86: 72-76 (2007).
Scheper, V., et al., Effects of delayed treatment with combined GDNF and continuous electrical stimulation on spiral ganglion cell survival in deafened guinea pigs.J Neurosci Res 87, 1389-1399 (2009).
Schmidt-Ullrich and Paus, "Molecular principles of hair follicle induction and morphogenesis," BioEssays, vol. 27(3): 247-261 (2005).
Schultz et al., EGF and TGF-alpha in wound healing and repair. J Cell Biochem. Apr. 1991;45(4):346-52.
Shang, J., et al., "Strong neurogenesis, angiogenesis, synaptogenesis, and antifibrosis of hepatocyte growth factor in rats brain after transient middle cerebral artery occlusion," J Neurosci Res., vol. 89: 86-95 (2011).
Shi, H., et al., "Glial cell line-derived neurotrophic growth factor increases motility and survival of cultured mesenchymal stem cells and ameliorates acute kidney injury," Am J Physiol Renal Physiol., vol. 294: F229-235 (2008).

Shibata, S.B., et al., "Administration of amitriptyline attenuates noise-induced hearing loss via glial cell line-derived neurotrophic factor (GDNF) induction," Brain Res., vol. 1144:74-81 (2007).
Shimamura, M., et al., "Experimental and clinical application of plasmid DNA in the field of central nervous diseases," Curr Gene Ther., vol. 11: 491-500 (2011).
Shoji, F., et al., "Differential protective effects of neurotrophins in the attenuation of noise-induced hair cell loss," Hear Res., vol. 146:134-142 (2000).
Shoji, F., et al., "Glial cell line-derived neurotrophic factor has a dose dependent influence on noise-induced hearing loss in the guinea pig cochlea," Hear Res., vol. 142: 41-55 (2000).
Sindrilaru, A., et al., "An unrestrained proinflammatory M1 macrophage population induced by iron impairs wound healing in humans and mice,". Clin. Invest., vol. 121(3):985-997 (2011).
Singer, A.J., et al., "Cutaneous wound healing," N. Engl. J. Med., vol. 341(10):738-746 (1999).
Steele, C. et al., "Corneal wound Healing: a review," Optometry Today, Sep. 24, 1999, pp. 28-32.
Stenn and Paus "Controls of Hair Follicle Cycling". Physiological Reviews, vol. 81 (1): 449-494 (2001).
Stover, T., et al., "Glial cell line-derived neurotrophic factor (GDNF) and its receptor complex are expressed in the auditory nerve of the mature rat cochlea," Hear Res., vol. 155, 143-151 (2001).
Stucky, C.L., et al., "The low-affinity neurotrophin receptor p75 regulates the function but not the selective survival of specific subpopulations of sensory neurons," J Neurosci., vol. 17, 4398-4405 (1997).
Suzuki, M., et al., "Effect of transgenic GDNF expression on gentamicin-induced cochlear and vestibular toxicity," Gene Ther., vol. 7:1046-1054 (2000).
Takasu, K., et al., "Overexpression of GDNF in the uninjured DRG exerts analgesic effects on neuropathic pain following segmental spinal nerve ligation in mice," J Pain, vol. 12: 1130-1139 (2011).
Takeda, M et al., "Glial cell line-derived neurotrophic factor acutely modulates the excitability of rat small-diameter trigeminal ganglion neurons innervating facial skin," Brain Behav Immun., vol. 24: 72-82 (2010).
Takeda, M., et al., "Glial cell line-derived neurotrophic factor modulates the excitability of nociceptive trigeminal ganglion neurons via a paracrine mechanism following inflammation," Brain Behav Immun., vol. 28: 100-107 (2013).
Tang, M.J., et al., "The RET-glial cell-derived neurotrophic factor (GDNF) pathway stimulates migration and chemoattraction of epithelial cells," J Cell Biol., vol. 142:1337-1345. (1998).
Tang, X. et al., "In vivo study on tissue engineered skeletal muscle with hypoglossal nerve implantation," Zhongguo Xiu Fu Chong Jian Wai Ke Za Zhi., vol. 26: 359-364 (2012) (Abstract only).
Tarnuzzer RW, et al., "Biochemical analysis of acute and chronic wound environments," Wound Repair Regen., vol. 4 (3):321-325 (1996).
Taylor, A.M., et al., "GDNF levels in the lower lip skin in a rat model of trigeminal neuropathic pain: implications for nonpeptidergic fiber reinnervation and parasympathetic sprouting," Pain, vol. 152: 1502-1510. (2011).
Tian, Y.Y., et al., "Favorable effects of VEGF gene transfer on a rat model of Parkinson disease using adeno-associated viral vectors," Neurosci Lett., vol. 421: 239-244 (2007).
Tokime, K., et al., "Enhanced production and secretion of glial cell line-derived neurotrophic factor and nerve growth factor from the skin in atopic dermatitis mouse model," Arch Dermatol Res., vol. 300: 343-352 (2008).
Tom, V.J., et al., "Combining peripheral nerve grafts and chondroitinase promotes functional axonal regeneration in the chronically injured spinal cord," J Neurosci ., vol. 29:14881-14890 (2009).
Trupp, M., et al., "Peripheral expression and biological activities of GDNF, a new neurotrophic factor for avian and mammalian peripheral neurons," J Cell Biol., vol. 130: 137-148 (1995).
Unezaki, S., et al, "Effects of neurotrophic factors on nerve regeneration monitored by in vivo imaging in thy1-YFP transgenic mice," J Neurosci Methods, vol. 178: 308-315 (2009).

(56) References Cited

OTHER PUBLICATIONS

Unezaki, S., et al. "Involvement of Tyr1472 phosphorylation of NMDA receptor NR2B subunit in postherpetic neuralgia in model mice," Mol Pain, vol. 8: 59 (2012).
Valacchi, G. et al., "Emergin Topics in Cutaneous Wound Repair," Ann. N.Y. Acad., Sci., 1259: 136-144 (2012).
Valdes-Sanchez, T., et al., BDNF is essentially required for the early postnatal survival of nociceptors, Dev Biol., vol. 339: 465-476. (2010).
Vauclair, S. et al., "Notch1 is essential for postnatal hair follicle development and homeostasis," Developmental Biology, vol. 284:184-193 (2005).
Vellani, V., et al., "Protease activated receptors 1 and 4 sensitize TRPV1 in nociceptive neurons," Mol Pain, vol. 6: 61 (2010).
Vellani, V., et al., "Sensitization of transient receptor potential vanilloid 1 by the prokineticin receptor agonist Bv8," J Neurosci., vol. 26: 5109-5116 (2006).
Wang, D., et al., "Preclinical anti-angiogenesis and anti-tumor activity of SIM010603, an oral, multi-targets receptor tyrosine kinases inhibitor," Cancer Chemother Pharmacol., vol. 69: 173-183 (2012).
Wang, S., et al. "Effects of the neurotrophic factor artemin on sensory afferent development and sensitivity," Sheng Li Xue Bao, vol. 60: 565-570 (2008).
Wang, T., et al., "Neurturin Overexpression in Skin Enhances Expression of TRPM8 in Cutaneous Sensory Neurons and Leads to Behavioral Sensitivity to Cool and Menthol," J Neurosci., vol. 33: 2060-2070 (2013).
Wang, T., et al., "Phenotypic switching of nonpeptidergic cutaneous sensory neurons following peripheral nerve injury," PLoS One, vol. 6: e28908 (2011).
Wei, D., et al., "Survival, synaptogenesis, and regeneration of adult mouse spiral ganglion neurons in vitro," Dev Neurobiol., vol. 67:108-122 (2007).
Wei, L., et al., "Transplantation of hypoxia preconditioned bone marrow mesenchymal stem cells enhances angiogenesis and neurogenesis after cerebral ischemia in rats," Neurobiol Dis., vol. 46: 635-645 (2012).
Weinkauf, B., et al.,."Local gene expression changes after UV-irradiation of human skin," PLoS One, vol. 7: e39411 (2012).
Werner S, et al., "Keratinocyte-fibroblast interactions in wound healing," J. Invest Dermatol., vol. 127(5):998-1008 (2007).
Werner S, et al., "Regulation of wound healing by growth factors and cytokines, "Physol Rev., vol. 83:835-870 (2003).
Wertheimer, E. "Diabetic skin complications: a need for reorganizing the categories of diabetes-associated complications," Isr Med Assoc J., vol. 6(5):287-289 (2004).
Whitney, J.D., "Overview: acute and chronic wounds," Nurs. Clin. North Am., vol. 40(2):191-205 (2005).

Wood, M.D., et al., "GDNF released from microspheres enhances nerve regeneration after delayed repair," Muscle Nerve, vol. 46: 122-124 (2012).
Xu, P., et al., "Activin induces tactile allodynia and increases calcitonin gene-related peptide after peripheral inflammation," J Neurosci., vol. 25: 9227-9235 (2005).
Yagi, M., et al., "Hair cell protection from aminoglycoside ototoxicity by adenovirus-mediated overexpression of glial cell line-derived neurotrophic factor," Hum Gene Ther., vol. 10:813-823 (1999).
Yagi, M., et al., "Spiral ganglion neurons are protected from degeneration by GDNF gene therapy," J Assoc Res Otolaryngol, vol. 1: 315-325 (2000).
Yamaguchi, Y., et al. "Cutaneous wound healing: an update," J Dermatol., vol. 28(10): 521-534: (2001).
Yamamoto, N., et al. "Expression and effects of glial cell line-derived neurotrophic factor on periodontal ligament cells," J Clin Periodontol., vol. 39: 556-564 (2012).
Yamasoba, T., et al., "Absence of hair cell protection by exogenous FGF-1 and FGF-2 delivered to guinea pig cochlea in vivo," Noise Health, vol. 3: 65-78 (2001).
Yamasoba, T., et al., "Attenuation of cochlear damage from noise trauma by an iron chelator, a free radical scavenger and glial cell line-derived neurotrophic factor in vivo," Brain Res., vol. 815: 317-325 (1999).
Yang, C. et al., "Distribution of GDNF family receptor alpha3 and RET in rat and human non-neural tissues," J Mol Histol., vol. 37(1-2):69-77. (2006).
Yang, W., et al., Synergetic protective effects of glial cell line-derived neurotrophic factor combined with neurotrophin-3 in F-actin on hair cell after noise trauma, Zhonghua Er Bi Yan Hou Ke Za Zhi, vol. 36: 342-345 (2001).
Ylikoski, J., et al., "Guinea pig auditory neurons are protected by glial cell line-derived growth factor from degeneration after noise trauma," Hear Res., vol. 124:17-26 (1998).
Yoon et al., "Induction of hair growth by insulin-like growth factor-1 in 1,763 MHz radiofrequency-irradiated hair follicle cells," PLoS One, vol. 6(12): e28474 (2011).
Yoshida, T., et al., "Hematopoietic stem cells prevent hair cell death after transient cochlear ischemia through paracrine effects," Neuroscience, vol. 145: 923-930 (2007).
Yoshida, T., et al., "Immunohistochemical localization of glial cell line-derived neurotrophic factor and its receptor Ret in the rat sweat gland," Kurume Med J. vol. 51: 193-202 (2004).
You, L., et al., "Glial cell-derived neurotrophic factor (GDNF)-induced migration and signal transduction in corneal epithelial cells," Invest Ophthalmol Vis Sci., vol. 42: 2496-2504 (2001).
Zhou, Z., et al. (2006). Dynamic changes in nerve growth factor and substance P in the murine hair cycle induced by depilation. J Dermatol 33, 833-841 (2006).
Zwick M., et al., "Glial cell line-derived neurotrophic factor is a survival factor for isolectin B4-positive, but not vanilloid receptor 1-positive, neurons in the mouse," J Neurosci., vol. 22: 4057-4065 (2002).

METHODS FOR PROMOTING WOUND HEALING AND HAIR GROWTH COMPRISING GDNF ADMINISTRATION

RELATED APPLICATIONS

This application is a continuation of US. application Ser. No. 17/373,877, filed Jul. 13, 2021, which is a continuation of US. application Ser. No. 16/452,459, filed Jun. 25, 2019, which is a divisional of US. application Ser. No. 14/775,386, filed Sep. 11, 2015, which is a national stage filing under 35 U.S.C. § 371 of International Application No. PCT/US2014/027419, filed Mar. 14, 2014, which was published under PCT Article 21(2) in English and claims the benefit of US. Provisional patent application Ser. No. 61/787,870, filed Mar. 15, 2013, each of which is incorporated by reference herein in its entirety.

REFERENCE TO AN ELECTRONIC SEQUENCE LISTING

The content of the electronic sequence listing (J022770106US05-SEQ-HJD.xml; Size: 52,716 bytes; and Date of Creation: Dec. 5, 2023) is herein incorporated by reference in its entirety.

BACKGROUND OF THE INVENTION

Adult organisms contain several types of cells with remarkable regenerative potential when provided with appropriate chemical or physical stimuli. Wound healing or wound repair is an example of a system where multiple biological pathways are activated during the regeneration of the entire tissue. Skin, the largest organ of the body self-renews throughout adult life. Hair follicles, described as the "bone marrow of the skin", are a source of numerous growth factors, cytokines and hormones that helps in remodeling the cutaneous environment (Schmidt-Ullrich and Paus (2005), BioEssays 27, 247-261). The role of several growth factors have been reported in the initiation of hair follicle development at embryonic stage but not much is known about their development in adult animals. The role of growth factors in skin biology, in particular, in wound repair or wound healing, has also been reported. However, the exact role of certain growth factors and cytokines in complex processes such as wound repair or wound healing and hair growth remains to be elucidated. Such understanding would greatly facilitate the development of such growth factors and cytokines as pharmaceutical and/or therapeutic agents useful in these complex processes.

SUMMARY OF THE INVENTION

The present invention is based, at least in part, on the discovery that the cytokine, glial cell line-derived growth factor (GDNF) plays unique roles in the complex processes of wound repair and hair growth. Accordingly, the present invention relates to various pharmaceutical and/or therapeutic methods that feature, in common, administration or delivery of glial cell line-derived growth factor (GDNF) as a biologic active agent. The invention is based, at least in part, on the discovery of several important biological activities of GDNF. In particular, the present inventors have discovered significant regulatory roles for GDNF in biological processes including wound healing and hair growth. Accordingly, in one aspect, the invention relates to methods of promoting wound healing, in particular cutaneous wound healing, wherein said methods feature administration of GDNF, or a biologically active fragment thereof, to a wound site of a subject, e.g., a human subject, in a dose and/or for a time period sufficient to promote wound healing. In particular, the GDNF, or biologically active fragment thereof, is administered in a dose and/or for a time sufficient to promote filling and re-epithelialization of a wound site. In a related aspect, the GDNF, or biologically active fragment thereof, is administered in a dose and/or for a time sufficient to promote reestablishment of a skin barrier at the wound site. In another aspect, the invention relates to methods of promoting hair growth on a subject, wherein said methods feature administration of GDNF, or a biologically active fragment thereof, at site of desired hair growth, in a dose and/or for a time sufficient to promote hair growth on the subject. In another aspect, the invention features pharmaceutical formulations that include a therapeutically effective dose of isolated GDNF, or a biologically active fragment thereof. In yet another aspect, the invention features kits that include said pharmaceutical formulations. In yet another aspect, the invention features the use of a therapeutically effective dose of GDNF, or a biologically active fragment thereof, for promoting wound healing at a wound site in a subject. In yet another aspect, the invention features the use of a pharmaceutically effective dose of GDNF, or a biologically active fragment thereof, for promoting hair growth at a desired site in a subject.

DETAILED DESCRIPTION OF THE INVENTION

Figure 1:
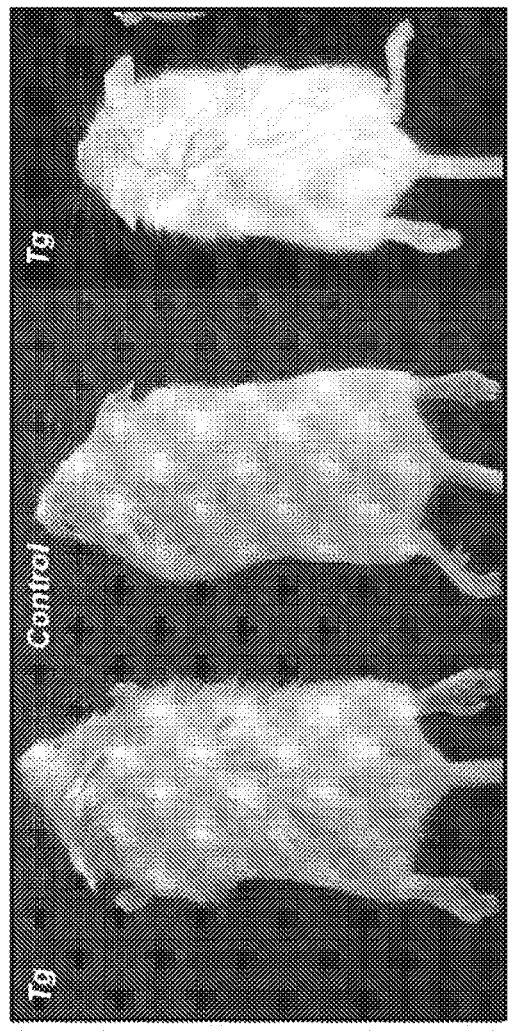
FIG. 1. Mice overexpressing Gdnf under the Cathespin L gene promoter have altered hair follicle development. FVB transgenic mice Tg(Ctsl-Gdnf) have ruffled fur by 3 wk of age (A). Skin sections stained with H&E from adult transgenic FVB mouse with more number of hair follicles adjacent to normal hair development (asterisk) compared to skin section from control littermate (B). The transgene overexpressing GDNF in B6C3H background mice also show multiple layers of hair follicles (C). Scale=100 μm.
Figure 1:
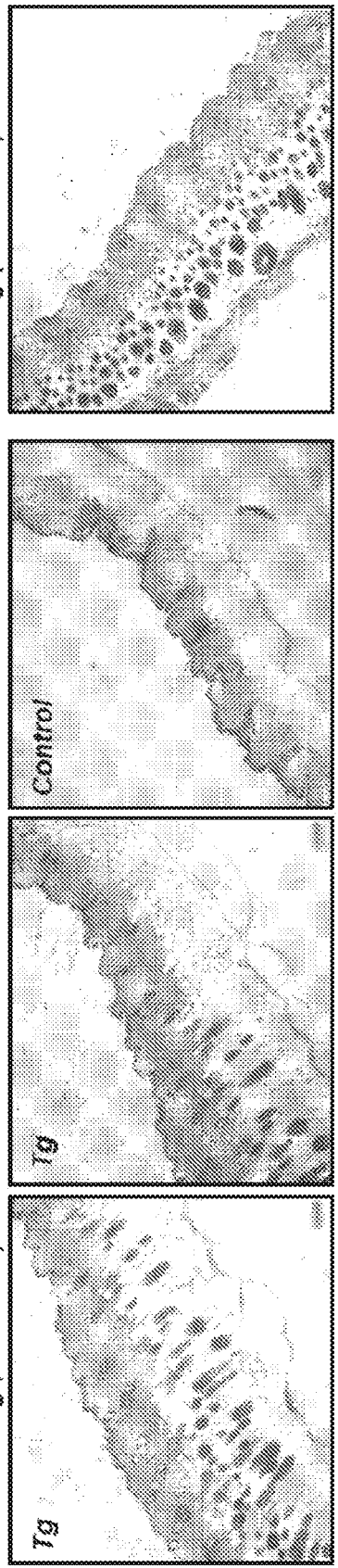
Figure 2:
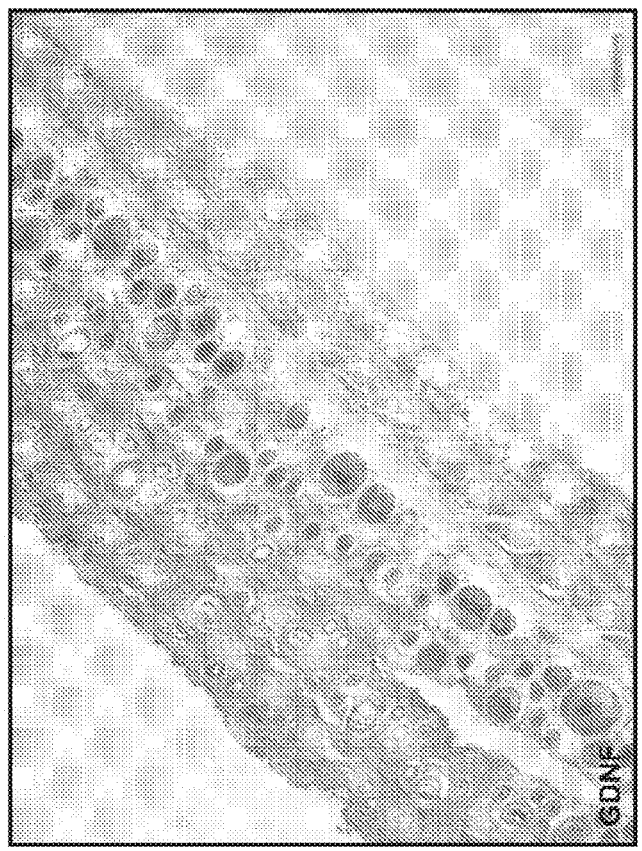
FIG. 2. Subcutaneous injection of recombinant GDNF in adult mice results in an increase in hair follicles. Images of skin sections from B6 wild type mice injected with 100 μl PBS or 10 μg GDNF on alternate days for two weeks. Scale=100 μm.
Figure 2:
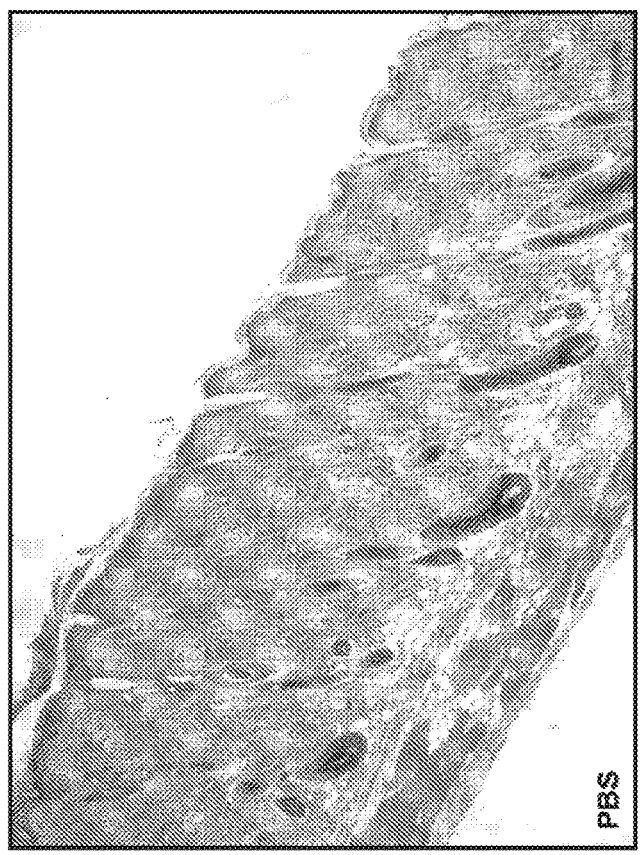

Glial Cell-Derived Neurotrophic Factor (GDNF) is a growth factor with 40% sequence homology to the TGFβ superfamily. First identified as survival factor for dopaminergic neurons of mid-brain and shown to be important for the development and maintenance of neural and other tissues (Lin et al 1993, Science 260, 1130-2). GDNF is part of complex that include the high affinity receptor tyrosine kinase, c-RET and glycosyphatidylinositol (GPI-) linked co-receptor, GFRα1 that activates specific signaling pathway leading to cell proliferation, survival, and other differentiation effects.

The present invention is based, at least in part, on the discovery of certain key regulatory roles for GDNF in complex processes including wound healing and hair growth. In initial experiments, the effect of GDNF on hair follicle growth was studied. For these studies, purified active recombinant protein expressed in baculovirus (as mammalian proteins expressed in baculovirus are glycosylated) was injected subcutaneously in mice and assayed for hair follicle growth. Preliminary results showed increase in number of hair follicles in mice injected with active form of GDNF compared to mice injected with PBS alone. This finding was very surprising, especially as the effect could be seen after a single injection.

The cutaneous wound healing process involves four steps, first the inflammatory phase followed by proliferative phase, the remodeling step and finally the epithelialization, when new skin is formed. During the proliferative phase extracellular matrix (ECM) components are synthesized and new blood vessels are formed on the matrix. Genes involved in the inflammatory response, angiogenesis and response to wounding were differentially expressed in tissues overexpressing Gdnf. Moreover, when GDNF was injected subcutaneously into mice, smoother skin was discovered. It was therefore predicted that GDNF influences the skin remodeling during wound healing. These findings, in addition to the detailed studies presented in the Examples Section, infra., lead the inventors to propose GDNF as novel factor for hair growth, wound healing, and treatment of scars, wrinkles (anti-aging), in particular, when the GDNF is applied topically to skin.

Prior to describing the invention, it may be helpful to an understanding thereof to set forth definitions of certain terms to be used hereinafter.

I. Definitions

The terms "homolog," "paralog," and "ortholog," have their art recognized meanings. Typically, a homolog of a given gene product is one of functional similarity as well as sequence similarity. If the homolog is derived from a different organism, the homolog may be referred to as the ortholog. If several homologs exist in a given organism, the homolog may be referred to as a paralog. Typically, the sequence similarity/identity between homologs is at least about 40%, 50%, 60%, 70%, 80%, 90%, or more (or a percentage falling within any interval or range of the foregoing). Methods for determining such similarity/identity are described, infra. Domains (e.g., TGFβ-like domains) conserved between homologs can have a sequence similarity/identity of at least about 70%, 80%, 90%, or more. It is understood that when comparing gene product sequence between diverse organisms, for example, flies and humans, sequence similarity between given homologs (e.g., orthologs) across the entire protein sequence may be low. However, if functional complementarity exists, and in addition, if conserved domains exist, e.g., TGFβ-like domains, then the gene products being compared can be considered homologs and thus selected as compositions for use in the methods of the invention, as described herein.

The term "bioactive fragment" includes any portion (e.g., a segment of contiguous amino acids) of a polypeptide, e.g., a GDNF polypeptide or ortholog thereof, sufficient to exhibit or exert at least activity of the polypeptide, e.g., at least one GDNF-associated activity including, for example, a growth promoting activity.

The phrase "encodes a gene product" includes the generation of a RNA molecule from a DNA molecule (i.e., a complementary RNA molecule generated from the DNA molecule by the process of transcription) and/or the generation of a polypeptide or protein molecule from an RNA (i.e., by the processes of transcription and translation).

The term "expression" of a gene or nucleic acid encompasses not only cellular gene expression, but also the transcription and translation of nucleic acid(s) in cloning systems and in any other context.

The term "subject", as used herein, includes living organisms. Examples of subjects include humans, monkeys, cows, sheep, goats, horses, camels, dogs, cats, mice, rats, and transgenic species thereof. Administration of the compositions of the present invention to a subject to be treated can be carried out using known procedures, at dosages and for periods of time effective to modulate hair growth and/or wound healing in the subject as further described herein.

As used herein, the term "isolated" molecule (e.g., isolated protein molecule or isolated peptide) refers to molecules which are substantially free of other cellular material, or culture medium when produced by recombinant techniques, or substantially free of chemical precursors or other chemicals when chemically synthesized.

The term "treatment", as used herein, is defined as the application or administration of a therapeutic agent to a subject, or application or administration of a therapeutic agent to an isolated tissue or cell line from a subject, who has a disease or disorder, a symptom of a disease or disorder, or a predisposition toward a disease or disorder, with the purpose to cure, heal, alleviate, relieve, alter, remedy, ameliorate, improve or affect the disease or disorder, the symptoms of the disease or disorder, or the predisposition toward a disease or disorder. A therapeutic agent includes, but is not limited to, GDNF peptides, proteins, protein fragments, peptidomimetics, and the like.

The term "effective amount", as used herein, is defined as that amount necessary or sufficient to treat or prevent a disorder. The "effective amount" can vary depending on such factors as the size and weight of the subject, the type of illness, or the particular agent being administered. One of ordinary skill in the art would be able to study the aforementioned factors and make the determination regarding the effective amount of the agent without undue experimentation.

The term "pharmaceutical composition" as used herein, refers to an agent formulated with one or more compatible solid or liquid filler diluents or encapsulating substances, which are suitable for administration to a human or lower animal.

The term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intra-synovial, intrasternal, intrathecal, intrahepatic, intralesional, and intracranial injections or infusion techniques. Typically, the treatment compositions of the present invention are administered topically or by subcutaneous injection.

A "suitable control" or "appropriate control" refers to any control or standard familiar to one of ordinary skill in the art useful for comparison purposes.

The term "cell" refers to any cell of a biological organism. Preferred cells are eukaryotic cells, including but not limited to, animal cells (e.g., mammalian cells, e.g., human or murine cells), nematode cells, plant cells, and yeast. The term includes cell lines, e.g., transformed mammalian cell lines as well as embryonic cells, e.g., embryonic stem cells. Eukaryotic cells responsive to GDNF, or eukaryotic cells involved in hair growth and/or wound repair are preferred cells of the invention. Also contemplated for use in the invention are prokaryotic cells, for use, for example, in methods of manufacturing proteins, e.g., GDNF.

The term "tissue" refers to a collection of cells, usually of different cell types, organized in a manner that imparts complex biological activity.

The term "cell extract" refers to a lysate or acellular preparation of a cell as defined above and can be a crude extract or partially purified as well as comprise additional agents such as recombinant polypeptides, nucleic acids, and/or buffers or stabilizers.

The term "organism" refers to multicellular organisms such as, e.g., *C. elegans, Drosophila*, mouse, and human.

The terms used herein are not intended to be limiting of the invention.

II. Glial Cell Line-Derived Neurotrophic Factor (GDNF)

Glial cell line-derived neurotrophic factor (or glial cell-derived neurotrophic factor) (GDNF), also known as ATF1, ATF2, HSCR3, and HFB1-GDNF is a distant member of the TGF-β superfamily. Glial-cell-line-derived neurotrophic factor (GDNF) was originally identified as a survival factor for midbrain dopaminergic neurons, and was able to prevent apoptosis of motor neurons induced by axotomy. GDNF and related ligands, neurturin (NRTN), artemin (ARTN) and persephin (PSPN), maintain several neuronal populations in the central nervous systems, including midbrain dopamine neurons and motorneurons. In addition, GDNF, NRTN and ARTN support the survival and regulate the differentiation of many peripheral neurons, including sympathetic, parasympathetic, sensory and enteric neurons. GDNF has further critical roles outside the nervous system in the regulation of kidney morphogenesis and spermatogenesis.

GDNF family ligands bind to specific GDNF family receptor alpha (GFRalpha) proteins, all of which form receptor complexes and signal through the RET receptor tyrosine kinase (the product of the c-ret (rearranged during transfection) protooncogene). The biological activity of GDNF is mediated by its corresponding high affinity receptor, GDNF family receptor a-1 (GFRα-1) which functions as part of a receptor complex with the intracellular-signaling component, RET. The mature form of the protein is considered a ligand for RET. GDNF also shows lower-affinity interactions with GFRα-2. The biology of GDNF signaling is much more complex than originally assumed. The neurotrophic effect of GDNF, except in motorneurons, requires the presence of TGF-β, which activates the transport of GFRα1 to the cell membrane. GDNF can also signal RET independently through GFR1α. Upon ligand binding, GDNF in complex with GFRα1 may interact with heparan sulphate glycosaminoglycans to activate the Met receptor tyrosine kinase through cytoplasmic Src-family kinases. GDNF family ligands also signal through the neural cell adhesion molecule NCAM. In cells lacking RET, GDNF binds with high affinity to the NCAM and GFRα1 complex, which activates Fyn and FAK.

This GDNF gene encodes a highly conserved neurotrophic factor. The encoded protein is processed to a mature secreted form that exists as a homodimer. Multiple transcript variants encoding different isoforms have been found for the human GDNF gene. Transcript variant (1) differs in the 5' UTR, representing use of an alternate promoter, and a downstream start codon, compared to variant 3. The resulting isoform (1) has a shorter N-terminus, compared to isoform 3. Transcript variant (2) also differs in the 5' UTR, and represents use of an alternate promoter, uses a downstream start codon, and uses an alternate in-frame splice site in the coding region, compared to variant 3. The resulting isoform (2) has a shorter N-terminus and lacks an internal segment, compared to isoform 3. Transcript variant (3) represents the longest transcript and encodes the longest isoform (3). Transcript Variant: This variant (4) uses an alternate in-frame splice site in the coding region, compared to variant 3. The resulting isoform (4) lacks an internal segment, compared to isoform 3.

The nucleic acids encoding the human GDNF isoforms are as follows:

>gi|299473777|ref|NM_000514.3| Homo sapiens glial cell derived
neurotrophic factor (GDNF) , transcript variant 1, mRNA (SEQ ID NO: 1)

CCGCCTCCAGCGCGCCCTTGCTGCCCCGCGCGACCCCAGGATTGCGAACTCTTGCCCCTGACCTGTTGGG

CGGGGCTCCGCGCTCCAGCCATCAGCCCGGATGGGTCTCCTGGCTGGGACTTGGGGCACCTGGAGTTAAT

GTCCAACCTAGGGTCTGCGGAGACCCGATCCGAGGTGCCGCCGCCGGACGGGACTTTAAGATGAAGTTAT

GGGATGTCGTGGCTGTCTGCCTGGTGCTGCTCCACACCGCGTCCGCCTTCCCGCTGCCCGCCGGTAAGAG

GCCTCCCGAGGCGCCCGCCGAAGACCGCTCCCTCGGCCGCCGCCGCGCGCCCTTCGCGCTGAGCAGTGAC

TCAAATATGCCAGAGGATTATCCTGATCAGTTCGATGATGTCATGGATTTTATTCAAGCCACCATTAAAA

GACTGAAAAGGTCACCAGATAAACAAATGGCAGTGCTTCCTAGAAGAGAGCGGAATCGGCAGGCTGCAGC

TGCCAACCCAGAGAATTCCAGAGGAAAAGGTCGGAGAGGCCAGAGGGGCAAAAACCGGGGTTGTGTCTTA

ACTGCAATACATTTAAATGTCACTGACTTGGGTCTGGGCTATGAAACCAAGGAGGAACTGATTTTTAGGT

ACTGCAGCGGCTCTTGCGATGCAGCTGAGACAACGTACGACAAAATATTGAAAAACTTATCCAGAAATAG

AAGGCTGGTGAGTGACAAAGTAGGGCAGGCATGTTGCAGACCCATCGCCTTTGATGATGACCTGTCGTTT

TTAGATGATAACCTGGTTTACCATATTCTAAGAAAGCATTCCGCTAAAAGGTGTGGATGTATCTGACTCC

GGCTCCAGAGACTGCTGTGTATTGCATTCCTGCTACAGTGCAAAGAAAGGGACCAAGGTTCCCAGGAAAT

GTTTGCCCAGAATGGAAGATGAGGACCAAGGAGGCGGAGGAGGAGGAAGAAGAAGAGGAGGAGGAGGAGG

AGGAGGAGGAGGAGGAAGGCAGCCATCATGGGAGCCTGGTAGAGGGAGATCCAGCTACAGACAACTG

GACAGGAGAGAGAAAACAGCCCTCTGGATTCTCCAGGATGGCAGCCGATGTCACTAGAAGCTCAGGGC

TGATGTTCCTGGTTGGCTATTGCCACCATTTCAGCTGATACAGTCCACCATCACTGATTACCGGCGCGGT

TGCGGTGGATGCACTTGAACCAAACCAGTGTATCTCCTGTGATTTGTTTTCATGTGTCCGAAGACACCAG

GGAAACAGAGATCCTGGTGTTGTTCCTTGTTATTACGTTTTACTGCTGAAAGTAAGAGGTTTATTTTTCT

GTCACTCAGTGGAGACATACCCTGGAAAGGAGAGGGGAAAAAAAAAGCAAAGATACAAGAGATAATCACC

TTTGCATTTGAAAGTTGAGGCCCGAGGTTTACTACAACCAGCATTTTGCCAACGGTTGGTGATTGATTT

CCATCACGGTGTGTGGGGTGGGAAGAAGTTGGCTAGGAACCAAAAAGGCTGTGCTCATGATTAAACACAA

ACCTGAAGGTATTTCCTTTATGTCCTTGGAAACAGGAAACGAGTTGTGGTTTTCGCCAGCATTCTTGTAG

GAGAGAATCGGGGAAGGCCCCGAACTGCCCCCGGGCAGGGAGAGCCCCTCAGGCCTGTTGGTTTACAGAG

AGACAGATGTTACATAACCAGCTCCGTTGATGCGTGGTCACCAGTGACCAGAGAAGCTACTCGATGCAAT

GCATCTGTTTCAGATACAGAAATATAGAGAAGATATTTATTGAAATTTAAGTTATTGTTATTTATTACCG

TTCACTAATGAATTTCTCTTTTTTCCCTTATTTATTAAAGTTTCTTTTCAAAGGTGCCAAAGTATATGTG

CTCGCAAAATGCAAAGAAAGGTGACAAAAGGAAATTTGAATTGGGAACAAGGGTCCATGCTTTTCAAAGT

ATTAAAAAGTTTTTTGCCAGGCAAAAATCACTTACTTTACCTTTTTAAGAAAATTTGTCATTAATTTTCC

CCAGATTTCAGCATTTTTCCCAATTTTTATTTGTGGAGCATCTCAGGCAAGCCCCCTTTCCTGGAGCAGC

GTGCAGAGACCACTGGCACTTGACTTTATTTCTTCCTTGCTCCATTGCTGAACAGAAATGTCGTGGGCTC

CACTTCCTGTTGTCTTTAAGCTCTTAGTCCCCTCCACGTATACCTATCTGTACTATGCATAACCATATGT

AGAAAAGGTTCAGTTCCTTTTAGTAGGTAGTCCTGGATTTAATGCTGACCTAAAAGTAATGTCGACAATG

CTGTCAGGTAGCTGCCGTTCTACCGACTCCCTCCATCCCTGCCCACCCACTGCCCTCCCGAGAATATGCT

GGCTGCCCAGTGCAGCCCGGGAGACACAGGGGCCTTCCAGAGGTAGGGTCTACCAGGTCCTGTACAACCC

CTGGGCTGTCACCGGGGGTCAACAGCTGCTGCTCCTATATACCCAAACACCTGACAGCTCCCTGGGGAGC

AGATGGCTGAGAAGGGTGCTGAGGAAGCCATATTGGGACCAGCCACAGCCACACACATGGAGCCTCATAC

TTAGGAGCGTGCTGCCTTTAAATGAAGGTGGTCGGGGCCAGTGCAGCGGCTCACACCCATAATCCCAACA

-continued

```
CTTTGGAAAGCCAAGGTGGGAGGATCTCTTGAACCCAGGAGTTTGAGACCAGCTTGGGCAACATAGGGAG

ACCCTGTCTCTACAGAAACTTTAAAAATTAGGCAGGCATGATGGTGCACACCTGTGGTCCCAGCTACTCA

AGAGGCTGAAGGAGGATCACTTGAGTCCAGAAGGTCGAGGCTGCAGTGAGCTGTGATCATGCCACTGCAC

TCCAGCCTAAGTGACAGTGCGGTACCCTGTCTCAAAAAAAAAAAAAAAAAAAAAAAGAGGTTGGAGCAGG

AGGAAGCATAGGGGCGGGAACAGCCACCTCCTCCATGCCCTAGATTGTGAATTTATCGGGCAGCCAACAC

ATGTATGACACACTAGGCCCTGTATTACAGCTTGTTACGCATTTCATAAAAGGGATTTTCATTAAGGAGA

TAATCTATTACTACCTTAGTGGCTACTAGTATAAAACTATGACAGATTTAGCAATTAAATGAAATA

CTGGCCTCCATCAAATAATCATAGTAACAAGAAGCAGCAGTTACCAGACATCTGATCCCCTTCCCCCAAA

ATACCCAAATTCTTCATGGTTCTGCCCTTCTCTGTCCTTTCTGCTCCCCTTGCTCGCCTGGGAAATGGAG

GAAAGGCCTTCCCTCTCACACTGTCTTGGGATCTTGCTGAGAATTCAGACTGCTCGAAACAGTGACAAAC

CCCAGCCATCCAGTCATTCGTGGAGCACAATTTGGATGTGGCCCCAGGGGCATCTGTCCCATTCAGAGAA

CCTTGGCAGTGCGATGGCCACTGTTCCCAGGCTTCAACCTCAGTGACCCCCCCAACAACTCCCCATGGA

GAGTCCCTGCCCAAAAAAGCTGTAGGATCCAAGGGGTGTCAATAGCTCGTTCCCGGCATCACCTACACAC

CACAAGCAGGTTTTAATGGAAGCAAGTTGCTCCACCAAATCCACAAAAGGGTAAAGTTTGTGATTTTTCT

TTATCATTGCGATCACCATCTGATACCGTAAGGAGTGCACTTGTTTGGAAGTTCTGACTTCTCTGATCTG

TCTTGGTCGTTTGTGTTATAAAACCAAAGTTCTCTACAGACTTTATTTTTGTACAATATCATTTTGTAAC

TTTTTACAAATAAAAACTCATTTCTATTGC

>gi|299473776|ref|NM_199231.2| Homo sapiens glial cell derived
neurotrophic factor (GDNF), transcript variant 2, mRNA
                                                       (SEQ ID NO: 2)
CATACAGGCCAAAAGTCTCCAAGTCCCTGCTAACTTCTTGCTCTCGCAACAGAATACCTATTTAGGTGGG

AAGAATGAGGTGTGGGCGGCAGGCTGGGTGCCGCCGCCGGACGGGACTTTAAGATGAAGTTATGGGATGT

CGTGGCTGTCTGCCTGGTGCTGCTCCACACCGCGTCCGCCTTCCCGCTGCCCGCCGCAAATATGCCAGAG

GATTATCCTGATCAGTTCGATGATGTCATGGATTTTATTCAAGCCACCATTAAAAGACTGAAAAGGTCAC

CAGATAAACAAATGGCAGTGCTTCCTAGAAGAGAGCGGAATCGGCAGGCTGCAGCTGCCAACCCAGAGAA

TTCCAGAGGAAAAGGTCGGAGAGGCCAGAGGGGCAAAAACCGGGGTTGTGTCTTAACTGCAATACATTTA

AATGTCACTGACTTGGGTCTGGGCTATGAAACCAAGGAGGAACTGATTTTTAGGTACTGCAGCGGCTCTT

GCGATGCAGCTGAGACAACGTACGACAAAATATTGAAAAACTTATCCAGAAATAGAAGGCTGGTGAGTGA

CAAAGTAGGGCAGGCATGTTGCAGACCCATCGCCTTTGATGATGACCTGTCGTTTTAGATGATAACCTG

GTTTACCATATTCTAAGAAAGCATTCCGCTAAAAGGTGTGGATGTATCTGACTCCGGCTCCAGAGACTGC

TGTGTATTGCATTCCTGCTACAGTGCAAAGAAAGGGACCAAGGTTCCCAGGAAATGTTTGCCCAGAATGG

AAGATGAGGACCAAGGAGGCGGAGGAGGAGGAAGAAGAAGAGGAGGAGGAGGAGGAGGAGGAGGAGGAGG

AGGAAGGCAGCCATCATGGGAGCCTGGTAGAGGGAGATCCAGCTACAGACAACTGGACAGGAGAGAGAGA

AAACAGCCCTCTGGATTCTCCAGGATGGCAGCCGATGTCACTAGAAGCTCAGGGCTGATGTTCCTGGTTG

GCTATTGCCACCATTTCAGCTGATACAGTCCACCATCACTGATTACCGGCGCGGTTGCGGTGGATGCACT

TGAACCAAACCAGTGTATCTCCTGTGATTTGTTTTCATGTGTCCGAAGACACCAGGGAAACAGAGATCCT

GGTGTTGTTCCTTGTTATTACGTTTTACTGCTGAAAGTAAGAGGTTTATTTTTCTGTCACTCAGTGGAGA

CATACCCTGGAAAGGAGAGGGAAAAAAAAGCAAAGATACAAGAGATAATCACCTTTGCATTTGAAAGT

TGAGGCCCGAGGTTTACTACAACCAGCATTTTGCCAACGGTTGGTGATTGATTTCCATCACGGTGTGTG

GGGTGGGAAGAAGTTGGCTAGGAACCAAAAAGGCTGTGCTCATGATTAAACACAAACCTGAAGGTATTTC

CTTTATGTCCTTGGAAACAGGAAACGAGTTGTGGTTTTCGCCAGCATTCTTGTAGGAGAGAATCGGGGAA

GGCCCCGAACTGCCCCCGGGCAGGGAGAGCCCCTCAGGCCTGTTGGTTTACAGAGAGACAGATGTTACAT
```

-continued

```
AACCAGCTCCGTTGATGCGTGGTCACCAGTGACCAGAGAAGCTACTCGATGCAATGCATCTGTTTCAGAT
ACAGAAATATAGAGAAGATATTTATTGAAATTTAAGTTATTGTTATTTATTACCGTTCACTAATGAATTT
CTCTTTTTTCCCTTATTTATTAAAGTTTCTTTTCAAAGGTGCCAAAGTATATGTGCTCGCAAAATGCAAA
GAAAGGTGACAAAAGGAAATTTGAATTGGGAACAAGGGTCCATGCTTTTCAAAGTATTAAAAAGTTTTTT
GCCAGGCAAAAATCACTTACTTTACCTTTTTAAGAAAATTTGTCATTAATTTTCCCCAGATTTCAGCATT
TTTCCCAATTTTTATTTGTGGAGCATCTCAGGCAAGCCCCCTTTCCTGGAGCAGCGTGCAGAGACCACTG
GCACTTGACTTTATTTCTTCCTTGCTCCATTGCTGAACAGAAATGTCGTGGGCTCCACTTCCTGTTGTCT
TTAAGCTCTTAGTCCCCTCCACGTATACCTATCTGTACTATGCATAACCATATGTAGAAAAGGTTCAGTT
CCTTTTAGTAGGTAGTCCTGGATTTAATGCTGACCTAAAAGTAATGTCGACAATGCTGTCAGGTAGCTGC
CGTTCTACCGACTCCCTCCATCCCTGCCCACCCACTGCCCTCCCGAGAATATGCTGGCTGCCCAGTGCAG
CCCGGGAGACACAGGGGCCTTCCAGAGGTAGGGTCTACCAGGTCCTGTACAACCCCTGGGCTGTCACCGG
GGGTCAACAGCTGCTGCTCCTATATACCCAAACACCTGACAGCTCCCTGGGGAGCAGATGGCTGAGAAGG
GTGCTGAGGAAGCCATATTGGGACCAGCCACAGCCACACACATGGAGCCTCATACTTAGGAGCGTGCTGC
CTTTAAATGAAGGTGGTCGGGGCCAGTGCAGCGGCTCACACCCATAATCCCAACACTTTGGAAAGCCAAG
GTGGGAGGATCTCTTGAACCCAGGAGTTTGAGACCAGCTTGGGCAACATAGGGAGACCCTGTCTCTACAG
AAACTTTAAAAATTAGGCAGGCATGATGGTGCACACCTGTGGTCCCAGCTACTCAAGAGGCTGAAGGAGG
ATCACTTGAGTCCAGAAGGTCGAGGCTGCAGTGAGCTGTGATCATGCCACTGCACTCCAGCCTAAGTGAC
AGTGCGGTACCCTGTCTCAAAAAAAAAAAAAAAAAAAAAAAGAGGTTGGAGCAGGAGGAAGCATAGGGGC
GGGAACAGCCACCTCCTCCATGCCCTAGATTGTGAATTTATCGGGCAGCCAACACATGTATGACACACTA
GGCCCTGTATTACAGCTTGTTACGCATTTCATAAAAGGGATTTTCATTAAGGAGATAATCTATTACTACC
TACCTTAGTGGCTACTAGTATAAAACTATGACAGATTTAGCAATTAAATGAAATACTGGCCTCCATCAAA
TAATCATAGTAACAAGAAGCAGCAGTTACCAGACATCTGATCCCCTTCCCCCAAAATACCCAAATTCTTC
ATGGTTCTGCCCTTCTCTGTCCTTTCTGCTCCCCTTGCTCGCCTGGGAAATGGAGGAAAGGCCTTCCCTC
TCACACTGTCTTGGGATCTTGCTGAGAATTCAGACTGCTCGAAACAGTGACAAACCCCAGCCATCCAGTC
ATTCGTGGAGCACAATTTGGATGTGGCCCCAGGGGCATCTGTCCCATTCAGAGAACCTTGGCAGTGCGAT
GGCCACTGTTCCCAGGCTTCAACCTCAGTGACCCCCCCCAACAACTCCCCATGGAGAGTCCCTGCCCAAA
AAAGCTGTAGGATCCAAGGGGTGTCAATAGCTCGTTCCCGGCATCACCTACACACCACAAGCAGGTTTTA
ATGGAAGCAAGTTGCTCCACCAAATCCACAAAAGGGTAAAGTTTGTGATTTTTCTTTATCATTGCGATCA
CCATCTGATACCGTAAGGAGTGCACTTGTTTGGAAGTTCTGACTTCTCTGATCTGTCTTGGTCGTTTGTG
TTATAAAACCAAAGTTCTCTACAGACTTTATTTTTGTACAATATCATTTTGTAACTTTTTACAAATAAAA
ACTCATTTCTATTGC
```

>gi|299473778|ref|NM_001190468.1| *Homo sapiens* glial cell derived neurotrophic factor (GDNF), transcript variant 3, mRNA (SEQ ID NO: 3)

```
CCAAAGCGTCCGAGACTGGGTACAGTCGTCCAGGCGTGACGGGGCGCGGGGAGCCAGTGACTCCTCTGG
GAGGGGAAGGGATTAGGGCCAGAATCTCTCAAAGGTGCAAAAATCCAGTCAAGAGAGGGTTTTCGGGTAT
ACCACGGAGGATTAAAACTTTCAAGACAAATGCAGTCTTTGCCTAACAGCAATGGTGCCGCCGCCGGACG
GGACTTTAAGATGAAGTTATGGGATGTCGTGGCTGTCTGCCTGGTGCTGCTCCACACCGCGTCCGCCTTC
CCGCTGCCCGCCGGTAAGAGGCCTCCCGAGGCGCCCGCCGAAGACCGCTCCCTCGGCCGCCGCCGCGCGC
CCTTCGCGCTGAGCAGTGACTCAAATATGCCAGAGGATTATCCTGATCAGTTCGATGATGTCATGGATTT
TATTCAAGCCACCATTAAAAGACTGAAAAGGTCACCAGATAAACAAATGGCAGTGCTTCCTAGAAGAGAG
CGGAATCGGCAGGCTGCAGCTGCCAACCCAGAGAATTCCAGAGGAAAAGGTCGGAGAGGCCAGAGGGGCA
```

-continued

```
AAAACCGGGGTTGTGTCTTAACTGCAATACATTTAAATGTCACTGACTTGGGTCTGGGCTATGAAACCAA

GGAGGAACTGATTTTTAGGTACTGCAGCGGCTCTTGCGATGCAGCTGAGACAACGTACGACAAAATATTG

AAAAACTTATCCAGAAATAGAAGGCTGGTGAGTGACAAAGTAGGGCAGGCATGTTGCAGACCCATCGCCT

TTGATGATGACCTGTCGTTTTAGATGATAACCTGGTTTACCATATTCTAAGAAAGCATTCCGCTAAAAG

GTGTGGATGTATCTGACTCCGGCTCCAGAGACTGCTGTGTATTGCATTCCTGCTACAGTGCAAAGAAAGG

GACCAAGGTTCCCAGGAAATGTTTGCCCAGAATGGAAGATGAGGACCAAGGAGGCGGAGGAGGAGGAAGA

AGAAGAGGAGGAGGAGGAGGAGGAGGAGGAGGAGGAAGGCAGCCATCATGGGAGCCTGGTAGAGGGA

GATCCAGCTACAGACAACTGGACAGGAGAGAGAGAAAACAGCCCTCTGGATTCTCCAGGATGGCAGCCGA

TGTCACTAGAAGCTCAGGGCTGATGTTCCTGGTTGGCTATTGCCACCATTTCAGCTGATACAGTCCACCA

TCACTGATTACCGGCGCGGTTGCGGTGGATGCACTTGAACCAAACCAGTGTATCTCCTGTGATTTGTTTT

CATGTGTCCGAAGACACCAGGGAAACAGAGATCCTGGTGTTGTTCCTTGTTATTACGTTTTACTGCTGAA

AGTAAGAGGTTTATTTTTCTGTCACTCAGTGGAGACATACCCTGGAAAGGAGAGGGGAAAAAAAAAGCAA

AGATACAAGAGATAATCACCTTTGCATTTGAAAGTTGAGGCCCGAGGTTTACTACAACCAGCATTTTTGC

CAACGGTTGGTGATTGATTTCCATCACGGTGTGTGGGGTGGGAAGAAGTTGGCTAGGAACCAAAAAGGCT

GTGCTCATGATTAAACACAAACCTGAAGGTATTTCCTTTATGTCCTTGGAAACAGGAAACGAGTTGTGGT

TTTCGCCAGCATTCTTGTAGGAGAGAATCGGGGAAGGCCCCGAACTGCCCCCGGGCAGGGAGAGCCCCTC

AGGCCTGTTGGTTTACAGAGAGACAGATGTTACATAACCAGCTCCGTTGATGCGTGGTCACCAGTGACCA

GAGAAGCTACTCGATGCAATGCATCTGTTTCAGATACAGAAATATAGAGAAGATATTTATTGAAATTTAA

GTTATTGTTATTTATTACCGTTCACTAATGAATTTCTCTTTTTTCCCTTATTTATTAAAGTTTCTTTTCA

AAGGTGCCAAAGTATATGTGCTCGCAAAATGCAAAGAAAGGTGACAAAAGGAAATTTGAATTGGGAACAA

GGGTCCATGCTTTTCAAAGTATTAAAAAGTTTTTTGCCAGGCAAAAATCACTTACTTTACCTTTTTAAGA

AAATTTGTCATTAATTTTCCCCAGATTTCAGCATTTTTCCCAATTTTTATTTGTGGAGCATCTCAGGCAA

GCCCCCTTTCCTGGAGCAGCGTGCAGAGACCACTGGCACTTGACTTTATTTCTTCCTTGCTCCATTGCTG

AACAGAAATGTCGTGGGCTCCACTTCCTGTTGTCTTTAAGCTCTTAGTCCCCTCCACGTATACCTATCTG

TACTATGCATAACCATATGTAGAAAAGGTTCAGTTCCTTTTAGTAGGTAGTCCTGGATTTAATGCTGACC

TAAAAGTAATGTCGACAATGCTGTCAGGTAGCTGCCGTTCTACCGACTCCCTCCATCCCTGCCCACCCAC

TGCCCTCCCGAGAATATGCTGGCTGCCCAGTGCAGCCCGGGAGACACAGGGGCCTTCCAGAGGTAGGGTC

TACCAGGTCCTGTACAACCCCTGGGCTGTCACCGGGGGTCAACAGCTGCTGCTCCTATATACCCAAACAC

CTGACAGCTCCCTGGGGAGCAGATGGCTGAGAAGGGTGCTGAGGAAGCCATATTGGGACCAGCCACAGCC

ACACACATGGAGCCTCATACTTAGGAGCGTGCTGCCTTTAAATGAAGGTGGTCGGGGCCAGTGCAGCGGC

TCACACCCATAATCCCAACACTTTGGAAAGCCAAGGTGGGAGGATCTCTTGAACCCAGGAGTTTGAGACC

AGCTTGGGCAACATAGGGAGACCCTGTCTCTACAGAAACTTTAAAAATTAGGCAGGCATGATGGTGCACA

CCTGTGGTCCCAGCTACTCAAGAGGCTGAAGGAGGATCACTTGAGTCCAGAAGGTCGAGGCTGCAGTGAG

CTGTGATCATGCCACTGCACTCCAGCCTAAGTGACAGTGCGGTACCCTGTCTCAAAAAAAAAAAAAAAA

AAAAAAGAGGTTGGAGCAGGAGGAAGCATAGGGGCGGGAACAGCCACCTCCTCCATGCCCTAGATTGTGA

ATTTATCGGGCAGCCAACACATGTATGACACACTAGGCCCTGTATTACAGCTTGTTACGCATTTCATAAA

AGGGATTTTCATTAAGGAGATAATCTATTACTACCTACCTTAGTGGCTACTAGTATAAAACTATGACAGA

TTTAGCAATTAAATGAAATACTGGCCTCCATCAAATAATCATAGTAACAAGAAGCAGCAGTTACCAGACA

TCTGATCCCCTTCCCCCAAAATACCCAAATTCTTCATGGTTCTGCCCTTCTCTGTCCTTTCTGCTCCCCT

TGCTCGCCTGGGAAATGGAGGAAAGGCCTTCCCTCTCACACTGTCTTGGGATCTTGCTGAGAATTCAGAC
```

-continued

TGCTCGAAACAGTGACAAACCCCAGCCATCCAGTCATTCGTGGAGCACAATTTGGATGTGGCCCCAGGGG

CATCTGTCCCATTCAGAGAACCTTGGCAGTGCGATGGCCACTGTTCCCAGGCTTCAACCTCAGTGACCCC

CCCCAACAACTCCCCATGGAGAGTCCCTGCCCAAAAAAGCTGTAGGATCCAAGGGGTGTCAATAGCTCGT

TCCCGGCATCACCTACACACCACAAGCAGGTTTTAATGGAAGCAAGTTGCTCCACCAAATCCACAAAAGG

GTAAAGTTTGTGATTTTTCTTTATCATTGCGATCACCATCTGATACCGTAAGGAGTGCACTTGTTTGGAA

GTTCTGACTTCTCTGATCTGTCTTGGTCGTTTGTGTTATAAAACCAAAGTTCTCTACAGACTTTATTTTT

GTACAATATCATTTTGTAACTTTTTACAAATAAAAACTCATTTCTATTGC

>gi|299473780|ref|NM_001190469.1| *Homo sapiens* glial cell derived
neurotrophic factor (GDNF), transcript variant 4, mRNA (SEQ ID NO: 4)

CCAAAGCGTCCGAGACTGGGTACAGTCGTCCAGGCGTGACGGGGCGCGGGGAGCCAGTGACTCCTCTGG

GAGGGGAAGGGATTAGGGCCAGAATCTCTCAAAGGTGCAAAAATCCAGTCAAGAGAGGGTTTTCGGGTAT

ACCACGGAGGATTAAAACTTTCAAGACAAATGCAGTCTTTGCCTAACAGCAATGGTGCCGCCGCCGGACG

GGACTTTAAGATGAAGTTATGGGATGTCGTGGCTGTCTGCCTGGTGCTGCTCCACACCGCGTCCGCCTTC

CCGCTGCCCGCCGCAAATATGCCAGAGGATTATCCTGATCAGTTCGATGATGTCATGGATTTTATTCAAG

CCACCATTAAAAGACTGAAAAGGTCACCAGATAAACAAATGGCAGTGCTTCCTAGAAGAGAGCGGAATCG

GCAGGCTGCAGCTGCCAACCCAGAGAATTCCAGAGGAAAAGGTCGGAGAGGCCAGAGGGGCAAAAACCGG

GGTTGTGTCTTAACTGCAATACATTTAAATGTCACTGACTTGGGTCTGGGCTATGAAACCAAGGAGGAAC

TGATTTTTAGGTACTGCAGCGGCTCTTGCGATGCAGCTGAGACAACGTACGACAAAATATTGAAAAACTT

ATCCAGAAATAGAAGGCTGGTGAGTGACAAAGTAGGGCAGGCATGTTGCAGACCCATCGCCTTTGATGAT

GACCTGTCGTTTTTAGATGATAACCTGGTTTACCATATTCTAAGAAAGCATTCCGCTAAAAGGTGTGGAT

GTATCTGACTCCGGCTCCAGAGACTGCTGTGTATTGCATTCCTGCTACAGTGCAAAGAAAGGGACCAAGG

TTCCCAGGAAATGTTTGCCCAGAATGGAAGATGAGGACCAAGGAGGCGGAGGAGGAGGAAGAAGAAGAGG

AGGAGGAGGAGGAGGAGGAGGAGGAGGAAGGCAGCCATCATGGGAGCCTGGTAGAGGGAGATCCAGC

TACAGACAACTGGACAGGAGAGAGAGAAAACAGCCCTCTGGATTCTCCAGGATGGCAGCCGATGTCACTA

GAAGCTCAGGGCTGATGTTCCTGGTTGGCTATTGCCACCATTTCAGCTGATACAGTCCACCATCACTGAT

TACCGGCGCGGTTGCGGTGGATGCACTTGAACCAAACCAGTGTATCTCCTGTGATTTGTTTTCATGTGTC

CGAAGACACCAGGGAAACAGAGATCCTGGTGTTGTTCCTTGTTATTACGTTTTACTGCTGAAAGTAAGAG

GTTTATTTTTCTGTCACTCAGTGGAGACATACCCTGGAAAGGAGAGGGGAAAAAAAAAGCAAAGATACAA

GAGATAATCACCTTTGCATTTGAAAGTTGAGGCCCGAGGTTTACTACAACCAGCATTTTTGCCAACGGTT

GGTGATTGATTTCCATCACGGTGTGTGGGGTGGGAAGAAGTTGGCTAGGAACCAAAAAGGCTGTGCTCAT

GATTAAACACAAACCTGAAGGTATTTCCTTTATGTCCTTGGAAACAGGAAACGAGTTGTGGTTTTCGCCA

GCATTCTTGTAGGAGAGAATCGGGGAAGGCCCCGAACTGCCCCCGGGCAGGGAGAGCCCCTCAGGCCTGT

TGGTTTACAGAGAGACAGATGTTACATAACCAGCTCCGTTGATGCGTGGTCACCAGTGACCAGAGAAGCT

ACTCGATGCAATGCATCTGTTTCAGATACAGAAATATAGAGAAGATATTTATTGAAATTTAAGTTATTGT

TATTTATTACCGTTCACTAATGAATTTCTCTTTTTTCCCTTATTTATTAAAGTTTCTTTTCAAGGTGCC

AAAGTATATGTGCTCGCAAAATGCAAAGAAAGGTGACAAAAGGAAATTTGAATTGGGAACAAGGGTCCAT

GCTTTTCAAAGTATTAAAAAGTTTTTTGCCAGGCAAAAATCACTTACTTTACCTTTTTAAGAAAATTTGT

CATTAATTTTCCCCAGATTTCAGCATTTTTCCCAATTTTTATTTGTGGAGCATCTCAGGCAAGCCCCCTT

TCCTGGAGCAGCGTGCAGAGACCACTGGCACTTGACTTTATTTCTTCCTTGCTCCATTGCTGAACAGAAA

TGTCGTGGGCTCCACTTCCTGTTGTCTTTAAGCTCTTAGTCCCCTCCACGTATACCTATCTGTACTATGC

ATAACCATATGTAGAAAAGGTTCAGTTCCTTTTAGTAGGTAGTCCTGGATTTAATGCTGACCTAAAAGTA

```
ATGTCGACAATGCTGTCAGGTAGCTGCCGTTCTACCGACTCCCTCCATCCCTGCCCACCCACTGCCCTCC

CGAGAATATGCTGGCTGCCCAGTGCAGCCCGGGAGACACAGGGGCCTTCCAGAGGTAGGGTCTACCAGGT

CCTGTACAACCCCTGGGCTGTCACCGGGGGTCAACAGCTGCTGCTCCTATATACCCAAACACCTGACAGC

TCCCTGGGGAGCAGATGGCTGAGAAGGGTGCTGAGGAAGCCATATTGGGACCAGCCACAGCCACACACAT

GGAGCCTCATACTTAGGAGCGTGCTGCCTTTAAATGAAGGTGGTCGGGGCCAGTGCAGCGGCTCACACCC

ATAATCCCAACACTTTGGAAAGCCAAGGTGGGAGGATCTCTTGAACCCAGGAGTTTGAGACCAGCTTGGG

CAACATAGGGAGACCCTGTCTCTACAGAAACTTTAAAAATTAGGCAGGCATGATGGTGCACACCTGTGGT

CCCAGCTACTCAAGAGGCTGAAGGAGGATCACTTGAGTCCAGAAGGTCGAGGCTGCAGTGAGCTGTGATC

ATGCCACTGCACTCCAGCCTAAGTGACAGTGCGGTACCCTGTCTCAAAAAAAAAAAAAAAAAAAAAAAGA

GGTTGGAGCAGGAGGAAGCATAGGGGCGGGAACAGCCACCTCCTCCATGCCCTAGATTGTGAATTTATCG

GGCAGCCAACACATGTATGACACACTAGGCCCTGTATTACAGCTTGTTACGCATTTCATAAAAGGGATTT

TCATTAAGGAGATAATCTATTACTACCTACCTTAGTGGCTACTAGTATAAAACTATGACAGATTTAGCAA

TTAAATGAAATACTGGCCTCCATCAAATAATCATAGTAACAAGAAGCAGCAGTTACCAGACATCTGATCC

CCTTCCCCCAAAATACCCAAATTCTTCATGGTTCTGCCCTTCTCTGTCCTTTCTGCTCCCCTTGCTCGCC

TGGGAAATGGAGGAAAGGCCTTCCCTCTCACACTGTCTTGGGATCTTGCTGAGAATTCAGACTGCTCGAA

ACAGTGACAAACCCCAGCCATCCAGTCATTCGTGGAGCACAATTTGGATGTGGCCCCAGGGGCATCTGTC

CCATTCAGAGAACCTTGGCAGTGCGATGGCCACTGTTCCCAGGCTTCAACCTCAGTGACCCCCCCAACA

ACTCCCATGGAGAGTCCCTGCCCAAAAAAGCTGTAGGATCCAAGGGGTGTCAATAGCTCGTTCCCGGCA

TCACCTACACACCACAAGCAGGTTTTAATGGAAGCAAGTTGCTCCACCAAATCCACAAAAGGGTAAAGTT

TGTGATTTTTCTTTATCATTGCGATCACCATCTGATACCGTAAGGAGTGCACTTGTTTGGAAGTTCTGAC

TTCTCTGATCTGTCTTGGTCGTTTGTGTTATAAAACCAAAGTTCTCTACAGACTTTATTTTTGTACAATA

TCATTTTGTAACTTTTTACAAATAAAAACTCATTTCTATTGC
```

A representative cDNA encoding isoform 1 is as follows:

(SEQ ID NO: 5)
caaatatgccagaggattatcctgatcagttcgatgatgtcatggattta ttcaagccaccattaaaagactgaaaaggtcaccagataaacaaatggcag tgcttcctagaagagagcggaatcggcaggctgcagctgccaacccagaga attccagaggaaaaggtcggagaggccagaggggcaaaaaccggggttgtg tcttaactgcaatacatttaaatgtcactgacttgggtctgggctatgaaa ccaaggaggaactgattttaggtactgcagcggctcttgcgatgcagctg agacaacgtacgacaaaatattgaaaaacttatccagaaatagaaggctgg tgagtgacaaagtagggcaggcatgttgcagacccatcgcctttgatgatg acctgtcgttttagatgataacctggtttaccatattctaagaaagcatt ccgctaaaaggtgtggatgtatctga The amino acid sequences of the various human GDNF isoforms are as follows:

>gi|40549411|ref|NP_954701.1| glial cell line-
derived neurotrophic factor isoform 2 pre-
proprotein [Homo sapiens]
(SEQ ID NO: 6)
MKLWDVVAVCLVLLHTASAFPLPAANMPEDYPDQFDDVMDFIQATIKRL

KRSPDKQMAVLPRRERNRQAAAANPENSRGKGRRGQRGKNRGCVLTAIH

LNVTDLGLGYETKEELIFRYCSGSCDAAETTYDKILKNLSRNRRLVSDK

VGQACCRPIAFDDDLSFLDDNLVYHILRKHSAKRCGCI

>gi|4503975|ref|NP_000505.1| glial cell line-
derived neurotrophic factor isoform 1 pre-
proprotein [Homo sapiens]
(SEQ ID NO: 7)
MKLWDVVAVCLVLLHTASAFPLPAGKRPPEAPAEDRSLGRRRAPFALSS

DSNMPEDYPDQFDDVMDFIQATIKRLKRSPDKQMAVLPRRERNRQAAAA

NPENSRGKGRRGQRGKNRGCVLTAIHLNVTDLGLGYETKEELIFRYCSG

SCDAAETTYDKILKNLSRNRRLVSDKVGQACCRPIAFDDDLSFLDDNLV

YHILRKHSAKRCGCI

>gi|299473779|ref|NP_001177397.1| glial cell
line-derived neurotrophic factor isoform 3
preproprotein [Homo sapiens]
(SEQ ID NO: 8)
MQSLPNSNGAAAGRDFKMKLWDVVAVCLVLLHTASAFPLPAGKRPPEAP

AEDRSLGRRRAPFALSSDSNMPEDYPDQFDDVMDFIQATIKRLKRSPDK

QMAVLPRRERNRQAAAANPENSRGKGRRGQRGKNRGCVLTAIHLNVTDL

GLGYETKEELIFRYCSGSCDAAETTYDKILKNLSRNRRLVSDKVGQACC

RPIAFDDDLSFLDDNLVYHILRKHSAKRCGCI

```
>gi|299473781|ref|NP_001177398.1| glial cell
line-derived neurotrophic factor isoform 4
preproprotein [Homo sapiens]
                                       (SEQ ID NO: 9)
MQSLPNSNGAAAGRDFKMKLWDVVAVCLVLLHTASAFPLPAANMPEDYP

DQFDDVMDFIQATIKRLKRSPDKQMAVLPRRERNRQAAAANPENSRGKG

RRGQRGKNRGCVLTAIHLNVTDLGLGYETKEELIFRYCSGSCDAAETTY

DKILKNLSRNRRLVSDKVGQACCRPIAFDDDLSFLDDNLVYHILRKHSA

KRCGCI
```

Like other growth factors GDNF has to be cleaved for secretion from the cell, and proteolytically processed for activation and also requires glycosaminoglycans for activation of specific signaling pathways. The GDNF amino acid sequence contains two potential glycosylation sites (discussed in greater detail below).

A multiple sequence alignment of the human GDNF isoforms is presented below. Signal sequences are depicted in bold. Signal peptides are aa 1-19, aa 1-19, and aa 1-36 for isoforms 1, 2 and 3, respectively. Mature peptides are depicted in italics. Mature peptides are aa 78-211, aa 52-185, and aa 95-228 for isoforms 1, 2 and 3, respectively. GDNF proteins have a key functional domain, termed the "transforming growth factor beta (TGF-β) like domain. TGF-β-like domains are aa 118-211, aa 92-185, and aa 135-228, for isoforms 1, 2 and 3, respectively. TGF-β-like domains are underlined.

```
               CLUSTAL 2.1 multiple sequence alignment
                                                           (SEQ ID NOs: 6-9)
          iso1  ----------------MKLWDWAVCLVLLHTASAFPLPAGKRPPEAPAEDRSLGRRRA
          iso3  MQSLPNSNGAAAGRDFKMKLWDWAVCLVLLHTASAFPLPAGKRPPEAPAEDRSLGRRRA
          iso2  ----------------MKLWDWAVCLVLLHTASAFPLPAAN------------------
          iso4  MQSLPNSNGAAAGRDFKMKLWDWAVCLVLLHTASAFPLPAAN------------------
                                ***********************. :

iso1  PFALSSDSNMPEDYPDQFDDVMDFIQATIKRLKRSPDKQMAVLPRRERNRQAAAANPENS
          iso3  PFALSSDSNMPEDYPDQFDDVMDFIQATIKRLKRSPDKQMAVLPRRERNRQAAAANPENS
          iso2  ---------MPEDYPDQFDDVMDFIQATIKRLKRSPDKQMAVLPRRERNRQAAAANPENS
          iso4  ---------MPEDYPDQFDDVMDFIQATIKRLKRSPDKQMAVLPRRERNRQAAAANPENS
                         ******************************************* iso1  RGKGRRGQRGKNRGCVLTAIHLNVTDLGLGYETKEELIFRYCSGSCDAAETTYDKILKNL
          iso3  RGKGRRGQRGKNRGCVLTAIHLNVTDLGLGYETKEELIFRYCSGSCDAAETTYDKILKNL
          iso2  RGKGRRGQRGKNRGCVLTAIHLNVTDLGLGYETKEELIFRYCSGSCDAAETTYDKILKNL
          iso4  RGKGRRGQRGKNRGCVLTAIHLNVTDLGLGYETKEELIFRYCSGSCDAAETTYDKILKNL
                ************************************************************ iso1  SRNRRLVSDKVGQACCRPIAFDDDLSFLDDNLVYHILRKHSAKRCGCI
          iso3  SRNRRLVSDKVGQACCRPIAFDDDLSFLDDNLVYHILRKHSAKRCGCI
          iso2  SRNRRLVSDKVGQACCRPIAFDDDLSFLDDNLVYHILRKHSAKRCGCI
          iso4  SRNRRLVSDKVGQACCRPIAFDDDLSFLDDNLVYHILRKHSAKRCGCI
                ************************************************
```

As mentioned above, the GDNF gene encodes a highly conserved neurotrophic factor. GDNF orthologs share, for example, about 90-95% identity (or more), e.g., human and rat sharing 92% identity (10 amino acids (aa) are different) and human and mouse sharing 94% identity (8 amino acids are different) when comparing mature protein sequences; human and rat sharing 92% identity and human and mouse sharing 93% identity when comparing preproprotein sequences.

Pairwise alignments of human vs. mouse and human vs. rat preproproteins are presented below. The glycosylation sites are Asn (=N) 126 and Asn 162, and are indicated in bold. The skilled artisan will understand that a glycosylation motif is described as NX[ST] where X=any amino acid. The glycosylation motifs in, for example, human GDNF (isoform 1) are as follows aa126-128 (with N-linked glycosylation predicted to occur at N126, and at aa162-164 (with N-linked glycosylation predicted to occur at N162.) (See e.g., Lin et al., 1994, J. Neurochem, 63, 758-68; Trupp et al., 1995, J. Cell Biol, 130, 137-48).

```
Hu    1  MKLWDWAVCLVLLHTASAFPLPAGKRPPEAPAEDRSLGRRRAPFALSSDSNMPEDYPDQ    60
         MKLWDWAVCLVLLHTASAFPLPAGKR  EAPAED SLG RR PFAL+SDSNMPEDYPDQ
Mu    1  MKLWDWAVCLVLLHTASAFPLPAGKRLLEAPAEDHSLGHRRVPFALTSDSNMPEDYPDQ    60

Hu   61  FDDVMDFIQATIKRLKRSPDKQMAVLPRRERNRQAAAANPENSRGKGRRGQRGKNRGCVL   120
         FDDVMDFIQATIKRLKRSPDKQ A LPRRERNRQAAAA+PENSRGKGRRGQRGKNRGCVL
Mu   61  FDDVMDFIQATIKRLKRSPDKQAAALPRRERNRQAAAASPENSRGKGRRGQRGKNRGCVL   120
```

```
Hu    121 TAIHLNVTDLGLGYETKEELIFRYCSGSCDAAETTYDKILKNLSRNRRLVSDKVGQACCR    180
          TAIHLNVTDLGLGYETKEELIFRYCSGSC++AET YDKILKNLSR+RRL SDKVGQACCR
Mu    121 TAIHLNVTDLGLGYETKEELIFRYCSGSCESAETMYDKILKNLSRSRRLTSDKVGQACCR    180

Hu    181 PIAFDDDLSFLDDNLVYHILRKHSAKRCGCI                               211
          P+AFDDDLSFLDDNLVYHILRKHSAKRCGCI
Mu    181 PVAFDDDLSFLDDNLVYHILRKHSAKRCGCI                               211

Hu      1 MKLWDVVAVCLVLLHTASAFPLPAGKRPPEAPAEDRSLGRRRAPFALSSDSNMPEDYPDQ    60
          MKLWDVVAVCLVLLHTASAFPLPAGKR  EAPAED SLG RR PFAL+SDSNMPEDYPDQ
Ra      1 MKLWDVVAVCLVLLHTASAFPLPAGKRLLEAPAEDHSLGHRRVPFALTSDSNMPEDYPDQ    60

Hu     61 FDDVMDFIQATIKRLKRSPDKQMAVLPRRERNRQAAAANPENSRGKGRRGQRGKNRGCVL   120
          FDDVMDFIQATIKRLKRSPDKQ A LPRRERNRQAAAA+PENSRGKGRRGQRGKNRGCVL
Ra     61 FDDVMDFIQATIKRLKRSPDKQAAALPRRERNRQAAAASPENSRGKGRRGQRGKNRGCVL   120

Hu    121 TAIHLNVTDLGLGYETKEELIFRYCSGSCDAAETTYDKILKNLSRNRRLVSDKVGQACCR   180
          TAIHLNVTDLGLGYETKEELIFRYCSGSC+AET YDKILKNLSR+RRL SDKVGQACCR
Ra    121 TAIHLNVTDLGLGYETKEELIFRYCSGSCEAAETMYDKILKNLSRSRRLTSDKVGQACCR   180

Hu    181 PIAFDDDLSFLDDNLVYHILRKHSAKRCGCI                               211
          P+AFDDDL FLDD+LVYHILRKHSAKRCGCI
Ra    181 PVAFDDDLWFLDDSLVYHILRKHSAKRCGCI                               211
```

Human, mouse and rat GDN sequence are set forth as SEQ ID NOs: 6, 10 and 11, respectively. The sequences appearing between aligned sequences above can be considered consensus sequences and are set forth as SEQ ID NOs: 12-13 (where no match between amino acids in aligned sequences can be depicted as X in a consensus sequence, X being one of the two mismatched residues, as depicted.

A multiple sequence alignment of human (isoform 1), mouse and rat GDNF orthologs (mature proteins) is presented below:

```
Hu     78 SPDKQMAVLPRRERNRQAAAANPENSRGKGRRGQRGKNRGCVL                   120
Mu     78 SPDKQAAALPRRERNRQAAAASPENSRGKGRRGQRGKNRGCVL                   120
Ra     78 SPDKQAAALPRRERNRQAAAASPENSRGKGRRGQRGKNRGCVL                   120

Hu    121 TAIHLNVTDLGLGYETKEELIFRYCSGSCDAAETTYDKILKNLSRNRRLVSDKVGQACCR 180
Mu    121 TAIHLNVTDLGLGYETKEELIFRYCSGSCESAETMYDKILKNLSRSRRLTSDKVGQACCR 180
Ra    121 TAIHLNVTDLGLGYETKEELIFRYCSGSCEAAETMYDKILKNLSRSRRLTSDKVGQACCR 180

Hu    181 PIAFDDDLSFLDDNLVYHILRKHSAKRCGCI                               211
Mu    181 PVAFDDDLSFLDDNLVYHILRKHSAKRCGCI                               211
Ra    181 PVAFDDDLWFLDDSLVYHILRKHSAKRCGCI                               211
```

The above sequences are set forth as amino acids 78-211 of SEQ ID NOs: 6, 10 and 11 respectively.

Mature protein sequences are also envisioned in which a methionine (Met; M) precedes the first amino acid of the mature sequence. The M can be added for recombinant protein expression of mature proteins, and is encoded in engineered cDNA expression systems. However, the skilled artisan will appreciate that there are also expression systems which allow the cleavage of the N-terminal M, as it can induce autoimmune reactions or changes in activity of the expressed, mature protein. For example see Nakagawal et al. 1987, Nature Biotech 5, 824-827; Fernández-San Millán et al., 2007, J Biotechnol. 20;127(4):593-604; U.S. Pat. No. 4,870,017.

GDNF sequences are as described above and additional information on said sequences can be found in the GenBank references indicated by the referenced GenBank/gi reference numbers. GDNF sequences are also described in Science. 1993 May 21;260(5111): 1130-2; and in WO 93/06116 and U.S. Pat. No. 7,226,758B1. Truncated forms are further described in US20040127419(A1). Mutations of GDNF are described, for example in Eketjäll et al. 1999 , EMBO 8, 5901-5910. The GDNF protein is further disclosed in, e.g., U.S. Pat. No. 6,362,319 and European Patent No. 0 610 254, and a truncated form of GDNF in U.S. Pat. No. 6,184,200 and European Patent No. 0 920 448.

Exemplary aspects of the invention can further include modified (e.g., recombinantly-modified) forms of GDNF, or of biologically active fragments thereof. In one embodiment, the method of the invention feature the use of fusion proteins of GDNF, for example, fusion proteins including serum albumin or a biologically active fragment thereof, e.g., human serum albumin or a biologically active fragment thereof.) Further exemplary aspects of the invention feature pegylated GDNF proteins, glycan-modified GDNF proteins (e.g, having N-glycan integrated within the protein) and/or polymer-conjugated GDNF (e.g., polymers consisting of a polystyrene backbone with side chains of trehalose.)

Preferred aspects of the invention feature GDNF polypeptides, GDNF homologs (e.g., GDNF orthologs) and/or biologically active portions (i.e., bioactive fragments) of GDNF polypeptides. In one embodiment, GDNF polypeptides can be isolated from cells or tissue sources by an appropriate purification scheme using standard protein purification techniques. GDNF polypeptide can be further derived from said isolated polypeptides using standard enzymatic techniques. In another embodiment, GDNF polypeptides or bioactive fragments thereof are produced by recombinant DNA techniques. Alternative to recombinant expression, GDNF polypeptides or bioactive fragments thereof can be synthesized chemically using standard peptide synthesis techniques.

Polypeptides of the invention are preferably "isolated" or "purified". The terms "isolated" and "purified" are used interchangeably herein. "Isolated" or "purified" means that the protein or polypeptide is substantially free of cellular material or other contaminating proteins from the cell or tissue source from which the polypeptide is derived, substantially free of other protein fragments, for example, non-desired fragments in a digestion mixture, or substantially free from chemical precursors or other chemicals when chemically synthesized. The language "substantially free of cellular material" includes preparations in which the polypeptide is separated from other components of the cells from which it is isolated or recombinantly produced. In one embodiment, the language "substantially free of cellular material" includes preparations of polypeptide having less than about 30% (by dry weight) of non-GDNF polypeptide (also referred to herein as a "contaminating protein"), more preferably less than about 20% of non-GDNF polypeptide, still more preferably less than about 10% of non-GDNF polypeptide, and most preferably less than about 5% non-GDNF polypeptide. When the polypeptide or protein is recombinantly produced, it is also preferably substantially free of culture medium, i.e., culture medium represents less than about 20%, more preferably less than about 10%, and most preferably less than about 5% of the volume of the polypeptide preparation. When the polypeptide or protein is produced by, for example, chemical or enzymatic processing from isolated or purified GDNF protein, the preparation is preferably free of enzyme reaction components or chemical reaction components and is free of non-desired GDNF forms, e.g., aggregates, or GDNF fragments, i.e., the desired polypeptide represents at least 75% (by dry weight) of the preparation, preferably at least 80%, more preferably at least 85%, and even more preferably at least 90%, 95%, 99% or more or the preparation.

The language "substantially free of chemical precursors or other chemicals" includes preparations of polypeptide in which the polypeptide is separated from chemical precursors or other chemicals which are involved in the synthesis of the polypeptide. In one embodiment, the language "substantially free of chemical precursors or other chemicals" includes preparations having less than about 30% (by dry weight) of chemical precursors or reagents, more preferably less than about 20% chemical precursors or reagents, still more preferably less than about 10% chemical precursors or reagents, and most preferably less than about 5% chemical precursors or reagents.

Bioactive fragments of GDNF polypeptides include polypeptides comprising amino acid sequences sufficiently identical to or derived from the amino acid sequence of the GDNF protein, respectively, which include less amino acids than the full length protein, and exhibit at least one biological activity of the full-length protein. Typically, biologically active portions comprise a domain or motif with at least one activity of the full-length protein. A biologically active portion of a GDNF polypeptide can be a polypeptide which is, for example, 10-20, 20-30, 30-40, 40-50, 50-60, 60-70, 70-80, 80-90, 90-100, 100-120, 120-140, 140-160, 160-200, or more amino acids in length. In a preferred embodiment, a bioactive portion of a GDNF protein comprises a TGFβ-like domain. Moreover, other biologically active portions, in which other regions of the protein are deleted, can be prepared by recombinant techniques and evaluated for one or more of the functional activities of a native GDNF protein. Mutants of GDNF can also be utilized as assay reagents or therapeutic or pharmaceutical agents, for example, mutants having reduced, enhanced or otherwise altered biological properties identified according to one of the activity assays described herein.

As defined herein, a GDNF polypeptide of the invention includes polypeptides having the amino acid sequences set forth above, as well as homologs and/or orthologs of said polypeptides, i.e. polypeptides having sufficient sequence identity to function in the same manner as the described polypeptides. To determine the percent identity of two amino acid sequences (or of two nucleotide or amino acid sequences), the sequences are aligned for optimal comparison purposes (e.g., gaps can be introduced in the first sequence or second sequence for optimal alignment). The amino acid residues or nucleotides at corresponding amino acid positions or nucleotide positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. In one embodiment, the alignment generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215:403-10. BLAST alignments can be generated and percent identity calculated using BLAST protein searches (e.g., the XBLAST program) using GDNF protein, or a portion thereof as a query, score=50, wordlength=3.

In another embodiment, the alignment is optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Research* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

A GDNF bioactive fragment is any fragment of GDNF having sufficient size and structure to carry out at least one activity (e.g., biological activity) of the corresponding full-length GDNF protein. Exemplary bioactive fragments include, but are not limited to, enzymatic domains, protein binding and/or interaction domains, receptor binding domains, and the like. Preferred bioactive fragments include regions or domains comprising a TGFβ-like domain, as defined herein.

The GDNF protein or GDNF bioactive fragment, may be detectably labeled. As defined herein, a protein or protein fragment which is "detectably labeled" is on which has been modified to include a component detectable by standard laboratory means, e.g., the protein has been radioactively labeled, chromogenically labeled, or fluorescently labeled. Labeling can be direct, i.e., protein is modified to directly contain the detectable label, or can be indirect, e.g., the protein is modified to include a component with which the detectable label interacts. Furthermore, in other embodiments, the activity of a GDNF protein or GDNF bioactive fragment may be compared to an appropriate control.

In preferred embodiments, a GDNF polypeptide or homolog or bioactive fragment thereof includes at least a TGFβ-like, as defined herein. The TGFβ-like domain is a domain conserved among most, if not all TGFβ family members. To identify the presence of a TGFβ-like domain in an GDNF polypeptide, the amino acid sequence of the polypeptide can be searched against a database of conserved protein domains (e.g., the CD database at the NCBI) using the default parameters (Marchler-Bauer A et al. (2013), "CDD: conserved domains and protein three-dimensional structure.", Nucleic Acids Res. 41(D1):D384-52.). NCBI Conserved Domains Database Accession number pfam00019 sets forth a conserved TGFβ-like domain amino acid sequence.

In exemplary embodiments, a TGFβ-like domain includes about 90-110 amino acid residues, e.g., about 90-100 or 91, 92, 93, 94, 95, 96, 97, 98, 99 or 100 amino acid residues). In exemplary embodiments, a domain identification score of 60 is a suitable threshold score for determining the presence of the domain. For example, searches using the amino acid sequences of human GDNF (isoform 1), mouse GDNF and rat GDNF were performed against the CD database resulting in the identification of a TGFβ-like domain at amino acids 118-211 in each protein.

In preferred embodiments, a GDNF composition is a mature human GDNF protein consisting of 134 amino acids, i.e., amino acids 78-211 of SEQ ID NO:6. This sequence contains two putative N-glycosylation sites as well as seven conserved cysteines in the same relative spacing as the other members of the TGF-beta protein family (Lin et al. 1993, Science, 260: 1130-1132; Eigenbrot and Gerber, 1997, Nat Struct Biol, 4:435-438; Chang et al. 2002, Endocri Rev, 23:787-823). Biologically active mature GDNF dimer is formed by a covalent disulfide bond between the unpaired cysteines in the monomers (Eigenbrot and Gerber, 1997, Nat Struct Biol, 4:435-438).

In other exemplary embodiments, a GDNF protein for use in the methods of the invention can be a variant GDNF protein (or polypeptide), e.g., a variant having at least 90% or at least 95% or more identity. Preferred are biologically active variant GDNF polypeptides. As used herein, the phrase "biologically active variant GDNF polypeptide" refers to a GDNF polypeptide that, when dimerized, binds to a ternary complex containing GFRα1 and RET. Any method for detecting binding to this complex can be used to evaluate the biological activity a variant GDNF polypeptide. Exemplary assays for detecting the ternary complex-binding ability of a variant GDNF polypeptide are described in WO00/01815. Variant GDNF polypeptides can also be assayed or tested for their ability to trigger a GDNF signaling cascade. For example, a kinase receptor activation (KIRA) assay can be used to assess the ability of a variant GDNF polypeptide to induce RET autophosphorylation (see e.g., Sadick et al., 1996, Anal. Biochem., 235(2): 207) or assays can be performed to detect expression of downstream targets of a GDNF signaling cascade, e.g., increased expression of ret or fgfr2.

III. Wound Healing

The body's response to skin injury is focused on rapid wound closure, restraining invasion of microorganisms, and preventing excessive fluid loss (Singer A J, et al., N Engl J Med 341:738-46, 1999; Aarabi S, et al., PLoS Med 4:e234, 2007; Gurtner G C, et al., Nature 453:314-21, 2008; Mustoe T., Am J Surg 187:65S-70S, 2004).

An increased understanding of the molecular mechanisms that regulate the various events of wound healing has laid the foundation for therapeutic interventions attempting to improve the healing outcome. The cell-cell and cell-matrix interactions are fundamental for successful wound healing, and growth factors and cytokines maintain the balance of signals that regulate cellular migration, proliferation, and adhesion to a large extent. Freedberg I M, et al., J Invest Dermatol 116:633-40, 2001; Hantash B M, et al., Front Biosci 13:51-61, 2008; Werner S, et al., Physiol Rev 83:835-70, 2003; Barrientos S, et al., Wound Repair Regen 16:585-601, 2008. Malfunction leads to a prolonged healing time or complete failure to heal and may result in a chronic wound. The wound fluid from chronic wounds has an increased concentration of proinflammatory cytokines in comparison with wound fluid from acute wounds. Bennett N T, et al., Am J Surg 166:74-81, 1993; Robson M C, et al., Arch Surg 135:773-7, 2000. By contrast, there is a decreased concentration of growth factors in chronic wounds with high protease activity and decreased levels of natural protease inhibitors. Nwomch B C, et al., Clin Plast Surg 25:341-56, 1998; Mast B A, et al., Wound Repair Regen 4:411-20, 1996; Tarnuzzer R W, et al., Wound Repair Regen 4:321-5, 1996. This deficiency in growth factors can be attributable to decreased production or secretion, more rapid breakdown, and, as is the case in venous stasis ulcers, binding to in macromolecules, making them nonfunctional. Robson M C, et al., Arch Surg 135:773-7, 2000; Falange V, et al., Lancet 341:1006-8, 1993.

Glial cell line-derived neurotrophic factor (GDNF), neurturin (NTN), and their receptors, GDNF family receptor α-1 (GFRα-1) and GDNF family receptor α-2 (GFRα-2), are critically important for development in systems such as kidney and nervous system. Moreover, Gdnf has been shown to be expressed in embryonic skin where Gdnf mRNA is detected in both epithelial and mesenchymal components (Hellmich et al. 1996, Mech Dev 54, 95-105). However, the role of these factors (e.g., GDNF) in skin biology, and in particular, wound healing, is as yet not fully understood. Knowledge of the role of this important factor in skin biology would be helpful in understanding not only the various normal wound-healing events but also those occurring under distinct pathological conditions, for example, conditions in which wound healing is impaired, e.g., pathological conditions such as diabetes. In addition, development of effective novel therapies for wound healing can based, at least in part, on this better understand of the effect of GDNF on the total wound-healing process. This approach facilitates the development of new products with potential applications in wound healing and other area of skin biology.

In humans, and more widely in all mammalian species, the wound-healing process can be subdivided into three consecutive and overlapping phases: inflammation, tissue formation, and matrix formation and remodeling. Rodero, M. P., et al., Int. J. Clin. Exp. Pathol. 3:643653, 2010. The transition from one phase to another depends on the maturation and differentiation of the main cell populations involved, among which keratinocytes, fibroblasts, neutrophils, and macrophages play the main roles. Rodero, M. P., et al., Int. J. Clin. Exp. Pathol. 3:643653, 2010; Leibovich, S. J., et al., Am. J. Pathol. 78:71-100, 1975; Deonarine, K., et al., J. Transl. Med. 5:11, 2011; Becker, D. L., et al., Biochim. Biophys Acta 1818:2068-2075, 2011. Recent observations show that stem cells have an unclear but likely major role in response to cutaneous injury, Lanza R., *Handbook of Stem Cells*. Academic Press, 2004, as well as the evidence for the roles of M1 and M2 macrophage, and that of T cells. Gilliver, S. C., et al., *Exp. Dermatol.* 20:1-6, 2011; Sindrilaru, A., et al., *J. Clin. Invest.* 121:985-997, 2011.

Initial stages of wound healing involve the formation of a blood clot and inflammation. The inflammatory response is followed by proliferation and migration of dermal and epidermal cells, and matrix synthesis, in order to fill the wound gap and reestablish the skin barrier (Cotran, et al., 1999; Hackam, D. J., et al. *Surg Infect* 3 (Suppl 1), S23-5 (2002); Harding, K. G., et al. *Int Wound J* 2, 364-8 (2005)). Finally, tissue remodeling and differentiation enable full recovery of the skin tissue and restoration of skin aesthetics (Hackam, D. J., et al. *Surg Infect* 3 (Suppl 1), S23-5 (2002); Diegelmann, R. F., et al. *Front Biosci* 9, 283-9 (2004)). The consensus in the literature is that the stepwise process of wound healing first strives toward immediate filling of the gap, followed by re-epithelialization and reestablishment of the skin barrier (Yamaguchi, Y., et al. *J Dermatol* 28, 521-34, (2001)).

The early response is activated immediately after injury, resulting in the inflammatory phase (first stage) of wound healing. Grose R, et al., *Mol Biotechnol* 28:147-66, 2004. After hemostasis a fibrin clot is formed, which later serves as a scaffold for infiltrating cells. In addition, neutrophils and monocytes are recruited to the wound in response to trauma and bacterial contamination. Martin P, et al., *Trends Cell Biol* 15:599-607, 2005. In detail, the first event occurring after injury is the formation of a blood clot; several cells are involved in the blood plug: platelets, and red and white blood cells. With the action of fibrin fibers, the clot is stabilized and then "invaded" by several infiltrating cells, such as neutrophils, macrophages, mastocytes, platelets, and, possibly, by bacteria and toxins, which are counteracted by host-generated $H_2O_2$. Neutrophils massively infiltrating the wound during the first 24 hours postinjury are attracted by numerous inflammatory cytokines produced by activated platelets, endothelial cells, as well as by degradation products from pathogens. Macrophages massively infiltrating the wound two days postinjury produce intense phagocytic activity. Mosser, D. M., et al., *Nature Rev. Immunol.* 8:958-969, 2008.

The second stage of wound repair (tissue formation) occurs approximately 2 to 10 days after the injury and is characterized by proliferation and migration of different cell types. Keratinocytes migrate over the wound bed while fibroblasts and macrophages replace the fibrin clot with granulation tissue. Werner S, et al., *J Invest Dermatol* 27:998-1008, 2007. The newly formed immature dermis is neovascularized, and the keratinocytes behind the leading edge proliferate and differentiate to restore the barrier function of the epidermis. In detail, after two to three days, the second phase lasts about two weeks and is characterized by neo-angiogenesis and granulation. During the re-epithelialization process, keratinocytes from the wound edges migrate over the wound bed at the interface between the wound dermis and the fibrin clot. This migration is facilitated by the production of specific proteases, such as collagenase by the epidermal cells to degrade the extracellular matrix. Activated fibroblasts also migrate to the wound bed and form, with the macrophages, granulation tissue. Intense angiogenesis, allowing the supply of oxygen and nutrients necessary for the healing process, also occurs within the tissue. Both growth factors and reactive oxygen species (ROS) produced by the granulation tissue will favor proliferation and differentiation of epithelial cells, restoring epithelial barrier integrity Tissue remodeling, the third stage of wound repair, begins 2 to 3 weeks after injury and lasts for 1 year or more. The type III collagen that is deposited in the initial stages of wound healing is slowly replaced by type I collagen, thereby forming the mature dermis. Loworn H N $3^{rd}$, et al., *J Pediatr Surg* 34:218-23, 1999. In detail, The last stage of the wound-healing process consists in a gradual involution of the granulation tissue and dermal regeneration. This step is associated with apoptosis of myofibroblasts, endothelial cells, and macrophages. The remaining tissue is therefore composed mostly of extracellular matrix proteins, essentially collagen type III that will be remodeled by metalloproteinase produced by epidermal cells, endothelial cells, fibroblasts, and the macrophages remaining in the scar and then replaced by collagen type I. Singer, A. J., et al., *N. Engl. J. Med.* 341:738-746, 1999.

IV. Hair Growth

As is the case for wound healing, the role of Glial cell line-derived neurotrophic factor (GDNF) and its receptors in hair growth control, is as yet not fully understood. As mentioned above, Gdnf has been shown to be expresses in embryonic skin where Gdnf mRNA is detected in both epithelial and mesenchymal components (Hellmich et al. 1996, *Mech Dev* 54, 95-105). Gdnf has also been shown to be expressed during human hair follicle development (Adly et al. 2008 *J Am Acad Dermatol*, 58:238-250) and has further been shown to be expressed in adult mice in hair follicles during the anagen to catagen transition phase (Botchkareva et al.2000, *Am J Pathol* 156,1041-1053). These gene expression patterns suggest a role for GDNF in the hair follicle development cycle. The instant inventors discovered that in a transgenic mouse model, when Gdnf is over-expressed under the Cathespin L promoter, it affects the hair follicle growth in mice. Further analysis suggested that the effect of GDNF on the hair follicles in these mice was possibly due to expression of Gdnf in cells expressing endogenous Cathespin L gene, cells of the outer and inner root sheath and is essential for regular hair follicle morphogenesis and cycling.

Hair grows in cycles of various phases: anagen is the growth phase; catagen is the involuting or regressing phase (also termed "apoptosis-driven regression"); and telogen, the resting or quiescent phase (see e.g., Stenn and Paus (2001) "Controls of Hair Follicle Cycling". *Physiological Reviews* 81 (1): 449-494 and Paus et al., "The biology of hair follicles", *NEJM* 1999, 341:491-497). The time these phases last varies from person to person. Different hair color and follicle shape affects the timings of these phases. anagen phase, 2-3 years (e.g., approximately 3 years, occasionally much longer); catagen phase, 2-3 weeks; and telogen phase, around 3 months.

Each phase has several morphologically and histologically distinguishable sub-phases. Prior to the start of cycling is a phase of follicular morphogenesis (formation of the follicle). There is also a shedding phase, or exogen, that is independent of anagen and telogen in which one of several hair that might arise from a single follicle exits. Normally up to 90% of the hair follicles are in anagen phase while, 5-15% (or 10-14%) are in telogen and 1-2% in catagen. The cycle's length can vary depending on location on different parts of the body.

Anagen is the active growth phase of hair follicles. The root of the hair are dividing rapidly, adding to the hair shaft. During this phase the hair grows about 1 cm every 28 days.

Scalp hair stays in this active phase of growth for 2-7 years. The amount of time the hair follicle stays in the anagen phase is genetically determined. At the end of the anagen phase an unknown signal causes the follicle to go into the catagen phase.

The catagen phase is a short transition stage that occurs at the end of the anagen phase. It signals the end of the active growth of a hair. This phase lasts for about 2-3 weeks while the hair converts to a club hair. A club hair is formed during the catagen phase when the part of the hair follicle in contact with the lower portion of the hair becomes attached to the hair shaft. This process cuts the hair off from its blood supply and from the cells that produce new hair. When a club hair is completely formed, about a 2 week process, the hair follicle enters the telogen phase.

The telogen phase is the resting phase of the hair follicle. During telogen, the resting hair remains in the follicle until it is pushed out by growth of a new anagen hair. In most people, 5-15% of the hair on the scalp is in telogen at any given time. Shedding does not occur until the new anagen hairs begin to grow. The emerging hairs help to force the resting hairs out of the follicle. Recent evidence suggests that the mechanism of shedding of a telogen hair is an active process that may occur independent of the emerging anagen hair. When the body is subjected to extreme stress, as much as 70 percent of hair can prematurely enter a phase of rest, called the telogen phase. This hair begins to fall, causing a noticeable loss of hair. This condition is called telogen effluvium (see below). Telogen effluvium is a form of nonscarring alopecia characterized by diffuse hair shedding, often with an acute onset. Telogen effluvium can affect hair on all parts of the body, but, generally, only loss of scalp hair is symptomatic. Understanding the pathophysiology of telogen effluvium requires knowledge of the hair growth cycle (as detailed herein.) The club hair is the final product of a hair follicle in the telogen stage, and is a dead, fully keratinized hair. Fifty to one-hundred club hair are shed daily from a normal scalp.

The symptom of both acute and chronic telogen effluvium is increased hair shedding and diffuse hair loss from the entire scalp. Acute telogen effluvium is defined as hair shedding lasting less than 6 months. Patients usually only complain that their hair is falling out at an increased rate or that the remaining hair feels less dense. Causes for telogen effluvium and acute hair shedding can be physiologic stress, papulosquamous diseases of the scalp such as psoriasis and seborrheic dermatitis, allergic contact dermatitis, immunizations, severe infections (HIV), acute illness such as febrile illness, major surgery and severe trauma as well as chronic illness such as malignancy, particularly lymphoproliferative malignancy, systemic lupus erythematosus, end-stage renal disease, or liver disease, hormonal changes such as pregnancy and delivery (can affect both mother and child), hypothyroidism, discontinuation of estrogen-containing medications; changes in diet like crash dieting, anorexia, low protein intake, and chronic iron deficiency, heavy metals such as selenium, arsenic, and thallium. Acute telogen effluvium can occur in either sex, but because hormonal changes in the postpartum period are a common cause of telogen effluvium, women may have a greater tendency to experience this condition. Patients with acute telogen effluvium usually complain of relatively sudden onset of hair loss. If greater than 25% of extracted hairs are in telogen, the diagnosis of telogen effluvium is confirmed. However, each patient's scalp hair has an individual characteristic growth cycle. There are patients who have a very long anagen phase and a small proportion of hair in telogen at any given time. Telogen effluvium can be caused by medications, such as beta-blockers, anticoagulants, retinoids (including excess vitamin A), propylthiouracil (induces hypothyroidism), carbamazepine, and immunizations.

V. Methods of Treatment

The instant invention features the use of GDNF for treatment in cases where wound healing and/or hair growth is desired. In one embodiment, the invention features a method of promoting cutaneous wound healing in a subject, which includes the step of administering at a wound site on the subject a composition comprising a therapeutically effective dose of GDNF, or a biologically active fragment thereof, and (optionally) repeating the administration for a time period sufficient to promote said cutaneous wound healing.

As defined herein, the phrase "cutaneous wound healing" refers to wound healing of the skin, in particular, the skin of a mammal. "Cutaneous wound healing" is also referred to in the art as "dermal wound healing." Cutaneous wound healing is quite distinct from, for example, corneal wound healing. For example, the phases and sequence of events occurring in these type of wound healings differ. Moreover, the goals of these types of wound healing differ, for example, in the desired endpoint. Notably, one of the most crucial aspects of corneal wound healing is how the healing process aims to minimize end results such as vascularization and scar formation (which would have serious visual consequences). By contrast, such processes are significant desired end results of wound healing in other parts of the body, in particular, vascularization.

Administration is preferably topical administration but can also be achieved by injection of GDNF compositions of the invention at the wound site. In preferred embodiments, the wound site is external, e.g., on or in the skin of the subject. In exemplary embodiments, the wound site is an incision, a laceration, an abrasion, a puncture wound, a penetration wound, a surgical wound, an ulceration, a burn, a contusion, a hematoma, or a crush injury. In the case of topical administration, a GDNF composition of the invention can further include at least one anti-inflammatory agent. Alternatively, a GDNF composition of the invention can further include at least one antibiotic. Alternatively, a GDNF composition of the invention can further include at least one other wound healing-promoting agent.

In exemplary aspects of the invention, administration of GDNF composition is repeated for a time at least sufficient to promote filling and re-epithelialization of a wound site. In preferred aspects of the invention, administration of GDNF composition is repeated for a time at least sufficient to reestablish a skin barrier at the wound site.

In exemplary aspects, formulations of GDNF can contain at least about 1 ng/ml and up to about 10 µg/ml (e.g., for cosmetic applications), at least about 10 µg/ml and up to about 100 µg mg/ml or even 1 mg/ml (e.g., for wound healing and/or hair growth applications). In other exemplary aspects, a therapeutically effective dose consists of an amount of GDNF administered in a set period of time (e.g., daily), and routinely repeated over time (e.g., over weeks or months) to get the desired therapeutic effect. For example, GDNF compositions can be used at the concentration recited above and administered in a therapeutically effective dose (e.g., 1-100 ng daily, 100 ng to 1 µg daily, 1-50, 50-100, or 100-500 µg daily, 100 or 500 µg, up to 1 mg daily, 1-10 mg daily, 10-20 mg daily, 20-30 mg daily, 30-40 mg daily, or more. In some embodiments, a GDNF composition is administered daily. In other embodiments, a GDNF composition is administered multiple times a day e.g., twice or three times daily. The skilled artisan will readily appreciate that doses can be significantly lower if the compositions are to be administered via a controlled release system or formulation. For example, doses in the ng/ml or even pg/ml range are possible in the case of controlled release systems or formulations.

In other aspects, the invention features methods for promoting hair growth on a subject which includes the step of administering at site of desired hair growth on the subject (e.g., at a skin site where hair follicles grow) (e.g., on a scalp) a composition comprising a pharmaceutically effective dose of isolated GDNF, or a biologically active fragment thereof, and repeating the administration for a time period sufficient to promote said hair growth on said subject.

As a measure of efficacy, a pharmaceutically effective dose is a dose sufficient to promote a 5%, 10%, 15%, 20%, 25% increase in hair follicle number (or follicular units) over a period of several weeks to several months. Preferably, a pharmaceutically effective dose is a dose sufficient to promote a 10% increase in hair follicle number (or follicular units) over a period of several weeks to several months. Even more preferably, a pharmaceutically effective dose is a dose sufficient to promote a 50% (or more) increase in hair follicle number (or follicular units) over a period of several weeks to several months. In exemplary embodiments, the method of promoting hair growth involves administration of a GDNF composition via topical contacting at a skin site containing hair follicles (or a skin site that normally contains hair follicles). A skin site for hair growth can be virtually anywhere on the body except, for example, the soles of the feet and the palms of the hands, the lips, and the eyelids, apart from eyelashes.

As an alternative, efficacy of treatment can be monitored according to any art-recognized means for evaluating hair loss in a subject. Without being bound in theory, it is proposed that the methods of the invention can reduce hair shedding, for example, to a normal level. Exemplary non-invasive methods for monitoring hair loss include daily hair counts, standardized wash test, and the like (e.g., questionnaires, 60-s hair count, global photographs, dermoscopy, hair weight, contrasting felt examination, hair feathering test, phototrichogram and TrichoScan), which are good methods for primary evaluation of the patient and to get an approximate assessment of the amount of shedding. While not preferred, semi-invasive methods, e.g., Trichogram and unit area trichogram (UAT), and/or invasive methods, e.g., scalp biopsy, can also be used to measure hair loss (and, indirectly, hair growth.). For a detailed description of these procedures, see e.g., Dhurat, R. and Saraogi, P. 2009 *Int J Trichology* 1(2): 108-119.

As a measure of efficacy, a pharmaceutically effective dose is a dose sufficient to promote a 5%, 10%, 15%, 20%, 25% decrease in hair loss over a period of several weeks to several months. Preferably, a pharmaceutically effective dose is a dose sufficient to promote a 10% decrease in hair loss over a period of several weeks to several months. Even more preferably, a pharmaceutically effective dose is a dose sufficient to promote a 50% (or more) decrease in hair loss over a period of several weeks to several months.

In exemplary embodiments, the hair growth promoting methods of the invention are used to treat androgenetic alopecia (AGA), also known as male pattern baldness or female pattern baldness. In other embodiments, the hair growth promoting methods of the invention are used to treat autoimmune alopecia. This disease interferes with the hair growth cycle by causing a follicle to prematurely leave the anagen, or active growth, phase and enter the resting, or telogen phase. The hair growth in the affected follicles is lessened or stopped completely.

In other embodiments, the hair growth promoting methods of the invention are used to treat hair shedding. In other embodiments, the hair growth promoting methods of the invention are used to treat hair thinning. In yet other embodiments, the methods of the invention are used to treat acute or chronic telogen effluvium. In still other embodiments, the methods of the invention are used, generally, to treat scalp hair loss, hair thinning or baldness (poor hair thickness, poor hair growth). In yet another embodiment, the methods of the invention are used to extend the life or otherwise improve the condition of hair implants.

In other embodiments, the methods of the invention are used to treat iatrogenically-induced hair loss, for example, scalp hair and/or eye brow hair loss in chemotherapy patients. As used herein, the phrase "iatrogenically-induced" refers to a condition or disease state caused by a physician, surgeon, or other administering professional or by a medical or surgical treatment (e.g., pharmaceutical treatment, chemotherapeutic treatment, radiation treatment) or a diagnostic procedure.

In some embodiments, the GDNF compositions of the invention can be used in combination with one or more additional agents, e.g., art-recognized agents that promote wounds healing or hair growth and/or reduce hair loss. For example, the GDNF compositions of the invention might be used in combination, or in a combination therapy, with any one (or more than one) of the following agents: Combination platelet-derived growth factor (PDGF), interleukin-1 (IL1), nerve growth factor (NGF) or proNGF, keratinocyte growth factor (KGF), thymic peptides of the families of thymulin, thymosin alpha-1 and thymosin beta-4 (see e.g., US20110281802A1). Combination treatment can include, in other embodiments, coincident oral treatment with, for example, vitamins; combination of vitamin B1, vitamin B6, vitamin B12, folic acid, magnesium glycinate, L-cysteine, biotin, ferric glycinate, Polygonum multiflorum, and/or Emblica officinalis (see e.g., US20130017285); insulin, insulin-like growth factor (IGF) (see e.g. US20100172865; Yoon et al. 2011, PLoS ONE 6(12): e28474), and/or polyamines (see e.g., Ramot et al. 2011, PLoS ONE 6(7): e22564). In some embodiments, the GDNF compositions of the invention can be used in combination with an electrical stimulus or mechanical stimulus (see e.g., Yoon et al. 2011, PLoS ONE.)

Without being bound in theory, it is also believed that GDNF, or a biologically active fragment thereof, can be administered to subjects via a gene therapy approach, for example, in cases where healing of chronic wounds is desired. GDNF-encoding nucleic acids can be engineered into appropriate expression vectors and targeted to areas requiring continued supply of expressed GDNF. Expression vectors can be engineered to encode GDNF, or a biologically active fragment thereof, in the context of a fusion protein, for example, fuse with a receptor targeting means for achieving entry into cells of the skin. Also, vectors can be formulated with agents that promote entry of nucleic acid molecules into skin.

VI. Other Uses

Chronic Wound Healing

The instant invention also features the use of GDNF for treatment in cases where a subject suffers from chronic nonhealing wounds. Experts debate about the time for closure that defines a chronic nonhealing wound as compared to that required for closure of an acute wound. Dealey, C., 3rd ed. Blackwell Publishing Ltd., 2005; Whitney, J. D., Nurs. Clin. North Am. 40:191-205, 2005; Bryant, R A., et al., *Acute and Chronic Wounds, Current Management Concepts*. 4th ed. Mosby, 2011. It has been stated that "acute wounds generally follow trauma or inflammation and usually heal within six weeks." Kumar, S., et al., *Surgery* 26:43-47, 2008. Chronic wounds (in addition to failing to heal after six weeks) have characteristic pathological associations that inhibit or delay the healing process. Jones, K. R., et al., *Adv. Skin Wound Care* 20:591-600, 2007.

Chronic wound healing is mainly sustained by chronic inflammation, which without appropriate therapy tends to worsen. The basic reasons are not necessarily old age but rather hypertension and atherosclerosis, which can lead to ischemia, diabetes, and venous insufficiency. Common pathogenetic causes are local tissue hypoxia, edema, abundant bacterial colonization, and, possibly, repeated ischemia-reperfusion injuries. The surface area of a nonhealing wound tends to widen and shows fibrin deposition, necrotic areas, and a few islands of granulation tissue. It is estimated that, in the industrialized world, 1-1.5% of the population experience problems related to recovering proper skin function. The problem is particularly prominent in elderly and diabetic patients, or those with arteriosclerosis.

Common chronic wounds include, but are not limited to pressure ulcers, venous ulcers, and the like. Pressure ulcers, also known as decubitus ulcers or bedsores, are localized injuries to the skin and/or underlying tissue usually over a bony prominence, as a result of pressure, or pressure in combination with shear and/or friction. Most commonly this will be the sacrum, coccyx, heels or the hips, but other sites such as the elbows, knees, ankles or the back of the cranium can be affected. The cause of pressure ulcers is pressure applied to soft tissue so that blood flow to the soft tissue is completely or partially obstructed. Shear is also a cause; shear pulls on blood vessels that feed the skin. Pressure ulcers most commonly develop in persons who are not moving about or are confined to wheelchairs. Pressure ulcers can be very difficult to prevent in critically ill patients, frail elders, wheelchair users (especially where spinal injury is involved) and terminally ill patients. Venous ulcers (stasis ulcers, varicose ulcers, or ulcus cruris) are wounds that are thought to occur due to improper functioning of venous valves, usually of the legs. The exact etiology of venous ulcers is not certain, but they are thought to arise when venous valves that exist to prevent backflow of blood do not function properly, causing the pressure in veins to increase. They are a major cause of chronic wounds, occurring in 70% to 90% of chronic wound cases. Venous ulcers develop mostly along the medial distal leg, and can be very painful.

Burn Wounds

The instant invention also features the use of GDNF for treatment in cases where a subject suffers from burn wounds. Most burn wounds affect only the skin (epidermal tissue). Rarely, deeper tissues, such as muscle, bone, and blood vessels can also be injured. Burns are described according to the depth of injury to the dermis and are loosely classified into first (involving the epidermis), second (extending into superficial (papillary) dermis and/or extending into deep (reticular) dermis), third (extending through entire dermis), and fourth (extending through skin, subcutaneous tissue and into underlying muscle and bone) degrees. Burns are caused by a wide variety of substances and external sources such as exposure to chemicals, friction, electricity, radiation, and heat. Generally, the methods of the invention are suited to the treatment of first through third degree burns.

Freezing Injury

The instant invention also features the use of GDNF for treatment in cases where a subject suffers from freezing injury, in particular, from wounds or tissue damage resulting from freezing injury. An exemplary freezing injury is frostbite. Frostbite is the medical condition in which localized damage is caused to skin and other tissues due to freezing. Frostbite is most common in body parts farthest from the heart and those with large exposed areas. Frostbite involves tissue destruction. Second-degree injury usually involves blisters (appearing 1-2 days after tissue becoming frozen.) The blisters may become hard and blackened, with time. Most of the injuries heal in one month, but the area may become permanently insensitive to both heat and cold. The GDNF treatment methodologies of the invention are suited for treatment of tissue damage, blisters, wounds and the like associated with frostbite and other freezing injuries.

Diabetics

Diabetes mellitus is well known for its skin complications, usually leading to the formation of chronic debilitating ulcers (Levin, M. E. 1995, *DiabetesCare* 18, 1383-94; Cavanagh, P. R., et al. 1998, *Ostomy Wound Manage* 44, 6S-12S ; Brem et al., 2003). Wound-healing impairment is characterized by the inability of the healing process to progress, thus leaving the wound susceptible to external infections as well as to deterioration of the underlying tissue, leading to morbidity and sometimes requires amputation (Brem, H. et al. *Surg Technol Int* 11, 161-7 (2003); Freedman, H., et al. *Am J Surg* 188, 31-5 (2004); Mousley, M. *Nurs Times* 99, 70-4 (2003); Wertheimer, E. *Isr Med Assoc J* 6, 287-9 (2004)). Accordingly, the instant invention also features the use of GDNF for treatment in cases where a subject suffers from ulcers associated with diabetes. In exemplary embodiments, the invention features use of GDNF for treatment of "diabetic foot ulcer" and/or "non-healing chronic diabetic ulcers."

Cosmetic Applications

Without being bound in theory, it is proposed that the GDNF compositions of the invention may have utility in the field of cosmetic applications, e.g., in dermatological application. For example, the GDNF compositions of the invention could be useful as. "antiaging" substances and/or may improve the appearance of wrinkles. It was noted in the wound healing experiments, described herein, that mice exhibited smoother skin following GDNF treatment. Other research on wound healing has produced much evidence showing the importance of peptides in improving the signs of aging (Lupo M P, Cole A L. Dermatol Ther. 2007;20: 343-349). Thus, in exemplary embodiments, the GDNF peptides of the invention can be used in methods to improve fine lines, skin texture, and/or hyperpigmentation in addition to their uses .to influence wound healing. It is important for such application that the /protein peptide is stable in formula, deliverable to its target dermal site, and biologically active at this target site (Lupo M. Dermatol Surg. 2005;31: 832-836).

Screening Assays

In other aspects, the invention features the use of GDNF peptides/proteins in screening assays, e.g., in screening assays for compounds that modulate one or more of the biological activities of GDNF in the processes of wound healing and/or hair growth. In one embodiment, the invention features contacting a composition comprising GDNF with a test compound and determining the ability of the test compound to upregulate, e.g., increase or enhance, the activity of GDNF (or a biologically active fragment thereof) such that a compound having the potential to increase hair growth or improve wound healing is identified. In another embodiment, the invention features contacting a cell expressing GNDF with a test compound and determining the ability of the test compound to upregulate, e.g., increase or enhance, the expression or activity of GDNF (or a biologically active fragment thereof) such that a compound having the potential to increase hair growth or improve wound healing is identified. In exemplary embodiments, the cell is a cell known in the art to play a role in wound healing and/or hair growth. A multitude of screening assay formats art known in the art and it is contemplated that screening assays of the invention can make use of labeled reagents, e.g., labeled GDNF proteins, unlabeled reagents, immobilized reagents, and the like. High throughput formats are also well known in the art and are contemplated as a preferred embodiment for the screening assays of the invention.

VI. Pharmaceutical Compositions and Formulations

In other aspects, the invention features pharmaceutical formulations that include a therapeutically effective dose of isolated GDNF, or a biologically active fragment thereof, formulated in combination with at least one agent which facilitates administration of said GDNF, or a biologically active fragment thereof.

Topical formulations are often prepared in the form of emulsions. The term "emulsion," as used herein refers to mixtures of two or more liquids, which may be in the form of a continuous phase and a disperse phase, for example. Exemplary emulsions may be in the form of creams, lotions, ointments, gels, etc. and may include, for example, oil-in-water emulsions, water-in-oil emulsions, multiple emulsions and microemulsions. These formulations will be prepared which contain from about 0.001 to 10 w/w % of the GDNF compositions of the present invention. These formulations will then be administered or applied to the desired areas, e.g., from 1 to 4 times daily. Alternatively, these formulations will be administered or applied to the desired areas less frequently, i.e., from 1 to 5 times a week. Formulations can be applied or administered, for example, every other day, every third day, and so forth. Administration or application may vary in frequency over the course of treatment.

The GDNF compositions may also be administered topically in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines. A potential formulation for topical delivery of the hair treatment compositions used in the methods of the present invention utilizes liposomes such as described in U.S. Pat. No. 4,911,928 and U.S. Pat. No. 5,834,014.

Carriers for systemic administration include, for example, sugars, starches, cellulose and its derivatives, malt, gelatin, talc, calcium sulfate, vegetable oils, synthetic oils, polyols, alginic acid, phosphate buffer solutions, emulsifiers, isotonic saline and pyrogen-free water. Suitable carriers for parenteral administration include, for example, propylene glycol, ethyl oleate, pyrrolidone, ethanol, and sesame oil.

In exemplary embodiments, the GDNF compositions of the invention are formulated in gels or in nanoparticles. Exemplary gels include, for example, carboxymethylcellulose-based gels. Further exemplary gel formulations include, but are not limited to, polymeric gel formulations, in particular, those comprising a polymer selected from the group consisting of vinyl polymers, polyoxyethylene-polyoxy propylene copolymers, polysaccharides, proteins, poly(ethylene oxide), acrylamide polymers and derivatives or salts thereof. Such gel formulations are described in, e.g., U.S. Pat. No. 5,705,485; formulation with nanoparticles.

In other exemplary embodiments, the GDNF compositions of the invention are formulated in heparin, heparan sulphate (see e.g., US Application 2010/0056440), hyaluronic acid, lactic acid or in glycolic acid. In other exemplary embodiments, the GDNF compositions of the invention are formulated in combination with polymeric compounds (such as polylactic acid, polyglycolic acid, poly (lactide-co-glycolide) (PLGA) microparticles, etc.) or in liposomes. In yet other exemplary embodiments, the GDNF compositions of the invention are formulated in collagen-coated delivery systems or in combination with alginate, chitosan, lactide and/or lactide/glycolide copolymers. In yet other embodiments, the GDNF compositions of the invention are formulated as part of a topical dressing (e.g., within an adhesive bandage). In yet other embodiments, the GDNF compositions of the invention are formulated as slow release forms, in films (e.g., biodegradable or non-biodegradable firms. In yet other embodiments, the GDNF compositions of the invention are formulated in combination with PEG 400 or serum albumin (e.g., human serum albumin.)

In other exemplary embodiments, the GDNF compositions of the invention are formulated as hydrogel compositions, i.e., hydrogels or hydrogel formulations. In a preferred aspect of the invention, the hydrogels comprise GDNF. In a preferred aspect of the invention, the hydrogels comprise GDNF included within liposomes. Liposomes have been used in delivering bioactive compounds, for example, growth factors and/or cytokines, for therapeutics purposes due to low toxicity, lack of immune system activation and targeted delivery at the site of action.

In one aspect, the invention features a hydrogel composed of liposomes (e.g., liposomes including GDNF) and chitosan. Ogiso et al., have shown that the negatively charged liposomes diffuse to dermis and lower part of hair follicles, increasing the permeation of drug through the skin (Ogiso T, etal., (2001). J Drug Targeting.: 9, 49-59.) Chitosan, a natural polysaccharide polymer, has been used as a hydrogel mixed with liposomes to deliver growth factors at the injected site with slow release of the bioactive molecules. Earlier studies have shown that production of the vascular endothelial growth factor is up-regulated in wound healing when macrophages are activated by chitin/chitosan (review by Muzzarelli, see e.g., Muzzarelli, R A A. (2009) Carbohydrate Polymers: 76, 167-182). Moreover, Patel et al., have shown that GDNF-Chitosan blended nerve guides enhances both functional and sensory recovery in vivo (Patel M, et al., (2007). J tissue Eng. & Regenerative Med.: 1, 360-367). For further background, see e.g., Elcin Y M et al. (1996) Artif. Cell Blood Substit. Immobil. Biotechnol.: 24, 257-271

Accordingly, in one aspect, the invention features a therapeutic delivery system, e.g., a drug delivery formulation, comprising liposomes containing GDNF, formulated into a hydrogel, e.g., chitosan, for administration in a therapeutic regimen described herein, for example, for administration to a wound site, e.g., in wound healing aspects of the invention. In an exemplary embodiment, the invention features hydrogels made according to the following process. Growth factor or cytokine, e.g, GDNF is loaded into liposomes and then mixed with hydrogel agent, e.g., chitosan. Briefly, liposomes are dissolved in appropriate solvent or buffer and into a thin film (e.g., air and/or gas dried.) Dries films are then resuspended and filteres through appropriately sized filters to generate small unilamellar vesicles. Liposome-encapsulated growth factor/cytokine, e.g, GDNF can be prepared by sonication of the lipids and growth factor/cytokine in appropriate weight/weight ration. To generate hydrogels, liposome-encapsulated growth factor/cytokine, e.g, GDNF can be added to a solution, e.g., a prechilled solution) of hydrogel polymer, for example, chitosan (dissolved in appropriate solvent/buffer) by gentle stirring for an appropriate time before applying at the site of administration, e.g., at the wound site.

It will be recognized by the skilled artisan that the compositions so-formulated can also include inactive ingredients, for example, preservatives, stabilizers, solubilizers, and the like: sodium chloride, sodium acetate trihydrate, glacial acetic acid, water for injection, and methylparaben, propylparaben, and m-cresol as preservatives and l-lysine hydrochloride as a stabilizer.

Exemplary inactive ingredients include, for example, buffer, for example, pH buffer e.g., sodium phosphate, potassium phosphate, histidine, or Tris-HCl, e.g., at a concentration of 10-50 mM; salt (for the purpose of tonicity modifier and solubilizer), e.g., NaCl and $CaCl_2$ at a concentration of 10-100 mM; sugar (for the purpose of protein-stabilizer, bulking agent, etc), e.g., sucrose or trehalose at a concentration of 10-100 mg/mL; polyol (for the purpose of tonicity modifier and bulking agent), e.g., mannitol or sorbitol at a concentration of 10-100 mg/mL; amino acid (for the purpose of tonicity modifier, bulking agent and stabilizer), e.g., glycine or arginine at a concentration of 10-100 mg/mL; polymer (for the purpose of bulking agent etc.), e.g., hydroxyethyl starch at a concentration of 10-50 mg/mL; surfactant (for the purpose of solubilizer, stabilizer and aggregation inhibitor), e.g., Tween-80, Tween-40, and/or SDS at a concentration of <1 mg/mL; preservative (for the purpose of antimicrobial preservation), e.g., benzyl alcohol or phenol e.g., at a concentration of 1-10 mg/mL; and/or antioxidant (for the purpose of antioxidant), e.g., ascorbic acid e.g., at a concentration of 1-10 mg/mL; and or other agents (with a purpose of protein-specific stabilization). Exemplary formulations are also described, for example, in U.S. Pat. No. 8,383,114.

Administration may be by periodic injections of a bolus of the pharmaceutical composition or may be made more continuous by intravenous or intraperitoneal administration from a reservoir which is external (e.g., an IV bag) or internal (e.g., a bioerodible implant). See, e.g., U.S. Pat. Nos. 4,407,957, 5,798,113, and 5,800,828, each incorporated herein by reference.

Examples of parenteral delivery systems include, but are not limited to, ethylene-vinyl acetate copolymer particles, osmotic pumps, implantable infusion systems, pump delivery, encapsulated cell delivery, liposomal delivery, needle-delivered injection, needle-less injection, nebulizer, aeorosolizer, electroporation, hydrogels and transdermal patches. In some embodiments, compositions of the invention may be provided in lyophilized form as a dried powder or a cake.

In the case of injections of the GDNF compositions, GDNF proteins can be formulated in sterile physiological saline solution (e.g., 10 nM citrate and 150 mM sodium chloride), optionally including heparin, heparan sulphate, and/or glycerol.

In some embodiments, GDNF can be produced in *Escherichia coli* cells that contain an expression plasmid with a DNA insert encoding mature human GDNF. In such embodiments, it is preferred to engineer into the protein an N-terminal methionine.

The following examples illustrate the preparation of certain specific compounds according to the present technology. A skilled artisan appreciates that the invention is not limited to the exemplary work described or to the specific details set forth in the examples.

A skilled artisan further appreciates that the experimental conditions depicted in the following examples can be varied by as much as 2%, 5%, 10% or 20% above or below the listed amount, temperature, concentration, pH, time and rpm in order to optimize the conditions to achieve the desired results from the experiments.

EXAMPLES

Example 1: Transgenic Overexpression of GDNF

In a transgenic mouse model generated in the laboratory for a different hypothesis, when Gdnf is over-expressed under the Cathespin L promoter, it affects the hair follicle growth in mice. Further analysis suggested that the effect of GDNF on the hair follicles in these mice could be due to expression of Gdnf in cells expressing endogenous Cathespin L gene, cells of the outer and inner root sheath and is essential for regular hair follicle morphogenesis and cycling. Though we do not understand the mechanism how GDNF regulates hair follicle growth but Gdnf is expressed in embryonic skin where Gdnf mRNA is detected in both epithelial and mesenchymal components (Hellmich et al. 1996, Mech Dev 54: 95-105).

Transgenic mice were generated by microinjection a DNA construct comprising the Cathespin L promoter operably linked to the Gdnf cDNA Ctsl promoter driven Gdnf transgene contains a 3 kb genomic fragment upstream of the rat Ctsl translational start site. The numbering is relative to the Ctsl transcriptional start site, designated by +1. The coding sequence of Gdnf-Gfp fusion gene was cloned downstream of the promoter, using standard methods as described in Manipulating the Mouse Embryo: A Laboratory Manual, 3rd edition, Cold Spring Harbor Laboratory Press; 2002, ISBN-10: 0879695919. The Cathespin L promoter is described in Charron et al. 2003, Biol Reprod,81(3), 1641-1648. When we analyzed the FVB transgenic mice Tg(Ctsl-Gdnf) we detected ruffled fur by 3 wk of age. We prepared paraffin skin sections stained with H&E. Analysis of such revealed an increased number of hair follicles adjacent to normal hair development compared to skin section from control littermate. This phenotype was reproducible in a different genetic background, using the mouse strain B6C3H. The transgenic mice expressing mouse Gdnf under Cathespin L promoter (Tg-Ctsl-Gdnf) were generated in the FVBN/J and B6C3HF1 strain.

Example 2: Accelerated Wound Healing of a Full-Thickness Wound

Figure 8A:
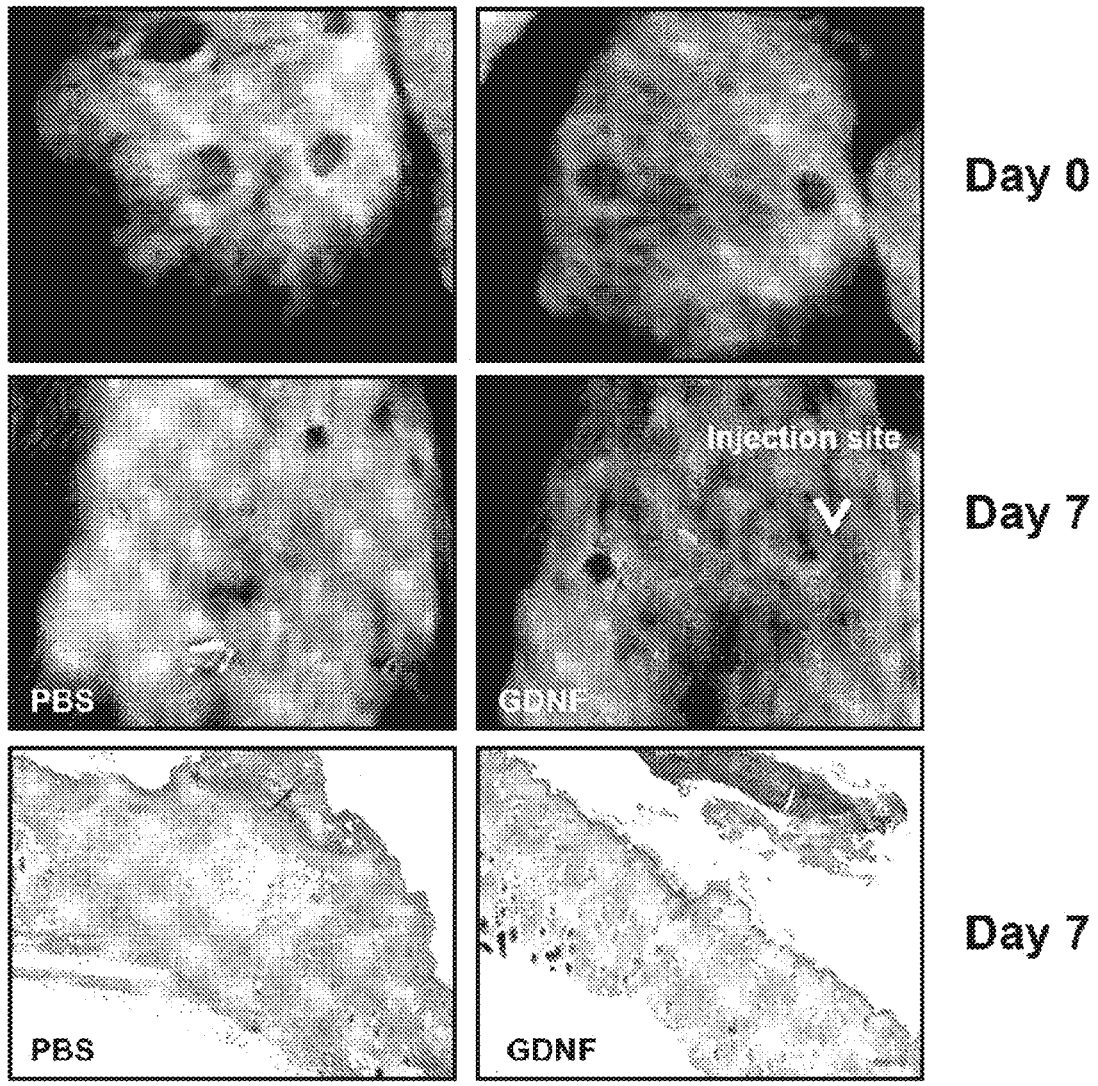
FIG. 8A-8B. GDNF accelerates wound-healing process in B6 wild type mice. Equal size 3 mm of wounds were made by biopsy punch needle on the dorsal side of adult mice. Wounds were photographed on day 0 and after one week. Only one wound site was injected with GDNF (arrow). H&E stained sections of wound sites injected with PBS or one injection of 0.1 ml of 0.5 mg/ml of GDNF. By one week all layers of skin, epidermis, dermis, and hair follicles are present at the wound site injected with GDNF compared to PBS injected sites (A). In the GDNF injected site, a complete layer of epithelium is seen throughout the wound site (arrow) and new blood vessels (arrowheads) after 96 hr were as red blood cells are seen at PBS injected site (asterisk) (B).
Figure 8B:
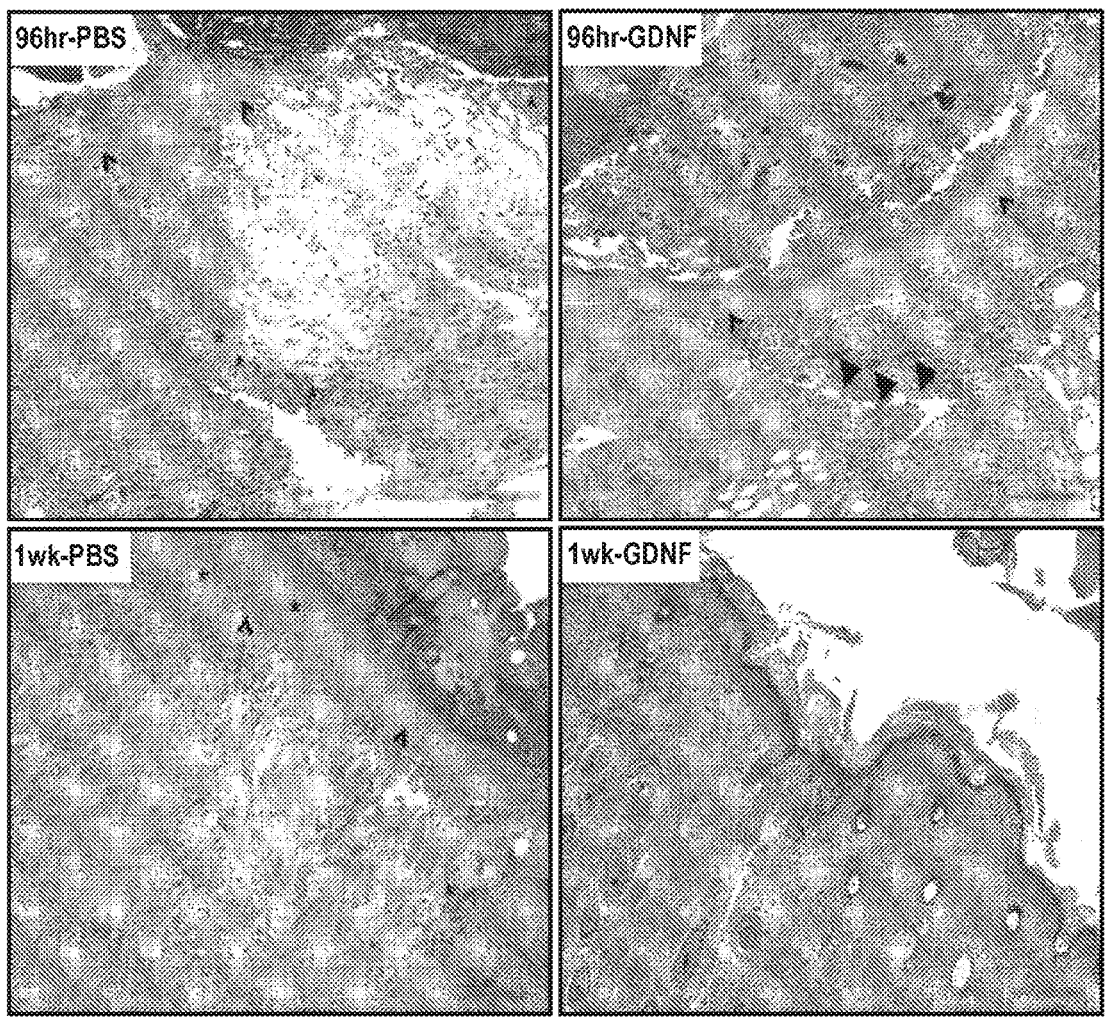
Figure 9:
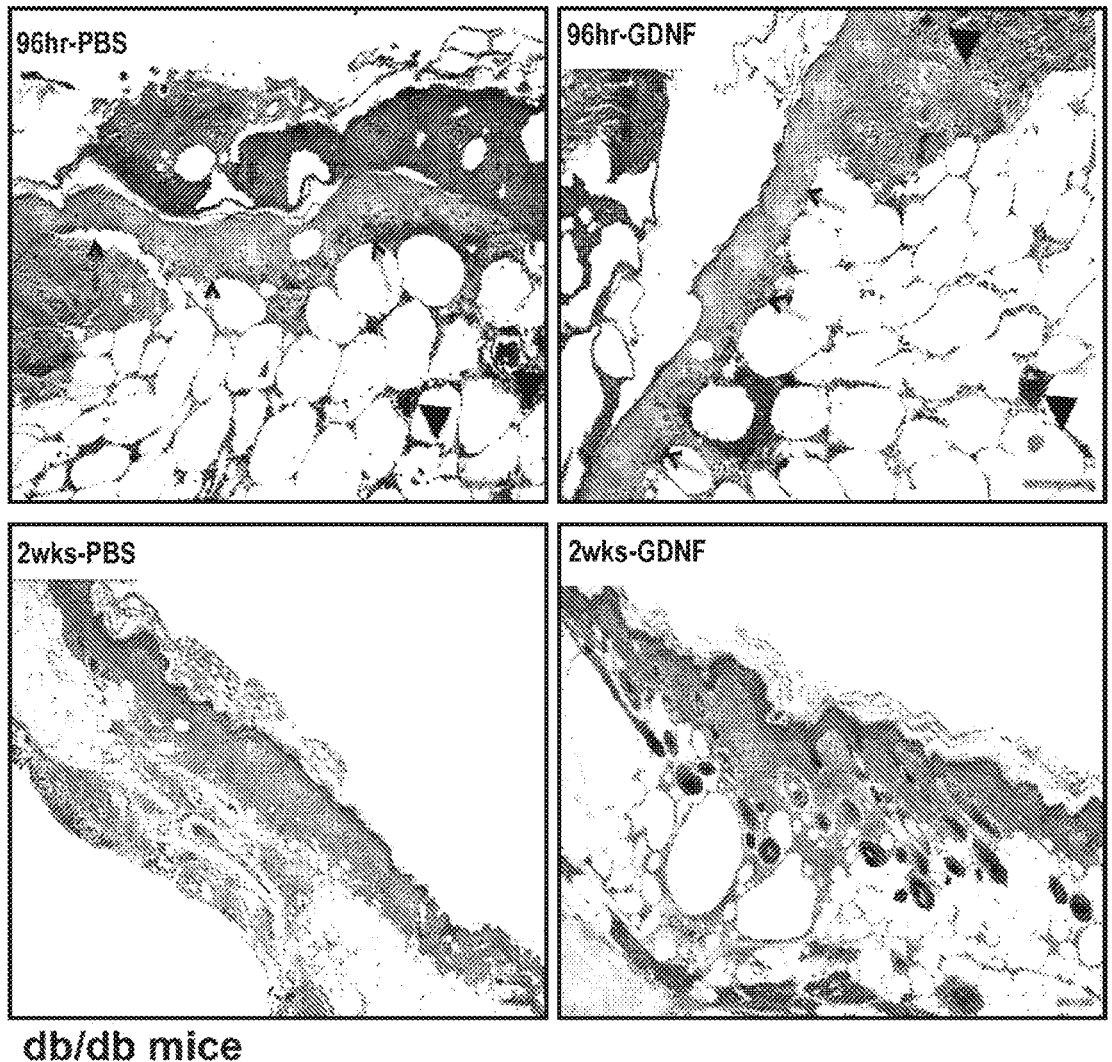
FIG. 9. GDNF accelerate the wound healing process in diabetic BKS.Cg-Dock7$^m$+/+Lepr$^{db}$/J mice. In the diabetic mice, re-epithelialization (arrow) and neovascularization and blood vessels (arrowhead) formation is observed as early as 96 hr. However, complete wound healing occurs after two weeks in the mice injected with 125 μg of GDNF. Scale=100 um FIG. 10. GDNF induces blood vessel growth in FVB mice. The figure shows an increased blood vessel growth and branching after injection of 50 μg GDNF (B) in comparison to the PBS control (A).
Figure 10:
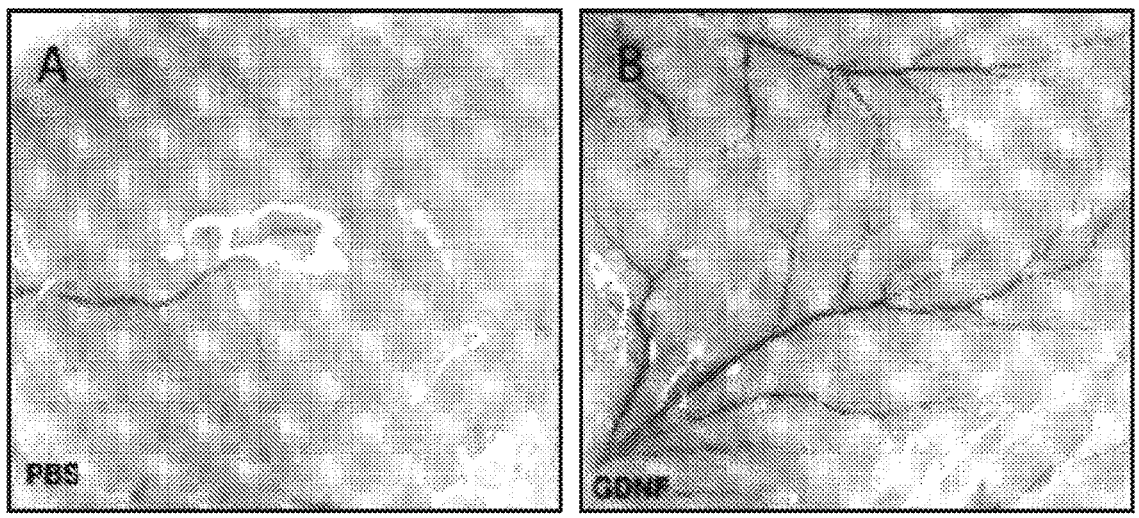

Wild type C57BL/6J (B6) or BKS.Cg-Dock7$^m$+/+Lepr$^{db}$ mice were anesthetized using isoflurane. Before wound setting, the hair was removed on the dorsal side using a clipper. Loose hair was removed with dry gauze dampened with 70% ethanol. Four 3 mm full skin wounds were made using a 3 mm biopsy punch needle. 100 μl of PBS or rat GDNF recombinant protein (Ser78-Ile211) from R&D system (cat no. 512-GF) at concentrations of 0.1 mg/ml or 0.5 mg/ml diluted in PBS was injected either at the wound site or subcutaneously in the middle of the 4 wounds using 30G needles, approximately 5-6 mm adjacent to the wounds. The mice were housed individually and monitored daily after surgery. Wound re-epithelialization and hair follicle development was determined by histology at 96 hrs, 6, 8, and 15 days after injection of the recombinant GDNF protein (FIGS. 8A, 8B and 9).

Example 3: Dose Comparisons for Hair Follicles

Figure 3:
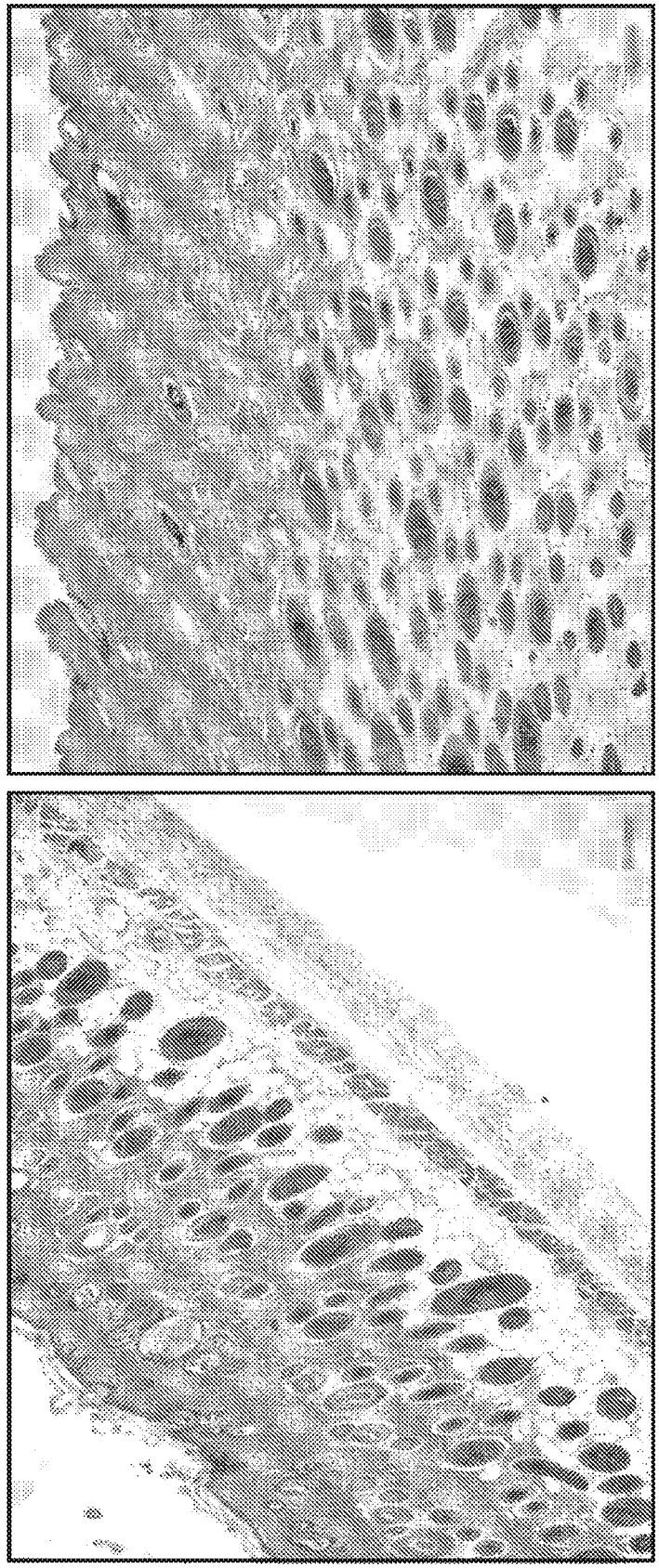
FIG. 3. Multiple injections of low dose are more effective than one injection of high concentration of GDNF. H&E image of skin from mouse injected with 100 ul of 0.5 mg/ml (A) or 5 injections of 100 ul of 0.1 mg/ml of GDNF on alternate days. Both images are at same magnification. Scale=100 um.
Figure 4:
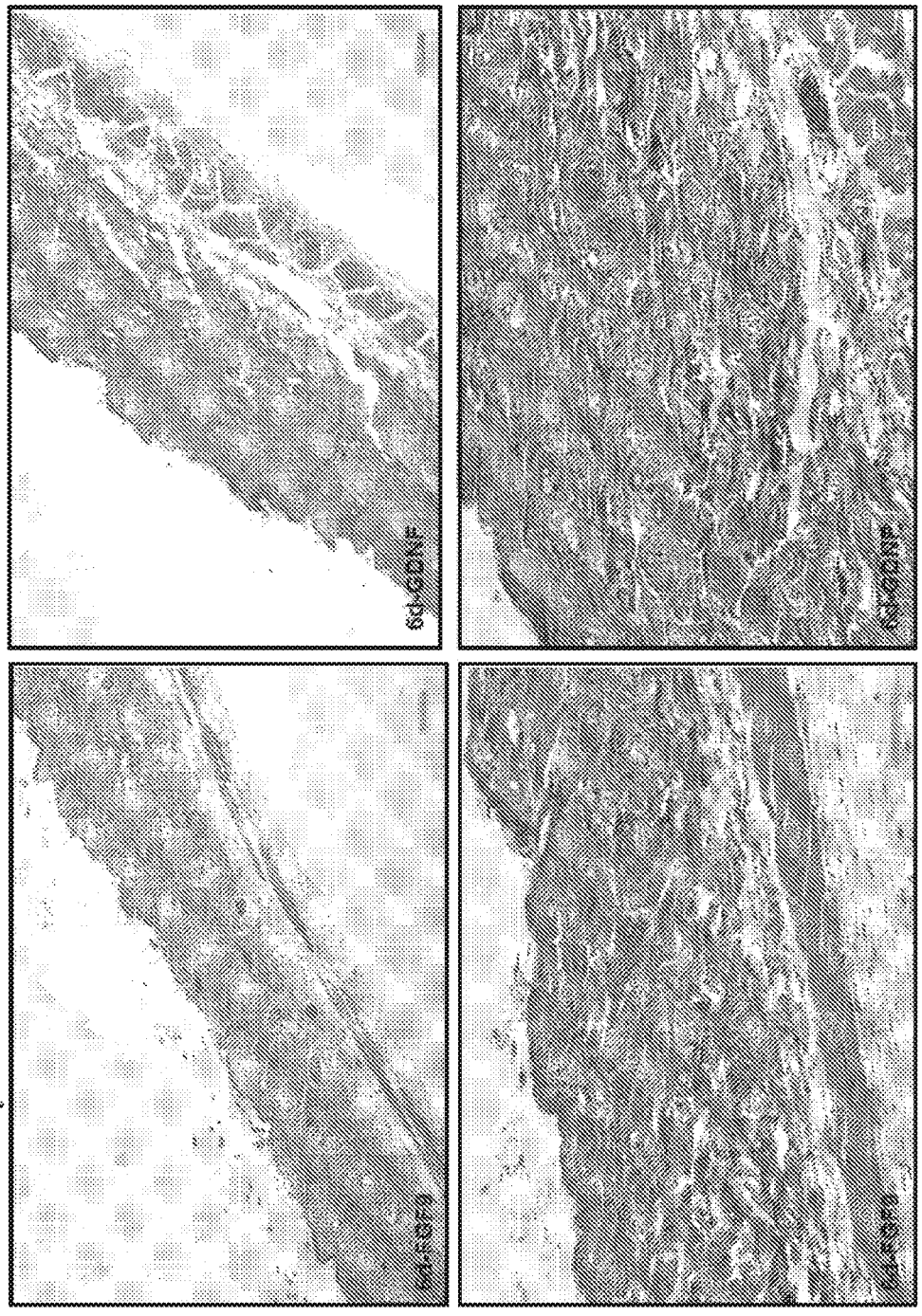
FIG. 4. New hair follicle development is specific to GDNF. Adult wild type B6 mice injected with 50 μg FGF9 or GDNF and analyzed after 6 days. There is an increased number of new hair follicles in sections from mice injected with GDNF. Scale=100 um.

For the GDNF injections we tested one dose of 100 μl 0.5 mg/ml GDNF protein (R&D system, cat no. 512-GF) versus five 100 μl injections of 0.1 mg/ml GDNF on alternate days. Skin tissue was harvested 15 days after injection (day 15) and paraffin sections were prepared and stained with H&E. In both groups an increase of hair follicles was detected, but a more striking increase when GDNF was administered at the lower dose over five time points, with the hair follicles being in different developmental stages (FIG. 3).

Example 4: Dose Comparison for Hair Follicle Development

Figure 5:
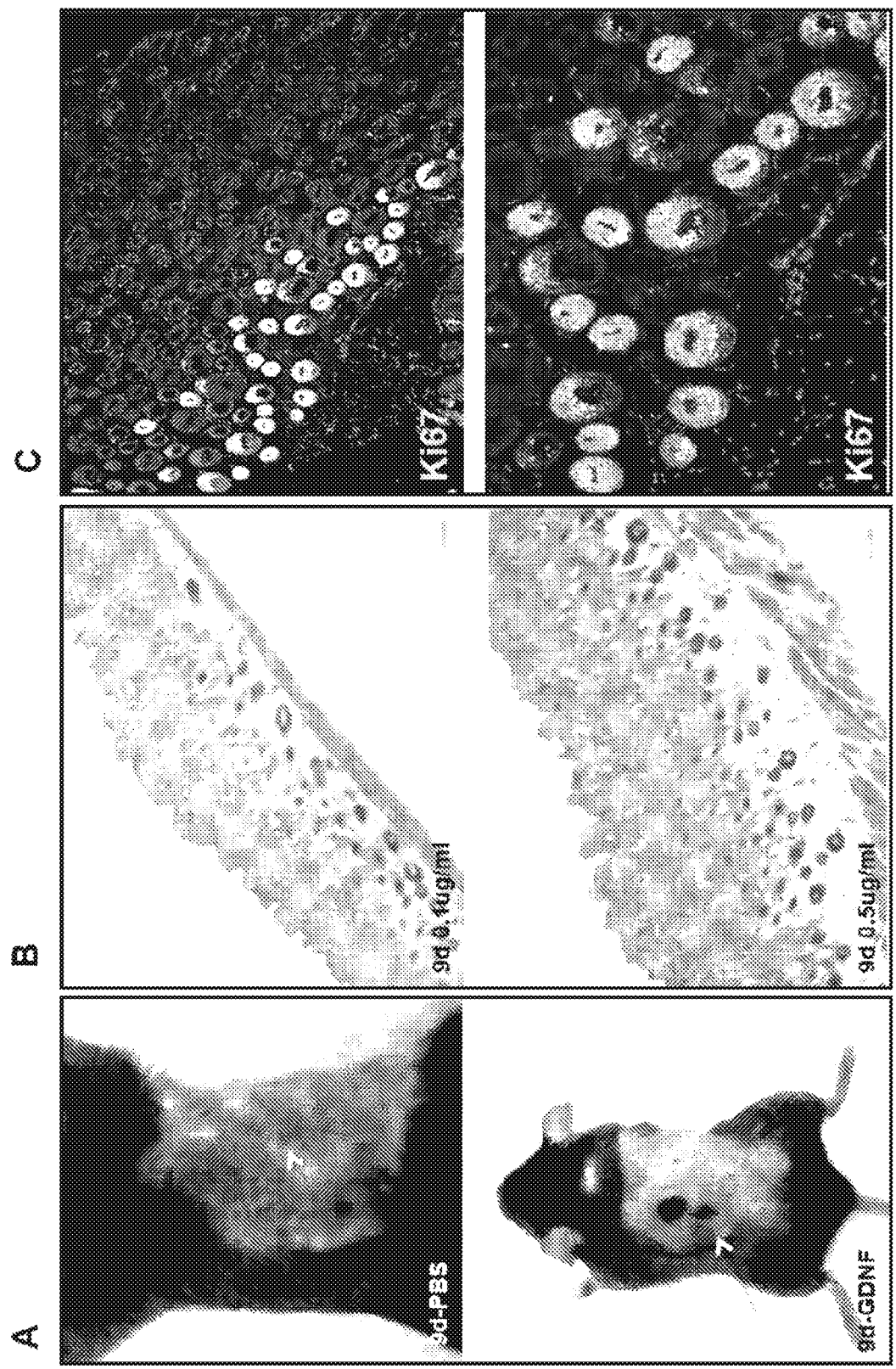
FIG. 5. Increased number of hair follicles at a higher dose GDNF. New hair follicles develop as early as day 9 in mice injected with 10 μg of GDNF compared to mice injected with PBS (A). By day 9 there are multiple layers of hair follicles in mice injected with 50 μg GDNF compared ones injected with 10 μg (B). Ki67 labeled cells in hair follicles of skin sections injected with GDNF (C).

Adult C57BL/6 (B6) wild type mice were injected with 100 μl of 0.1 mg/ml or 0.5 mg/ml recombinant GDNF protein (R&D system, cat no. 512-GF). The skin was analyzed after 9 days. One injection of 0.1 mg/ml was sufficient to induce hair follicle development at the injection site by day 9 (FIG. 5A). With the higher dose of 0.5 mg/ml more hair follicles were detectable (FIG. 5B). The rate of proliferation was assayed by 5-Bromo-2'-deoxyuridine (BrdU) labeling (Sigma, cat. no. B5002) according the protocols described by Sanjay et al. 2008, Methods in Mol Biol 438, 335-343. For this BrdU was injected intraperitoneally (i.p.) one day before collecting the skin. Most of the new hair follicles in the GDNF group stained positively indicating that these are proliferating while (data not shown). Alternatively skin sectioned were immunostained with Ki67 antibody, as Ki67 protein is an established marker for cell proliferation. Ki67 is expressed during active phase of the cell cycle G1, S and G2 and absent from resting cells G0. The staining of hair follicle cells with Ki67 antibody shows that they are in proliferative stage on day 9 after GDNF injection (FIG. 5C).

Figure 6:
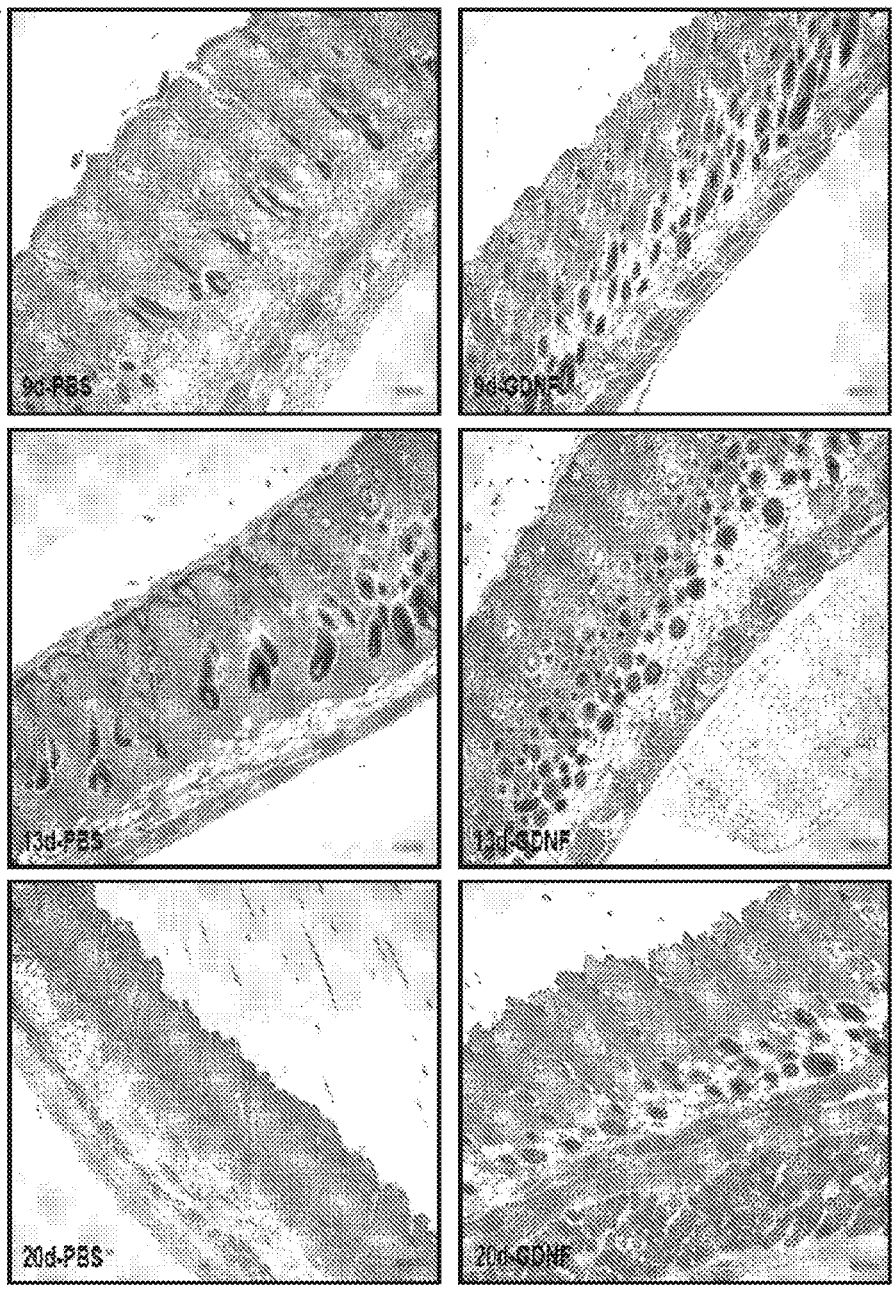
FIG. 6. Time course of hair follicle stimulation following GDNF treatment. Hematoxylin and eosin stained section of skin, injected (s.c.) with PBS or 50 μg of GDNF protein and analyzed after 9, 13, and 20 days. There are more numbers of hair follicles at the GDNF injected site compared to PBS. Scale =100 um FIG. 7. GDNF seems to be activating Notch1 signaling pathway. RT-PCR analysis on RNA extracted after 6 days from skin samples injected with 50 μg of GDNF or PBS in B6 wild type mice. Three fold increase in Notch1 but not c-Myc transcript was detected in GDNF injected sample. Transcript of Ret, the tyrosine kinase receptor, protein known to be in GDNF-GFRα1 signaling complex, is 4 fold higher in GDNF injected skin.

Adult B6 mice were injected with 100 μl of PBS or 0.5 mg/ml of GDNF (all injections were on the dorsal side and subcutaneous (s.c.)) and skin was isolated at day 6, 9, 13, 15, 20, and 30 after injections, paraffin embedded and sectioned for histological analysis. A dramatic increase in hair follicle numbers was observed on day 9 and 13 compared to mice injected with PBS (FIG. 6). By day 20 hair regeneration is complete in mice injected with PBS. Surprisingly, hair follicles are still proliferating in the GDNF injected group (FIG. 6).

Example 5: GDNF Signaling in the Epidermis

Figure 7:
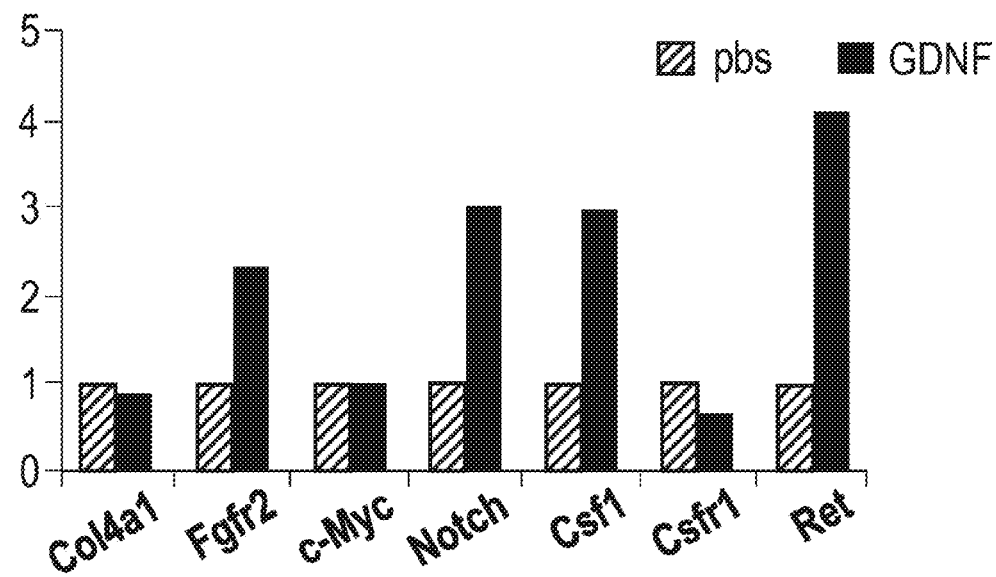

We analyzed the effects of GDNF (R&D system, cat no. 512-GF) on skin by quantitative RT-PCR (q-RT-PCR). For this total RNA was extracted from about 100 mg, about 8 mm diameter, skin tissue isolated from area injected either with PBS or 0.5 mg/ml GDNF protein 6 days after injection. RNA isolation was performed using Trizol Plus kit from Invitrogen. qRT-PCR of specific genes listed below was performed using One step Real-time RT-PCR SYBR green kit from Applied biosystems. Beta actin was used as internal control. Transcripts of selected genes were analyzed and normalized to beta-actin. The PCR protocol used here followed the RT-PCR protocol according to Applied Biosystems One step Real-time RT-PCR protocols. We tested expression of col4al, Ret, Fgfr2, c-myc, Notch1, Csf1 and Csfr1. A four-fold increase in Ret transcript was seen, and a three-fold increase for Notch1 and Csf1. For Ret and Notch1 one a role in hair growth has been described previously (Kato et al. 2001; Vauclair et al. 2005), and it may be that the action of GDNF is mediated by upregulating these. To date, it has not been shown that Notch1 is part of the GDNF signaling pathway, and this is the first time seeing this novel action of GDNF. We do not observe a change in c-myc, col4a1 and csfr1 expression. For example c-myc is not described as part of the GDNF signaling pathway and can be considered as negative control. While, it is known that c-myc over-expression results in proliferation epidermal cells, it does not seem to play a role here (FIG. 7).

The primers used for the q-RT-PCR are:

```
Fgfr2-Forward
                                   (SEQ ID NO: 14)
5'-ctctctacgtcatagttgaatatg-3

Fgfr2-Reverse
                                   (SEQ ID NO: 15)
5'-atatccctggccaggccaaagtct-3'

Ret-Forward
                                   (SEQ ID NO: 16)
5'-agatgtttatgaggaagattccta-3

Ret-Reverse
                                   (SEQ ID NO: 17)
5'-Tcctcgctgcagttgtctggcctc-3'

Col4a1-Forward
                                   (SEQ ID NO: 18)
5'-atgccctttctcttctgcaa-3'

Col4a1-Reverse
                                   (SEQ ID NO: 27)
5'-ctgcggaatctgaatggtct-3'

Csf1-Forward
                                   (SEQ ID NO: 19)
5'-gatccctgagtctgtcttccacct-3'

Csf1-Reverse
                                   (SEQ ID NO: 20)
5'-cagttccacctgtctgtcctcatcc-3'

Csf1r-Forward
                                   (SEQ ID NO: 21)
5'-gtaaagtggatggccccagagagc-3

Csf1r-Reverse
                                   (SEQ ID NO: 22)
5'-taggctccaggtcccagcaggactg-3' c-Myc-Forward
                                   (SEQ ID NO: 23)
5'-cagctcgcccaaatcctgtacctcgt-3' c-Myc-Reverse
                                   (SEQ ID NO: 24)
5'-cagacaccacatcaatttcttcctc-3'

Notch1-Forward
                                   (SEQ ID NO: 25)
5'-tgaagaacggagccaacaaggacatgc-3'

Notch1-Reverse
                                   (SEQ ID NO: 26)
5'-gcaatcggtccatgtgatccgtgatgt-3'
```

Example 6: GDNF Accelerates Wound Healing in B6 Mice

Mice were anesthetized using isoflurane and fur removed using clipper from the dorsal side. Loose fur was removed with dry gauze dampened with 70% ethanol. Equal size 3 mm of full thickness wounds were set using a biopsy punch needle on the dorsal side of adult B6 mice. The mice were housed individually and monitored daily after surgery.

Wounds were photographed on day 0 before injection and after one week, day 0 is counted as day of injection. Only one wound site was injected once with 100 µl of 0.5 mg/ml GDNF (R&D system, cat no. 512-GF) (arrow), the other wound was injected with PBS (vehicle control). The wound site that was injected with 100 µl of 0.5 mg/ml GDNF healed faster than the wound sites injected with PBS. After one week mice were sacrificed and tissue around the original wound was isolated to prepare sections. The sections of wound sites injected with PBS or GDNF were stained using H&E. By one week all layers of skin, epidermis, dermis and hair follicles are present at the wound site injected with GDNF compared to PBS injected sites (FIG. 8A). In the PBS control the skin does not show the three layers, but is still in the reconstruction phase after one week. The wound repair starts as early as 48 hrs after the wound is set with immune cells detectable. At the wound site red blood cell (RBC) infiltration is seen in both groups, but to a higher extent in the GDNF group (data not shown). By 96 hrs a complete layer of epithelium was observed throughout the wound site only for the GDNF group (FIG. 8B arrow) and many new blood vessels (arrowheads) are detectable in the GDNF injected site. In the PBS group less immune cells and blood vessels are detectable compared to the GDNF group. At the one week time point no new hair follicles are detectable in the PBS group.

Example 7: GDNF Accelerates Wound-Healing in Diabetic Mice

As diabetic model, we chose the diabetic mouse strain BKS.Cg-Dock7$^m$+/+Lepr$^{db}$/J (db/db; available from The Jackson Laboratory stock number 000642). Mice were anesthetized using isoflurane and fur removed using clipper from the dorsal side. Loose fur was removed with dry gauze dampened with 70% ethanol before 3 mm full thickness wounds were set into the dorsal skin creating 4/wounds per mouse using a biopsy punch needle. The mice were housed individually and monitored daily after surgery. We treated the wounds either with 100 µl PBS or 100 µl of 0.5 mg/ml GDNF recombinant protein (R&D system, cat no. 512-GF). Mice were sacrificed at several time points and tissues was collected, fixed in formalin, sectioned and sections were stained with H&E. 96 hours after wound setting and GDNF treatment, we detected neovascularization and blood vessel formation (FIG. 9A arrowhead) more pronounced in the GDNF group compared to the PBS group. The increase in new blood vessel formation in db/db mice treated with GDNF can be seen at the one week time point. Compared to wild type B6 mice wound healing in diabetes, takes two weeks instead of one week when injected with 0.5 mg/ml of GDNF but at a higher dose (250 µl of 0.5 mg/ml GDNF or 2.5 fold more). The healing process is greatly accelerated after GDNF treatment even in the db/db mice.

Example 8: GDNF Induces Blood Vessel Formation

FVB/NJ mice (n=5) (available from The Jackson Laboratory, cat no. 001800) were s.c. injected with 100 µl of PBS or 100 µl of 0.5 mg/ml GDNF protein (R&D system, cat no. 512-GF). 9 days after the injection the mice were sacrificed and the skin was isolated, photographed and fixed in formalin for histology. When the skin was isolated it was very striking that that the skin was showed more blood vessels with more branching in the GDNF group (Fig. xx). Analyzing the H&E stained sections confirmed an increased number of blood vessels around the GDNF injection site in comparison to the PBS injected tissue.

Example 9: Hydrogel Formulations for Therapeutic Admilistration

An optimized formulation of liposome-encapsulated GDNF in hydrogel is prepared for the growth factor to be applied at the wound site. The growth factor is loaded into the liposomes and mix with chitosan. Briefly, liposomes (from Sigma # L4395) are dissolved in 10 ml of chloroform: methanol mixture (2:1) in round bottom flask and air dried to thin film by jet stream of argon gas at 40oC. The thin film is then hydrated in water and passed through 0.2 um polycarbonate filters a few times to get small unilamellar vesicles. The liposome-encapsulated GDNF is prepared by sonication of the lipids and growth factor in 0.250:1 ratio (w/w) of growth factor to the lipid. These liposomes are added to a prechilled solution of chitosan (1.8% wt/vol in 2% acetic acid) by gentle stirring for 10 minutes before applying at the wound site.

The present invention and its embodiments have been described in detail. However, the scope of the present invention is not intended to be limited to the particular embodiments of any process, manufacture, composition of matter, compounds, means, methods, and/or steps described in the specification. Various modifications, substitutions, and variations can be made to the disclosed material without departing from the spirit and/or essential characteristics of the present invention. Accordingly, one of ordinary skill in the art will readily appreciate from the disclosure that later modifications, substitutions, and/or variations performing substantially the same function or achieving substantially the same result as embodiments described herein can be utilized according to such related embodiments of the present invention. Thus, the following claims are intended to encompass within their scope modifications, substitutions, and variations to processes, manufactures, compositions of matter, compounds, means, methods, and/or steps disclosed herein.

The contents of any patents, patent applications, and references cited throughout the specification are herein incorporated by reference in their entireties.

We claim:

1. A method for promoting hair growth comprising:
   administering to skin comprising hair follicles of a subject in need thereof a therapeutically effective amount of a topical formulation comprising recombinant human glial cell-derived neurotrophic factor (GDNF), wherein the therapeutically effective amount increases the number of hair follicles in the skin of the subject.

2. The method of claim 1, wherein the subject has androgenetic alopecia.

3. The method of claim 1, wherein the subject has acute or chronic telogen effluvium.

4. The method of claim 1, wherein the topical formulation is administered to the scalp of the subject.

5. The method of claim 1, wherein the topical formulation is an emulsion.

6. The method of claim 5, wherein the emulsion is a continuous phase emulsion.

7. The method of claim 5, wherein the emulsion is a disperse phase emulsion.

8. The method of claim 5, wherein the emulsion is a cream, lotion, ointment, or gel.

9. The method of claim 5, wherein the emulsion is an oil-in-water emulsion or a water-in-oil emulsion.

10. The method of claim 5, wherein the emulsion is a microemulsion.

11. The method of claim 1, wherein the therapeutically effective amount is administered daily for at least 3-5 days.

12. The method of claim 1, wherein the subject is a female.

13. A method for promoting hair growth comprising:
    administering to the scalp of a subject a therapeutically effective amount of a topical formulation comprising recombinant human glial cell-derived neurotrophic factor (GDNF), wherein the therapeutically effective amount increases the number of hair follicles in the scalp of the subject, and wherein the subject has androgenetic alopecia.

14. The method of claim 13, wherein the subject is female.

15. The method of claim 13, wherein the topical formulation is an emulsion.

16. A method for promoting hair growth comprising:
    administering to the scalp of a subject a therapeutically effective amount of a topical formulation comprising recombinant human glial cell-derived neurotrophic factor (GDNF), wherein the therapeutically effective amount increases the number of hair follicles in the scalp of the subject, and wherein the subject has acute or chronic telogen effluvium.

17. The method of claim 16, wherein the subject is female.

18. The method of claim 16, wherein the topical formulation is an emulsion.

* * * * *

SEQUENCE LISTING

```
Sequence total quantity: 27
SEQ ID NO: 1            moltype = DNA   length = 3810
FEATURE                 Location/Qualifiers
misc_feature            1..3810
                        note = Homo sapiens glial cell derived neurotrophic factor
                        (GDNF)
source                  1..3810
                        mol_type = genomic DNA
                        organism = Homo sapiens
```

```
SEQUENCE: 1
ccgcctccag cgcgcccttg ctgcccgcg cgaccccagg attgcgaact cttgcccctg   60
acctgttggg cggggctccg cgctccagcc atcagcccgg atgggtctcc tggctgggac  120
ttggggcacc tggagttaat gtccaaccta gggtctgcgg agacccgatc cgaggtgccg  180
ccgccggacg ggactttaag atgaagttat gggatgtcgt ggctgtctgc ctggtgctgc  240
tccacaccgc gtccgccttc ccgctgcccg ccggtaagag gcctcccgag gcgcccgccg  300
aagaccgctc cctcggccgc cgccgcgcgc ccttcgcgct gagcagtgac tcaaatatgc  360
cagaggatta tcctgatcag ttcgatgatg tcatggattt tattcaagcc accattaaaa  420
gactgaaaag gtcaccagat aaacaaatgg cagtgcttcc tagaagagag cggaatcggc  480
aggctgcagc tgccaaccca gagaattcca gaggaaaagg tcggagaggc cagaggggca  540
aaaaccgggg ttgtgtctta actgcaatac atttaaatgt cactgacttg ggtctgggct  600
atgaaaccaa ggaggaactg attttaggt actgcagcgg ctcttgcgat gcagctgaga  660
caacgtacga caaaatattg aaaaacttat ccagaaata aaggctggtg agtgacaaag  720
tagggcaggc atgttgcaga cccatcgcct ttgatgatga cctgtcgttt ttagatgata  780
acctggttta ccatattcta agaaagcatt ccgctaaaag gtgtggatgt atctgactcc  840
ggctccagag actgctgtgt attgcattcc tgctacagtg caaagaaagg gaccaaggtt  900
cccaggaaat gtttgcccag aatggaagat gaggaccaag gaggcggagg aggaggaaga  960
agaagaggag gaggaggagg aaggaggaga ggaggaggag ggcagccatc atgggagcct 1020
ggtagaggga gatccagcta cagacaactg gacaggagag agagaaaaca gccctctgga 1080
ttctccagga tggcagccga tgtcactaga agctcagggc tgatgttcct ggttggctat 1140
tgccaccatt tcagctgata cagtccacca tcactgatta ccgcgcggt tgcggtggat 1200
gcacttgaac caaaccagtg tatctcctgt gatttgtttt catgtgtccg aagacaccag 1260
ggaaacagag atcctggtgt tgttcctgt tattacgttt tactgctgaa agtaagaggt 1320
ttatttttct gtcactcagt ggagacatac cctgaaagg agaggggaaa aaaaagcaa  1380
agatacaaga gataatcacc tttgcatttg aaagttgagg cccgaggttt actacaacca 1440
gcattttgc caacggttgg tgattgattt ccatcacggt gtgtggggtg ggaagaagtt 1500
ggctaggaac caaaaggct gtgctcatga ttaaacacaa acctgaaggt atttccttta 1560
tgtccttgga aacaggaaac gagttgtggt tttcgccagc attcttgtag gagagaatcg 1620
gggaaggccc cgaactgccc ccgggcaggg agagcccctc aggcctgttg gtttacagag 1680
agacagatgt tacataacca gctccgttga tgcgtggtca ccagtgacca gagaagctac 1740
tcgatgcaat gcatctgttt cagatacaga aatatagaga agatatttat tgaaatttaa 1800
gttattgtta tttattaccg ttcactaatg aatttctctt ttttccctta tttattaaag 1860
tttcttttca aaggtgccaa agtatatgtg ctcgcaaaat gcaaagaaag gtgacaaaag 1920
gaaatttgaa ttgggaacaa gggtccatgc ttttcaaagt attaaaaagt tttttgccag 1980
gcaaaaatca cttacttac cttttaaga aatttgtca ttaattttcc ccagatttca 2040
gcattttcc caatttttat ttgtggagca tctcaggcaa gcccctttc ctggagcagc 2100
gtgcagagac cactggcact tgactttatt tcttccttgc tccattgctg aacagaaatg 2160
tcgtgggctc cacttcctgt tgtctttaag ctcttagtcc cctccacgta tacctatctg 2220
tactatgcat aaccatatgt agaaaaggtt cagttccttt cagttcctt tcctggattt 2280
aatgctgacc taaagtaat gtcgacaatg ctgtcaggta gctgccgttc taccgactcc 2340
ctccatccct gcccacccac tgccctcccg agaatatgct ggctgcccag tgcagcccgg 2400
gagacacagg ggccttccag aggtagggtc taccaggtcc tgtacaaccc ctgggctgtc 2460
accggggtc aacagctgct gctcctatat acccaaacac ctgacagctc cctggggagc 2520
agatggctga aagggtgct gaggaagcca tattgggacc agccacagcc acacacatgg 2580
agcctcatac ttaggagcgt gctgccttta aatgaaggtg gtcggggcca gtgcagcggc 2640
tcacacccat aatcccaaca ctttggaaag ccaaggtggg aggatctctt gaacccagga 2700
gtttgagacc agcttgggca acataggagg accctgctctc tacagaaact ttaaaaatta 2760
ggcaggcatg atggtgcaca cctgtggtcc cagctactca agaggctgaa ggaggatcac 2820
ttgagtccag aaggtcgagg ctgcagtgag ctgtgatcat gccactgcac tccagcctaa 2880
gtgacagtgc ggtaccctgt ctcaaaaaaa aaaaaaaaa aaaaaagagg ttggagcagg 2940
aggaagcata gggcgggaa cagccacctc ctccatgccc tagattgtga atttatcggg 3000
cagccaacac atgtatgaca cactaggccc tgtattacag cttgttacgc atttcataaa 3060
agggattttc attaaggaga taatctatta ctacctacct tagtggctac tagtataaaa 3120
ctatgacaga tttagcaatt aaatgaaata ctggcctcca tcaaataatc atagtaacaa 3180
gaagcagcag ttaccagaca tctgatcccc ttccccccaaa atacccaaat tcttcatggt 3240
tctgcccttc tctgtccttt ctgctcccct tgctcgcctg ggaaatggag gaaaggcctt 3300
ccctctcaca ctgtcttggg atcttgctga gaattcagac tgctcgaaac agtgacaaac 3360
cccagccatc cagtcattcg tggagcacaa tttggatgtg gccccagggg catctgtccc 3420
attcagagaa ccttggcagt gcgatggcca ctgttcccag gcttcaacct cagtgacccc 3480
ccccaacaac tccccatgga gagtccctgc ccaaaaaagc tgtaggatcc aagggggtc  3540
aatagctcgt tcccggcatc acctacacac cacaagcagg ttttaatgga agcaagttgc 3600
tccaccaaat ccacaaaagg gtaaagtttg tgattttct ttatcattgc gatcaccatc 3660
tgataccgta aggagtgcac ttgtttggaa gttctgactt ctctgatctg tcttggtcgt 3720
ttgtgttata aaccaaagt tctctacaga ctttatttt gtacaatatc atttttgtaac 3780
tttttacaaa taaaaactca tttctattgc                                  3810

SEQ ID NO: 2            moltype = DNA   length = 3655
FEATURE                 Location/Qualifiers
misc_feature            1..3655
                        note = Homo sapiens glial cell derived neurotrophic factor
                        (GDNF)
source                  1..3655
                        mol_type = genomic DNA
                        organism = Homo sapiens
SEQUENCE: 2
catacaggcc aaaagtctcc aagtccctgc taacttcttg ctctcgcaac agaataccta   60
tttaggtggg aagaatgagg tgtgggcggc aggctgggtg ccgccgccgg acgggacttt  120
aagatgaagt tatgggatgt cgtggctgtc tgcctggtgt tgctccacac cgcgtccgcc  180
ttcccgctgc ccgccgcaaa tatgccagag gattatcctg atcagttcga tgatgtcatg  240
```

```
gattttattc aagccaccat taaaagactg aaaaggtcac cagataaaca aatggcagtg   300
cttcctagaa gagagcggaa tcggcaggct gcagctgcca acccagagaa ttccagagga   360
aaaggtcgga gaggccagag gggcaaaaac cggggttgtg tcttaactgc aatacattta   420
aatgtcactg acttgggtct gggctatgaa accaaggagg aactgatttt taggtactgc   480
agcggctctt gcgatgcagc tgagacaacg tacgacaaaa tattgaaaaa cttatccaga   540
aatagaaggc tggtgagtga caaagtaggg caggcatgtt gcagacccat cgcctttgat   600
gatgacctgt cgtttttaga tgataacctg gtttaccata ttctaagaaa gcattccgct   660
aaaaggtgtg gatgtatctg actccggctc cagagactgc tgtgtattgc attcctgcta   720
cagtgcaaag aaaagggacca aggttcccag gaaatgtttg cccagaatgg aagatgagga   780
ccaaggaggc ggaggaggag gaagaagaag aggaggagga ggaggaggag gaggaggagg   840
aggaaggcag ccatcatggg agcctggtag agggagatcc agctacagac aactggacag   900
gagagagaga aaacagccct ctggattctc caggatggca gccgatgtca ctagaagctc   960
agggctgatg ttcctggttg gctattgcca ccatttcagc tgatacagtc caccatcact  1020
gattaccggc gcggttgcgg tggatgcact tgaaccaaac cagtgtatct cctgtgattt  1080
gttttcatgt gtccgaagac accagggaaa cagagatcct ggtgttgttc cttgttatta  1140
cgttttactg ctgaaagtaa gaggtttatt tttctgtcac tcagtggaga catacccctgg 1200
aaaggagagg ggaaaaaaaa agcaaagata caagagataa tcacctttgc atttgaaagt  1260
tgaggcccga ggtttactac aaccagcatt tttgccaacg gttggtgatt gatttccatc  1320
acggtgtgtg gggtgggaag aagttggcta ggaaccaaaa aggcgtgtgct catgattaaa  1380
cacaaacctg aagtatttc ctttatgtcc ttggaaacag gaaacgagtt gtggttttcg   1440
ccagcattct tgtaggagag aatcgggaa ggccccgaac tgcccccggg cagggagagc    1500
ccctcaggcc tgttggttta cagagagaca gatgttacat aaccagctcc gttgatgcgt  1560
ggtcaccagt gaccagagaa gctactcgat gcaatgcatc tgtttcagat acagaaatat  1620
agagaagata tttattgaaa tttaagttat tgttatttat taccgttcac taatgaattt  1680
ctctttttc cctatttat taaagtttct tttcaaaggt gccaaagtat atgtgctcgc    1740
aaaatgcaaa gaaaggtgac aaaaggaaat ttgaattggg aacaagggtc catgctttc   1800
aaagtattaa aaagttttt gccaggcaaa aatcacttac tttaccttt taagaaaatt   1860
tgtcattaat tttccccaga tttcagcatt tttcccaatt tttatttgtg gagcatctca  1920
ggcaagcccc ctttcctgga gcagcgtgca gagaccactg gcacttgact ttatttcttc  1980
cttgctccat tgctgaacag aaatgtcgtg ggctccactt cctgttgtct ttaagctctt  2040
agtcccctcc acgtatacct atctgtacta tgcataacca tatgtagaaa aggttcagtt  2100
ccttttagta ggtagtcctg gatttaatgc tgacctaaaa gtaatgtcga caatgctgtc  2160
aggtagctgc cgttctaccg actccctcca tccctgccca cccactgccc tcccgagaat  2220
atgctggctg cccagtgcag cccggggagac acaggggcct tccagaggta gggtctacca  2280
ggtcctgtac aaccccctggg ctgtcaccgg gggtcaacag ctgcgtcc tatatacccca   2340
aacacctgac agctccctgg ggagcagatg gctgagaagg gtgctgagga agccatattg   2400
ggaccagcca cagccacaca catggagcct catacttagg agcgtgctgc ctttaaatga  2460
aggtggtcgg ggccagtgca gcggctcaca cccataatcc caacactttg gaaagccaag  2520
gtgggaggat ctcttgaacc caggagtttg agaccagctg ggcaacata gggagaccct   2580
gtctctacag aaactttaaa aattaggcag gcatgatggt gcacacctgt ggtcccagct  2640
actcaagagg ctgaaggagg atcacttgag tccagaaggt cgaggctgca gtgagctgtg  2700
atcatgccac tgcactccag cctaagtgac agtgcgtac cctgtctcaa aaaaaaaaa    2760
aaaaaaaaa agaggttgga gcaggaggaa gcataggggc gggaacagcc acctcctcca   2820
tgccctagat tgtgaattta tcgggcagcc aacacatgta tgacacacta ggccctgtat  2880
tacagcttgt tacgcatttc ataaaaggga ttttcattaa ggagataatc tattactacc  2940
taccttagtg gctactagta taaaactatg acagatttag caattaaatg aaatactggc  3000
ctccatcaaa taatcatagt aacaagaagc agcagttacc agacatctga tccccttccc  3060
ccaaaatacc caaattcttc atggttctgc ccttctctgt cctttctgct ccccttgctc  3120
gcctgggaaa tggaggaaag gccttccctc tcacactgtc ttgggatctt gctgagaatt  3180
cagactgctc gaaacagtga caaacccccag ccatccagtc attcgtggag cacaatttgg  3240
atgtggcccc aggggcatct gtcccattca gagaaccttg gcagtgcgat ggccactgtt  3300
cccaggcttc aacctcagtg acccccccca acaactcccc atggagagtc cctgcccaaa  3360
aaagctgtag gatccaaggg gtgtcaatag ctcgttcccg gcatcaccta cacaccacaa  3420
gcaggtttta atggaagcaa gttgctccac caaatccaca aaagggtaaa gtttgtgatt  3480
tttctttatc attgcgatca ccatctgata ccgtaaggag tgcactttgt tggaagttct  3540
gacttctctg atctgtcttg gtcgtttgtg ttataaaacc aaagttctct acagacttta  3600
tttttgtaca atatcatttt gtaacttttt acaaataaaa actcatttct attgc        3655

SEQ ID NO: 3            moltype = DNA   length = 3830
FEATURE                 Location/Qualifiers
misc_feature            1..3830
                        note = Homo sapiens glial cell derived neurotrophic factor
                        (GDNF)
source                  1..3830
                        mol_type = genomic DNA
                        organism = Homo sapiens
SEQUENCE: 3
ccaaagcgtc cgagactggg tacagtcgtc caggcgtgac gggggcgcgg ggagccagtg    60
actcctctgg gaggggaagg gattaggggcc agaatctctc aaaggtgcaa aaatccagtc  120
aagagagggt tttcgggtat accacgagg attaaaactt tcaagacaaa tgcagtctttc  180
gcctaacagc aatggtgccg ccgccggacg ggactttaag atgaagttat gggatgtcgt  240
ggctgtctct ctggtgctgc tccacaccgc gtccgcctc ccgctgcccg ccggtaagag   300
gcctcccgag gcgcccgccg aagaccgctc cctcggccgc gccgcgcgc ccttcgcgct   360
gagcagtgac tcaaatatgc cagaggatta tcctgatcag ttcgatgatg tcatggattt   420
tattcaagcc accattaaaa gactgaaaag gtcaccagat aaacaaatgg cagtgcttcc   480
tagaagagag cggaatcggc aggctgcagc tgccaaccca gagaattcca ggaaaaggtc  540
cggagaggc cagaggggca aaaccgggg ttgtgtctta actgcaatac atttaaatgt    600
cactgacttg ggtctgggct atgaaccaa ggaggaactg atttttaggt actgcagcgg   660
ctcttgcgat gcagctgaga caacgtacga caaaatattg aaaaacttat ccagaaatag  720
```

```
aaggctggtg agtgacaaag tagggcaggc atgttgcaga cccatcgcct ttgatgatga   780
cctgtcgttt ttagatgata acctggttta ccatattcta agaaagcatt ccgctaaaag   840
gtgtggatgt atctgactcc ggctccagag actgctgtgt attgcattcc tgctacagtg   900
caaagaaagg gaccaaggtt cccaggaaat gtttgcccag aatggaagat gaggaccaag   960
gaggcggagg aggaggaaga agaaggagag gaggaggagg aggaggagga gggaggaggaa  1020
ggcagccatc atgggagcct ggtagaggga gatccagcta cagacaactg gacaggagag  1080
agagaaaaca gccctctgga ttctccagga tggcagccga tgtcactaga agctcagggc  1140
tgatgttcct ggttggctat tgccaccatt tcagctgata cagtccacca tcactgatta  1200
ccggcgcggt tgcggtggat gcacttgaac caaaccagtg tatctcctgt gatttgtttt  1260
catgtgtccg aagacaccag ggaaacagag atcctgctgt tgttccttgt tattacgttt  1320
tactgctgaa agtaagaggt ttattttttct gtcactcagt ggagacatac cctgaaaagg  1380
agaggggaaa aaaaaagcaa agatacaaga gataatcacc tttgcatttg aaagttgagg  1440
cccgaggttt actacaacca gcattttgc caacggttgg tgattgattt ccatcacggt    1500
gtgtggggtg ggaagaagtt ggctaggaac caaaaaggct gtgctcatga ttaaacacaa  1560
acctgaaggt atttccttta tgtccttgga aacaggaaac gagttgtggt tttcgccagc  1620
attcttgtag gagagaatcg gggaaggccc cgaactgccc ccgggcaggg agagcccctc  1680
aggcctgttg gtttacagag agacagatgt tacataacca gctccgttga tgcgtggtca  1740
ccagtgacca gagaagctac tcgatgcaat gcatctgttt cagatacaga aatatagaga  1800
agatatttat tgaaatttaa gttattgtta tttattaccg ttcactaatg aatttctctt  1860
ttttcccttta tttattaaag tttcttttca aaggtgccaa agtatatgtg ctcgcaaaat  1920
gcaaagaaag gtgacaaaag gaaatttgaa ttgggaacaa gggtccatgc ttttcaaagt  1980
attaaaaagt tttttgccag gcaaaaatca cttacttttac cttttttaaga aaatttgtca  2040
ttaattttcc ccagatttca gcattttcc caatttttat ttgtggagca tctcaggcaa    2100
gcccccttc ctggagcagc gtgcagagac cactggcact tgactttatt tcttccttgc    2160
tccattgctg aacagaaatg tcgtgggctc cacttcctgt tgtctttaag ctcttagtcc    2220
cctccacgta tacctatctg tactatgcat aaccatatgt agaaaaggtt cagttcctt     2280
tagtaggtag tcctggattt aatgctgacc taaaagtaat gtcgacaatg ctgtcaggta    2340
gctgccgttc taccgactcc ctccatccct gcccacccac tgccctcccg agaatatgct    2400
ggctgcccag tgcagcccgg gagacacagg ggccttccag aggtagggtc taccaggtcc    2460
tgtacaaccc ctgggctgtc accgggggtc aacagctgct gctcctatat acccaaacac    2520
ctgacagctc cctggggagc agatggctga gaagggtgct gaggaagcca tattgggacc    2580
agccacagcc acacacatgg agcctcatac ttaggagcgt gctgccttta aatgaaggtg    2640
gtcgggccca gtgcagcggc tcacacccat aatcccaaca ctttgaaaag ccaaggtggg    2700
aggatctctt gaacccagga gtttgagacc agcttgggca acatagggag accctgtctc    2760
tacagaaact ttaaaaatta ggcaggcatg atggtgcaca cctgtggtcc cagctactca    2820
agaggctgaa ggaggatcac ttgagtccag aaggctgagg ctgcagtgag ctgtgatcat    2880
gccactgcac tccagcctaa gtgacagtgc ggtaccctgt ctcaaaaaaa aaaaaaaaaa    2940
aaaaaagagg ttggagcagg aggaagcata ggggcgggaa cagccaccte ctccatgccc    3000
tagattgtga atttatcggg cagccaacac atgtatgaca cactaggccc tgtattacag    3060
cttgttacgc atttcataaa agggatttc attaaggaga taatctatta ctacctacct    3120
tagtggctac tagtataaaa ctatgacaga tttagcaatt aaatgaaata ctggcctcca   3180
tcaaataatc atagtaacaa gaagcagcag ttaccagaca tctgatcccc ttcccccaaa   3240
atacccaaat tcttcatggt tctgccctc tctgtccttt tgctgtccttg tgctcgcctg   3300
ggaaatggag gaaaggcctt ccctctcaca ctgtcttggg atcttgctga gaattcagac   3360
tgctcgaaac agtgacaaac cccagccatc cagtcattcg tggagcacaa tttggatgtg   3420
gccccagggg catctgtccc attcagagaa ccttggcagt gcgatggcca ctgttccag   3480
gcttcaacct cagtgacccc cccaacaac tccccatgga ggtccctgc ccaaaaaagc     3540
tgtaggatcc aagggggtgtc aatagctcgt tcccggcatc acctacacac acaagcagg   3600
ttttaatgga agcaagttgc tccaccaaat ccacaaaagg gtaaagtttg tgattttct    3660
ttatcattgc gatcaccatc tgataccgta aggagtgcac ttgtttggaa gttctgactt   3720
ctctgatctg tcttggtcgt ttgtgttata aaaccaaagt tctctacaga ctttattttt   3780
gtacaatatc attttgtaac tttttacaaa taaaaactca tttctattgc                3830
```

| SEQ ID NO: 4 | | moltype = DNA  length = 3752 |
|---|---|---|
| FEATURE | | Location/Qualifiers |
| misc_feature | | 1..3752 |
| | | note = Homo sapiens glial cell derived neurotrophic factor (GDNF) |
| source | | 1..3752 |
| | | mol_type = genomic DNA |
| | | organism = Homo sapiens |

SEQUENCE: 4

```
ccaaagcgtc cgagactggg tacagtcgtc caggcgtgac gggggcgcgg ggagccagtg     60
actcctctgg gaggggaagg gattagggcc agaatctctc aaaggtgcaa aaatccagtc   120
aagagagggt tttcgggtat accacgtgag gattaaaactt tcaagacaaa tgcagtcttt   180
gcctaacagc aatggtgccg ccgccggacg ggactttaag atgaagttat gggatgtcgt   240
ggctgtctgc ctggtgctgc tccacaccgc gtccgccttc ccgctgcccg ccgcaaatat   300
gccagaggat tatcctgatc agttcgatga tgtcatggat tttattcaag ccaccattaa   360
aagactgaaa aggtcaccag ataaacaaat ggcagtgctt cctagaagag agcggaatgt   420
gcaggctgca gctgccaacc cagagaattc cagagaaaa ggtcgagag gccgaggggc    480
caaaaaccgg ggttgtgtct taactgcaat acattaaatt gtcactgact tgggtctggg   540
ctatgaaacc aaggaggaac tgatttttag gtactgcagc ggctcttgcg atgcagctga   600
gacaacgtac gacaaatata tgaaaactt atccagaaat agaggctgg tgagtgacaa    660
agtagggcag gcatgttgca gacccatcgc cttttgatga ttttagatga                720
taacctggtt taccatattc taagaaagca ttccgctaaa aggtgtggat gtatctgact   780
ccggctccag agactgctgt gtattgcatt cctgctacag tgcaaagaaa gggaccaagg   840
ttcccaggaa atgtttgccc agaatggaag atgaggacca aggaggcgga ggaggaggaa   900
gaagaggagg aggaggaggg aggaggagag gagggagg aagcagcca tcatgggagc       960
ctggtagagg gagatccagc tacagacaac tggacaggag agagagaaaa cagccctctg  1020
```

```
gattctccag gatggcagcc gatgtcacta gaagctcagg gctgatgttc ctggttggct   1080
attgccacca tttcagctga tacagtccac catcactgat taccggcgcg ttgcggtgg   1140
atgcacttga accaaaccag tgtatctcct gtgatttgtt ttcatgtgtc cgaagacacc   1200
agggaaacag agatcctggt gttgttcctt gttattacgt tttactgctg aaagtaagag   1260
gttttatttt ctgtcactca gtggagacat accctgaaa ggagaggga aaaaaaagc     1320
aaagatacaa gagataatca cctttgcatt tgaaagttga ggcccgaggt ttactacaac   1380
cagcattttt gccaacggtt ggtgattgat ttccatcacg gtgtgtgggg tgggaagaag   1440
ttggctagga accaaaaagg ctgtgctcat gattaaacac aaacctgaag gtatttcctt   1500
tatgtccttg gaaacaggaa acgagttgtg gttttcgcca gcattcttgt aggagagaat   1560
cggggaaggc cccgaactgc ccccgggcag ggagagcccc tcaggcctgt tggtttacag   1620
agagacagat gttacataac cagctccgtt gatgcgtggt caccagtgac cagagaagct   1680
actcgatgca atgcatctgt ttcagataca gaaatataga gaagatattt attgaaattt   1740
aagttattgt tatttattac cgttcactaa tgaatttctc tttttcct tatttattaa     1800
agtttctttt caaaggtgcc aaagtatatg tgctcgcaaa atgcaaagaa aggtgacaaa   1860
aggaaatttg aattgggaac aagggtccta gcttttcaaa gtattaaaaa gttttttgcc   1920
aggcaaaaat cacttacttt acctttttaa gaaaatttgt cattaatttt ccccagattt   1980
cagcattttt cccaatttt atttgtggag catctcaggc aagcccctt tcctggagca     2040
gcgtgcagag accactggca cttgactta tttcttcctt gctccattgc tgaacagaaa    2100
tgtcgtgggc tccacttcct gttgtcttta agctcttagt cccctccacg tatacctatc   2160
tgtactatgc ataaccatat gtagaaaagg ttcagttcct tttagtaggt agtcctggat   2220
ttaatgctga cctaaaagta atgtcgacaa tgctgtcagg tagctgccgt tctaccgact   2280
ccctccatcc ctgcccaccc actgcccctcc cgagaatatg ctggctgccc agtgcagccc  2340
gggagacaca ggggccttcc agaggtaggg tctaccaggt cctgtacaac ccctgggctg   2400
tcaccggggg tcaacagctg ctgctcctat atacccaaac acctgacagc tccctgggga   2460
gcagatggct gagaaggggtg ctgaggaagc catattggga ccagccacag ccacacacat   2520
ggagcctcat acttaggagc gtgctgcctt taaatgaagg tggtcggggc cagtgcagcg   2580
gctcacaccc ataatcccaa cactttggaa agccaaggtg ggaggatctc ttgaacccag   2640
gagtttgaga ccagcttggg caacataggg agacccgtc tctacagaaa ctttaaaaat    2700
taggcaggca tgatggtgca cacctgtggt cccagctact caagaggctg aaggaggatc   2760
acttgagtcc agaaggtcga ggctgcagtg agctgtgatc atgccactgc actccagcct   2820
aagtgacagt gcggtaccct gtctcaaaa aaaaaaaaaa aaaaaaaga ggttggagca    2880
ggaggaagca taggggcggg aacagccacc tcctccatgc cctagattgt gaatttatcg   2940
ggcagccaac acatgtatga cacactaggc cctgtattac agcttgttac gcatttcata   3000
aaagggatttt tcattaagga gataatctat tactacctac cttagtggct actagtataa   3060
aactatgaca gatttagcaa ttaaatgaaa tactggcctc catcaaataa tcatagtaac   3120
aagaagcagc agttaccaga catctgatcc ccttccccca aaatacccaa attcttcatg   3180
gttctgccct tctctgtcct ttctgctccc cttgctcgcc tgggaaatgg aggaaaggcc   3240
ttccctctca cactgtcttg ggatcttgct gagaattcag actgctcgaa acagtgacaa   3300
accccagcca tccagtcatt cgtggagcac aatttggatg tggcccccagg ggcatctgtc   3360
ccattcagag aaccttggca gtgcgatggc cactgttccc aggcttcaac ctcagtgacc   3420
cccccaaca actcccatg gagagtccct gcccaaaaaa gctgtaggat ccaagggtgt    3480
tcaatagctc gttcccggca tcacctacac accacaagca ggtttaatg gaagcaagtt    3540
gctccaccaa atccacaaaa gggtaaagtt tgtgatttt ctttatcatt gcgatcacca    3600
tctgataccg taaggagtgc acttgtttgg aagttctgac ttctctgatc tgtcttggtc   3660
gtttgtgtta taaaaccaaa gttctctaca gactttattt ttgtacaata tcatttgta    3720
acttttacca aataaaaact catttctatt gc                                  3752

SEQ ID NO: 5           moltype = DNA  length = 485
FEATURE                Location/Qualifiers
misc_feature           1..485
                       note = cDNA encoding isoform 1
source                 1..485
                       mol_type = genomic DNA
                       organism = Homo sapiens
SEQUENCE: 5
caaatatgcc agaggattat cctgatcagt tcgatgatgt catggatttt attcaagcca   60
ccattaaaag actgaaaagg tcaccagata aacaaatggc agtgcttcct agaagagagc   120
ggaatcggca ggctgcagct gccaacccag agaattccag aggaaaaggt cggagaggcc   180
agaggggcaa aaaccgggt tgtgtcctaa ctgcaataca tttaaatgtc actgacttgg   240
gtctgggcta tgaaaccaag gaggaactga ttttttaggta ctgcagcggc tcttgcgatg   300
cagctgagac aacgtacgac aaaatattga aaaacttatc cagaaataga aggctggtga   360
gtgacaaagt agggcaggca tgttgcagac ccatcgcctt tgatgatgac ctgtcgtttt   420
tagatgataa cctggtttac catattctaa gaaagcattc cgctaaaagg tgtggatgta   480
tctga                                                                485

SEQ ID NO: 6           moltype = AA  length = 185
FEATURE                Location/Qualifiers
REGION                 1..185
                       note = misc_feature - glial cell line-derived neurotrophic
                        factor isoform 2 preproprotein
source                 1..185
                       mol_type = protein
                       organism = Homo sapiens
SEQUENCE: 6
MKLWDVVAVC LVLLHTASAF PLPAANMPED YPDQFDDVMD FIQATIKRLK RSPDKQMAVL   60
PRRERNRQAA AANPENSRGK GRRGQRGKNR GCVLTAIHLN VTDLGLGYET KEELIFRYCS   120
GSCDAAETTY DKILKNLSRN RRLVSDKVGQ ACCRPIAFDD DLSFLDDNLV YHILRKHSAK   180
RCGCI                                                                185
```

```
SEQ ID NO: 7              moltype = AA   length = 211
FEATURE                   Location/Qualifiers
REGION                    1..211
                          note = misc_feature - glial cell line-derived neurotrophic
                          factor isoform 1 preproprotein
source                    1..211
                          mol_type = protein
                          organism = Homo sapiens
SEQUENCE: 7
MKLWDVVAVC LVLLHTASAF PLPAGKRPPE APAEDRSLGR RRAPFALSSD SNMPEDYPDQ     60
FDDVMDFIQA TIKRLKRSPD KQMAVLPRRE RNRQAAAANP ENSRGKGRRG QRGKNRGCVL    120
TAIHLNVTDL GLGYETKEEL IFRYCSGSCD AAETTYDKIL KNLSRNRRLV SDKVGQACCR    180
PIAFDDDLSF LDDNLVYHIL RKHSAKRCGC I                                    211

SEQ ID NO: 8              moltype = AA   length = 228
FEATURE                   Location/Qualifiers
REGION                    1..228
                          note = misc_feature - glial cell line-derived neurotrophic
                          factor isoform 3 preproprotein
source                    1..228
                          mol_type = protein
                          organism = Homo sapiens
SEQUENCE: 8
MQSLPNSNGA AAGRDFKMKL WDVVAVCLVL LHTASAFPLP AGKRPPEAPA EDRSLGRRRA     60
PFALSSDSNM PEDYPDQFDD VMDFIQATIK RLKRSPDKQM AVLPRRERNR QAAAANPENS    120
RGKGRRGQRG KNRGCVLTAI HLNVTDLGLG YETKEELIFR YCSGSCDAAE TTYDKILKNL    180
SRNRRLVSDK VGQACCRPIA FDDDLSFLDD NLVYHILRKH SAKRCGCI                  228

SEQ ID NO: 9              moltype = AA   length = 202
FEATURE                   Location/Qualifiers
REGION                    1..202
                          note = misc_feature - glial cell line-derived neurotrophic
                          factor isoform 4 preproprotein
source                    1..202
                          mol_type = protein
                          organism = Homo sapiens
SEQUENCE: 9
MQSLPNSNGA AAGRDFKMKL WDVVAVCLVL LHTASAFPLP AANMPEDYPD QFDDVMDFIQ     60
ATIKRLKRSP DKQMAVLPRR ERNRQAAAAN PENSRGKGRR GQRGKNRGCV LTAIHLNVTD    120
LGLGYETKEE LIFRYCSGSC DAAETTYDKI LKNLSRNRRL VSDKVGQACC RPIAFDDDLS    180
FLDDNLVYHI LRKHSAKRCG CI                                              202

SEQ ID NO: 10             moltype = AA   length = 211
FEATURE                   Location/Qualifiers
REGION                    1..211
                          note = misc_feature - mouse GDN sequence
source                    1..211
                          mol_type = protein
                          organism = Mus sp.
SEQUENCE: 10
MKLWDVVAVC LVLLHTASAF PLPAGKRLLE APAEDHSLGH RRVPFALTSD SNMPEDYPDQ     60
FDDVMDFIQA TIKRLKRSPD KQAAALPRRE RNRQAAAASP ENSRGKGRRG QRGKNRGCVL    120
TAIHLNVTDL GLGYETKEEL IFRYCSGSCE SAETMYDKIL KNLSRSRRLT SDKVGQACCR    180
PVAFDDDLSF LDDNLVYHIL RKHSAKRCGC I                                    211

SEQ ID NO: 11             moltype = AA   length = 211
FEATURE                   Location/Qualifiers
REGION                    1..211
                          note = misc_feature - Rat GDN sequence
source                    1..211
                          mol_type = protein
                          organism = Rattus sp.
SEQUENCE: 11
MKLWDVVAVC LVLLHTASAF PLPAGKRLLE APAEDHSLGH RRVPFALTSD SNMPEDYPDQ     60
FDDVMDFIQA TIKRLKRSPD KQAAALPRRE RNRQAAAASP ENSRGKGRRG QRGKNRGCVL    120
TAIHLNVTDL GLGYETKEEL IFRYCSGSCE AAETMYDKIL KNLSRSRRLT SDKVGQACCR    180
PVAFDDDLWF LDDSLVYHIL RKHSAKRCGC I                                    211

SEQ ID NO: 12             moltype = AA   length = 196
FEATURE                   Location/Qualifiers
REGION                    1..196
                          note = Consensus sequence derived from human and mouse GDN
                          sequences
source                    1..196
                          mol_type = protein
                          organism = synthetic construct
SEQUENCE: 12
MKLWDVVAVC LVLLHTASAF PLPAGKREAP AEDSLGRRPF ALSDSNMPED YPDQFDDVMD     60
FIQATIKRLK RSPDKQALPR RERNRQAAAA PENSRGKGRR GQRGKNRGCV LTAIHLNVTD    120
```

```
LGLGYETKEE LIFRYCSGSC AETYDKILKN LSRRRLSDKV GQACCRPAFD DDLSFLDDNL    180
VYHILRKHSA KRCGCI                                                   196

SEQ ID NO: 13           moltype = AA  length = 195
FEATURE                 Location/Qualifiers
REGION                  1..195
                        note = Consensus sequence derived from human and rat GDN
                          sequences
source                  1..195
                        mol_type = protein
                        organism = synthetic construct
SEQUENCE: 13
MKLWDVVAVC LVLLHTASAF PLPAGKREAP AEDSLGRRPF ALSDSNMPED YPDQFDDVMD    60
FIQATIKRLK RSPDKQALPR RERNRQAAAA PENSRGKGRR GQRGKNRGCV LTAIHLNVTD    120
LGLGYETKEE LIFRYCSGSC AAETYDKILK NLSRRRLSDK VGQACCRPAF DDDLFLDDLV    180
YHILRKHSAK RCGCI                                                    195

SEQ ID NO: 14           moltype = DNA  length = 24
FEATURE                 Location/Qualifiers
misc_feature            1..24
                        note = Synthetic primer: Fgfr2-Forward
source                  1..24
                        mol_type = other DNA
                        organism = synthetic construct
SEQUENCE: 14
ctctctacgt catagttgaa tatg                                          24

SEQ ID NO: 15           moltype = DNA  length = 24
FEATURE                 Location/Qualifiers
misc_feature            1..24
                        note = Synthetic primer: Fgfr2-Reverse
source                  1..24
                        mol_type = other DNA
                        organism = synthetic construct
SEQUENCE: 15
atatccctgg ccaggccaaa gtct                                          24

SEQ ID NO: 16           moltype = DNA  length = 24
FEATURE                 Location/Qualifiers
misc_feature            1..24
                        note = Synthetic primer: Ret-Forward
source                  1..24
                        mol_type = other DNA
                        organism = synthetic construct
SEQUENCE: 16
agatgtttat gaggaagatt ccta                                          24

SEQ ID NO: 17           moltype = DNA  length = 24
FEATURE                 Location/Qualifiers
misc_feature            1..24
                        note = Synthetic primer: Ret-Reverse
source                  1..24
                        mol_type = other DNA
                        organism = synthetic construct
SEQUENCE: 17
tcctcgctgc agttgtctgg cctc                                          24

SEQ ID NO: 18           moltype = DNA  length = 20
FEATURE                 Location/Qualifiers
misc_feature            1..20
                        note = Synthetic primer: Col4a1-Forward
source                  1..20
                        mol_type = other DNA
                        organism = synthetic construct
SEQUENCE: 18
atgccctttc tcttctgcaa                                               20

SEQ ID NO: 19           moltype = DNA  length = 24
FEATURE                 Location/Qualifiers
misc_feature            1..24
                        note = Synthetic primer: Csf1-Forward
source                  1..24
                        mol_type = other DNA
                        organism = synthetic construct
SEQUENCE: 19
gatccctgag tctgtcttcc acct                                          24

SEQ ID NO: 20           moltype = DNA  length = 25
FEATURE                 Location/Qualifiers
```

-continued

```
misc_feature            1..25
                        note = Synthetic primer: Csf1-Reverse
source                  1..25
                        mol_type = other DNA
                        organism = synthetic construct
SEQUENCE: 20
cagttccacc tgtctgtcct catcc                                          25

SEQ ID NO: 21           moltype = DNA   length = 24
FEATURE                 Location/Qualifiers
misc_feature            1..24
                        note = Synthetic primer: Csf1r-Forward
source                  1..24
                        mol_type = other DNA
                        organism = synthetic construct
SEQUENCE: 21
gtaaagtgga tggccccaga gagc                                           24

SEQ ID NO: 22           moltype = DNA   length = 25
FEATURE                 Location/Qualifiers
misc_feature            1..25
                        note = Synthetic primer: Csf1r-Reverse
source                  1..25
                        mol_type = other DNA
                        organism = synthetic construct
SEQUENCE: 22
taggctccag gtcccagcag gactg                                          25

SEQ ID NO: 23           moltype = DNA   length = 26
FEATURE                 Location/Qualifiers
misc_feature            1..26
                        note = Synthetic primer: c-Myc-Forward
source                  1..26
                        mol_type = other DNA
                        organism = synthetic construct
SEQUENCE: 23
cagctcgccc aaatcctgta cctcgt                                         26

SEQ ID NO: 24           moltype = DNA   length = 25
FEATURE                 Location/Qualifiers
misc_feature            1..25
                        note = Synthetic primer: c-Myc- Reverse
source                  1..25
                        mol_type = other DNA
                        organism = synthetic construct
SEQUENCE: 24
cagacaccac atcaatttct tcctc                                          25

SEQ ID NO: 25           moltype = DNA   length = 27
FEATURE                 Location/Qualifiers
misc_feature            1..27
                        note = Synthetic primer: Notch1 -Forward
source                  1..27
                        mol_type = other DNA
                        organism = synthetic construct
SEQUENCE: 25
tgaagaacgg agccaacaag gacatgc                                        27

SEQ ID NO: 26           moltype = DNA   length = 27
FEATURE                 Location/Qualifiers
misc_feature            1..27
                        note = Synthetic primer: Notch1- Reverse
source                  1..27
                        mol_type = other DNA
                        organism = synthetic construct
SEQUENCE: 26
gcaatcggtc catgtgatcc gtgatgt                                        27

SEQ ID NO: 27           moltype = DNA   length = 20
FEATURE                 Location/Qualifiers
misc_feature            1..20
                        note = Synthetic primer: Col4a1-Reverse
source                  1..20
                        mol_type = other DNA
                        organism = synthetic construct
SEQUENCE: 27
ctgcggaatc tgaatggtct                                                20
```